US007585657B2

(12) United States Patent
Kawaoka

(10) Patent No.: US 7,585,657 B2

(45) Date of Patent: Sep. 8, 2009

(54) SIGNAL FOR PACKAGING OF INFLUENZA VIRUS VECTOR

(75) Inventor: Yoshihiro Kawaoka, Middletown, WI (US)

(73) Assignee: Wisconsin Alumni Research Foundation, Madison, WI (US)

(*) Notice: Subject to any disclaimer, the term of this patent is extended or adjusted under 35 U.S.C. 154(b) by 0 days.

(21) Appl. No.: 11/509,249

(22) Filed: Aug. 24, 2006

(65) Prior Publication Data

US 2007/0141699 A1 Jun. 21, 2007

Related U.S. Application Data

(62) Division of application No. 10/366,630, filed on Feb. 12, 2003, now Pat. No. 7,226,774.

(60) Provisional application No. 60/438,679, filed on Jan. 7, 2003, provisional application No. 60/356,538, filed on Feb. 13, 2002.

(51) Int. Cl.

| | |
|---|---|
| ***C12N 7/01*** | (2006.01) |
| ***C12N 15/86*** | (2006.01) |
| ***C12N 15/44*** | (2006.01) |
| *A61K 39/145* | (2006.01) |

(52) U.S. Cl. .............. 435/235.1; 435/320.1; 424/199.1; 424/93.2; 536/23.1

(58) Field of Classification Search ....................... None
See application file for complete search history.

(56) References Cited

U.S. PATENT DOCUMENTS

| | | | | |
|---|---|---|---|---|
| 5,166,057 | A | 11/1992 | Palese et al. | |
| 5,786,199 | A * | 7/1998 | Palese | 435/239 |
| 5,854,037 | A | 12/1998 | Palese et al. | |
| 6,001,634 | A | 12/1999 | Palese et al. | |
| 6,271,011 | B1 * | 8/2001 | Lee et al. | 435/200 |
| 7,226,774 | B2 | 6/2007 | Kawaoka | |
| 2004/0241139 | A1 * | 12/2004 | Hobom et al. | 424/93.2 |

FOREIGN PATENT DOCUMENTS

| | | | |
|---|---|---|---|
| CA | 2379012 | | 1/2001 |
| EP | 1201760 | A1 | 5/2002 |
| WO | WO-0060050 | A2 | 10/2000 |
| WO | WO-0179273 | A2 | 10/2001 |

OTHER PUBLICATIONS

Li et al (Journal of Viology 166:399-404, 1992).*

*NCBI Locus P03470, WSN Neuraminidase sequence*[online][retreived Sep. 28, 2005]Retreived from the internet <URL:http://wwww.ncbi.nlm.nih.gov/entrez/viewer.fcgi?db=protein&val=128557>.

Bilsel, P. , et al., "Mutations in the Cytoplasmic Trail of Influeza A Virus Neuraminidase Affect Incorporation into Virions", *Journal of Virology*, 67(11). (Nov. 1993),6762-6767.

Castrucci, M. R., et al., "Attenuation of Influenza a Virus by Insertion of a Foreign Epitope into the Neuraminidase", *Journal of Virology*, 66 (8). American society of Microbiology, (Aug. 1992),4647-4653.

Castrucci, M. R., et al., "Protection against Lethal Lymphocytic Choriomeningitis Virus (LCMV) Infection by Immunization of Mice with an Influenza Virus Containing an LCMV Epitiope Recognized by Cytotoxic T Lymphocytes", *Journal of Virology*, vol. 68(6), (Jun. 1994),3486-3490.

Crescenzo-Chaigne, Bernadette, et al., "Comparative analysis of the ability of the polymerase complexes of influenza viruses type A, B and C to assemble into functional RNPs that allow expression and replication of heterotypic model RNA templates in vivo", *Virology*, 265(2), (Dec. 1999),342-353.

Desselberger, Ulrich, et al., "The 3' and 5'-terminal sequences of influenza A, B and C virus RNA segments are highly conserved and show partial inverted complementarity", *Gene*, 8 (3), (Feb. 1980),315-328.

Dollenmaier, G. , et al., "Membrane-Associated Respiratory Syncytial Virus F Protein Expressed From A Human Rhinovirus Type 14 Vector Is Immunogenic", *Virology*, 281(2), (Mar. 2001),216-230.

Durbin, A. P., et al., "Human Parainfluenza Virus Type 3 (PIV3) Expressing The Hemagglutinin Protein Of Measles Virus Provides A Potential Method For Immunization Against Measles Virus and PIV3 in Early Infancy", *Journal of Virology*, 74(15), (Aug. 2000),6821-6831.

Flandorfer, A. , et al., "Chimeric Influenza A Viruses with a Functional Influenza B Virus Neuraminidase or Hemagglutinin", *Journal of Virology*, 77(17), (Sep. 2003),9116-9123.

Fujii, Y , et al., "The packaging of influenza viral genome", *Virus*, 52 (1), Uirusu (Japanese Journal Name),(Jun. 2002),203-206.

Garcia-Sastre, A. , et al., "Intoduction of Foreign Sequences into the Genome of Influenza A Virus", *Dev. Biol. Stand.* vol. 82, (1994),237-246.

Ghate, Anita A., et al., "Influenza Type B Neuraminidase Can Replace the Function of Type A Neuraminidase", *Virology*, 264 (2), (Nov. 1999),265-277.

Gillenland, H. E., et al., "Chimeric Influenza Virus Incorporating Epitopes of Outer Membrane Protein F as a Vaccine Against Pulmonary Infection with Pseudomonas Aeruginosa", *Behring Inst. Mitt.* 98, (Feb., 1997),291-301.

Hiti, A. , et al., "Complete Nucleotide Sequence of TRHE Neuraminidase Gene of Human Influenza", WWW.NCBI.NLM.NIH.GOV/ENTREZ/VIEWER.FCGI?DB=PROTEIN&VAL=128557>, (1982),730-734.

Hughes, Mark T., "Adaptation of Influenza A Viruses to Cells Expressing Low Levels of Sialic Acid Leads to Loss of Neuraminidase Activity", *Journal of Virology*, 75 (8), (Apr. 2001),3766-3770.

Hughes, Mark T., "Influenza A Viruses Lacking Sialidase Activity Can Undergo Multiple Cycles of Replication in Cell Culture, Eggs, or Mice", *Journal of Virology*, 74 (11)k, (Jun. 2000),5206-5212.

(Continued)

*Primary Examiner*—Mary E Mosher
(74) *Attorney, Agent, or Firm*—Schwegman, Lundberg & Woessner, P.A.

(57) ABSTRACT

The invention provides a packaging (incorporation) signal for influenza virus vectors, and methods of using the signal to transmit and maintain influenza viral and foreign nucleic acid in virus and cells.

31 Claims, 30 Drawing Sheets

OTHER PUBLICATIONS

Liu, Chongguang , "Influenza type A virus neuraminidase does not play a role in viral entry, replication, assembly, or budding.", *Journal of Virology*, 69(2), (Feb. 1995),1099-106.
Liu, Chongguang , "Selection and characterization of a neuraminidase-minus mutant of influenza virus and its rescue by cloned neuraminidase genes. ", *Virology*, 194(1), (1993),403-407.
Luytjes, W. , "Amplification, Expression, and Packaging of a Foriegn Gene by Influenza Virus", *Cell*, 59(6), (1989),1107-1113.
Mitnaulk, Lyndon J., et al., "Balanced Hemagglutinin and Neuraminidase Activities are Critical for Efficient Replication of Influenza A Virus", *Journal of Virology*, 74 (13), (Jul. 2000),6015-6020.
Muster, T. , "An Influenza A Virus Containing Influenza B Virus 5' and 3' Noncoding Regions on the Neuraminidase Gene is Attenuated in Mice", *Proceeding of the National Academy of Sciences USA*, 88, (Jun. 1991),5177-5181.
Neumann, Gabriele, et al., "Generation of Influenza A Virus Entirely from Cloned cDNAs", *Proceedings of the National Academy of Sciences USA*, 96, (Aug. 1999),9345-9350.
Neumann, Gabriele, et al., "Influenza A virus NS2 protein mediates vRNP nuclear export through NES-independent interaction with hCRM1", *The EMBO Journal*, 19 (24), (2000),6751-6758.
Piatti, G. , "Identification Of Immunodominant Epitopes In The Filamentous Hemagglutinin of Bordetella Pertusis", *FEMS Immunology and Medical Microbiology*, 23(3), (Mar. 1999),235-241.
Portela, Agustin , et al., "Replication of orthomyxoviruses", *Advances in Virus Research*, 54, (1999),319-348.
Rodrigues, M. , et al., "Influenza and Vaccinia Viruses Expressing Malaria CD+T and B Cell Epitopes", *The American Association of Immunologists*, 153,(1994),4636-4648.
Strobel, I. , et al., "Efficient Expression Of The Tumor -Associated Antigen MAGE-3 In Human Dendritic Cells, Using An Avian Influenza Virus Vector", *Human Gene Therapy*, 11(16), (Nov. 1, 2000),2207-2218.
Yang, Ping , "Hemagglutinin specificity and neuraminidase coding capacity of neuraminidase-deficient influenza viruses.", *Virology*, 229(1), (1997),155-165.
Castrucci, Maria R., et al., "Biologic Importance of Neuraminidase Stalk Length in Influenza A Virus", *Journal of Virology*, Feb. 1993, vol. 67, No. 2, (Oct. 22, 1992),759-764.
Garcia-Sastre, Adolfo , et al., "Use of a Mammalian Internal Ribosomal Entry Site Element for Expression of a Foreign Protein by a Transfectant Influenza Virus", *Journal of Virology*, Oct. 1994, vol. 68, No. 10, (Jun. 30, 1994),p. 6254-6261.
Neumann, Garbriele, et al., "Mutational Analysis of Influenza Virus Promoter Elements In Vivo", *Journal of General Virology*(1995), 76, (Feb. 24, 1995),1709-1717.
"Australian Patent Application Serial No. 2003219745, Examiner's First Report mailed Feb. 14, 2007", 2 pgs.
"Australian Patent Application Serial No. 2003219745, Response filed Mar. 14, 2008 to Examiner's First Report mailed Feb. 14, 2007", 24 pgs.
"Brazilian Application Serial No. PI 0307679-2, Office Action published in Patent Gazette No. 1871 of Nov. 14, 2006", 2 pgs.
"Brazilian Application Serial No. PI 0307679-2, Petition filed Jan. 10, 2007 in Response to Office Action published on Nov. 14, 2006", 6 pgs.
"Canadian Application Serial No. 2,492,097, Amendment and Response filed Oct. 23, 2008 to Office Action mailed Apr. 24, 2008", 14 pgs.
"Canadian Application Serial No. 2,492,097, Office Action mailed Apr. 24, 2008", 3 pgs.
"Chinese Application Serial No. 03808356.6, Office Action Mailed on Sep. 5, 2008", (w/ English Translation),6 pgs.
"European Application Serial No. 03716017.3, Communication and Supplementary European Search Report mailed Jan. 02, 2008", 8 pgs.
"European Application Serial No. 03716017.3, Communication mailed Jul. 26, 2006", 2 pgs.
"European Application Serial No. 03716017.3, Response filed Jul. 28, 2006 to Communication mailed May 23, 2006", 5 pgs.
"European Application Serial No. 037160173, Communication mailed May 23, 2006", 3 pgs.
"European Application Serial No. 037160173, Communication mailed Oct. 20, 2008", 7 pgs.
"International Application Serial No. PCT/US03/04233, International Search Report mailed Dec. 16, 2005", 5 pgs.
"Israel Application Serial No. 163,546, Response filed Nov. 27, 2008 to Office Action", 13 pgs.
"Japanese Application Serial No. 2003-568038, Argument and an Amendment filed Dec. 10, 2008 in Response to Notice of Reasons for Rejection mailed Jul. 10, 2008", 105 pgs.
"Japanese Application Serial No. 2003-568038, Notice of Reasons for Rejection mailed Jul. 10, 2008", 6 pgs.
"Japanese Application Serial No. 2003-568038, Official Action mailed Jul. 21, 2005", 4 pgs.
"Japanese Application Serial No. 2003-568038, Request for Examination filed Aug. 19, 2005 in Response to Official Action mailed Jul. 21, 2005", 8 pgs.
"Mexican Application Serial No. PA/a/2004/007914, Response filed Jun. 13, 2008 to Office Action mailed Feb. 14, 2008", 46 pgs.
"Mexican Application Serial No. PA/a/2004/007914, Office Action mailed Feb. 14, 2008", 3 pgs.
"Nucleotide sequences of influenza virus segments 1 and 3 reveal mosaic structure of a small viral RNA segment", *Database Uniprot*, XP002459965,(Nov. 14, 2001),2 pgs.
"Prosecution File History for U.S. Appl. No. 10/366,630, filed Feb. 12, 2003",104 pgs.
Duhaut, S., et al., "Approximately 150 nucleotides from the 5' end of an influenza A segment 1 defective virion RNA are needed for genome stability during passage of defective virus in infected cells.", *Virology, 275(2)*, (Sep. 30, 2000), 278-285.
Duhaut, S. D., et al., "Heterologous Protection of Misce from a lethal human HINI Influenza A Virus Infection by H3NB Equine Defective Interfering Virus: Comparison of Defective RNA Sequences Isolated from the DI Inoculum and Mouse Lung", *Virology, 248(2)*, Academic Press, Orlando, Us,(Sep. 1, 1998),241-253.
Fuji, Y., et al., "Selective incorporation of influenza virus RNA segments into virions", *Proc. Nat'l. Acad. Sci. USA*, (2003),2002-2007.
Percy, N. , et al., "Expression of a foreign protein by influenza A virus.", *J. Virol.*, 68(7), (Jul., 1994),4486-4492.
Restifo, N. P., et al., "Transfectant influenza A viruses are effective recombinant immunogens in the treatment of experimental cancer.", *Virology*, 249(1), (Sep. 15, 1998),89-97.
Shinya, K., et al., "Characterization of a neuraminidase-deficient influenza a virus as a potential gene delivery vector and a live vaccine", *Journal of Virology*, 78(6), (Mar. 2004), 3083-3088.
Walker, W. S., et al., "HEL-Flu: an influenza virus containing the hen egg lysozyme epitope recognized by CD4+ T cells from mice transgenic for an alphabeta TCR", *J. Immunol.*, 159(6), (Sep., 1997), 2563-2566.
"Israel Application No. 163546, First Examination Report mailed Jul. 28, 2008", 2 pgs.
"Israel Application No. 163546, Substantive Examination Report mailed Feb. 23, 2009", 3 pgs.

* cited by examiner

| virus | packaging rate(%) |
|---|---|
| NA(183)GFP(157) | 91 |
| NA(0)GFP(0) | 0.1 |
| NA(183)GFP(0) | 38 |
| NA(0)GFP(157) | 1.9 |
| NA(90)GFP(0) | 40 |
| NA(45)GFP(0) | 38 |
| NA(21)GFP(0) | 39 |
| NA(18)GFP(0) | 6.9 |
| NA(183)GFP(78) | 78 |
| NA(183)GFP(39) | 71 |

| | EFFICIENCY VIRION INCORPORATION (%) |
|---|---|
| HA(468)GFP(513) 3' 33 NT 468 NT — [GFP] — 513 NT 45 NT 5' | 42.8 |
| HA(0)GFP(0) — — — — [GFP] — — — — | 3.9 |
| HA(0)GFP(1011) —[GFP]—————— | 6.8 |
| HA(966)GFP(0) ——————[GFP]— | 8.4 |
| HA(216)GFP(291) — — — [GFP] — — — | 51.5 |
| HA(15)GFP(268) ————[GFP]———— | 43.8 |
| HA(15)GFP(80) ————[GFP]———— | 31.9 |
| HA(15)GFP(75) ————[GFP]———— | 16.2 |
| HA(15)GFP(54) ————[GFP]———— | 5.9 |
| HA(9)GFP8(0) ————[GFP]———— | 65.4 |
| HA(6)GFP(80) ————[GFP]———— | 48.1 |
| HA(3)GFP(80) ————[GFP]———— | 33.4 |

◄ vRNA

INCORPORATION EFFICIENCY OF MODEL NS RNA SEGMENTS

| MODEL NS RNA SEGMENTS | INCORPORATION EFFICIENCY (%) |
|---|---|
| 150 — 150 | 62.4 |
| 150 — 30 | 47.0 |
| 150 — (short) | 20.0 |
| 30 — 150 | 47.0 |
| (short) — 150 | 2.0 |
| 120 — 150 | 3.9 |
| (short) — (short) | 0.5 |

INCORPORATION EFFICIENCY OF MODEL M RNA SEGMENTS

| Segment (1 26 247 ... 785 1004 10027) | INCORPORATION EFFICIENCY (%) |
|---|---|
| M — GFP — M | 80.54 |
| (M deleted) GFP — M | 11.43 |
| M — GFP — (M deleted) | 0.25 |
| (M deleted) GFP — (M deleted) | 1.67 |

SIGNAL FOR PACKAGING OF INFLUENZA VIRUS VECTOR

CROSS-REFERENCE TO RELATED APPLICATIONS

This application is a divisional of U.S. patent application Ser. No. 10/366,630, filed Feb. 12, 2003 now U.S. Pat. No. 7,226,774, which claims the benefit of the filing date of U.S. Provisional Application Ser. No. 60/356,538, filed on Feb. 13, 2002, and U.S. Provisional Application Ser. No. 60/438,679, filed on Jan. 7, 2003, under 35 U.S.C. § 119(e). The disclosure in those applications is incorporated by reference herein.

STATEMENT OF GOVERNMENT RIGHTS

The invention was made, at least in part, with a grant from the Government of the United States of America (grant A147446 from the National Institutes of Health). The government has certain rights in the invention.

BACKGROUND OF THE INVENTION

The genome of influenza A and B viruses is composed of eight single-strand RNA segments of negative polarity, two of which encode envelope glycoproteins, hemagglutinin (HA) and neuraminidase (NA). Replication of influenza virus is initiated by the binding of the viral HA proteins on the virion surface to cellular sialic acid containing receptors. After binding to the receptors, virions are taken into the host cells by endocytosis. The acidic environment in the late endosome triggers HA conformational changes, initiating fusion between the viral envelope and the endosomal membrane, and activates the M2 ion channel, resulting in proton influx into the virion interior. Exposure of the virion interior to low pH is thought to disrupt acid-labile interactions between the M1 protein and ribonucleoprotein complex (RNP), culminating in the release of RNP into the cytoplasm. The RNP is then transported to the nucleus, where viral mRNA and the viral genome are synthesized. mRNA enters the cytoplasm and viral proteins are synthesized. Nucleoprotein (NP) enters the nucleus and encapsidates newly synthesized vRNA and, together with the three polymerase subunit proteins (PA, PB1, PB2), forms RNP. In the presence of M1 and NS2 proteins, RNP is exported out of the nucleus. The three plasma membrane-associated proteins (HA, NA and M2) and RNP interact and form new virions by budding. NA is responsible for viral release from infected cells by removing sialic acids from cellular glycoconjugates and viral glycoproteins (Lamb et al., 2000).

Type A viruses are divided into subtypes based on HA (H1-H15) and NA (N1-N9) antigenicities. In cells infected with two different type A viruses, intratypic reassortants possessing various combinations of gene segments are produced (Wright et al., 2000). However, intertypic reassortants between type A and B viruses have not been detected in nature, although both viruses are cocirculating in human populations.

Investigators have attempted to generate reassortants between type A and B viruses in the laboratory without success (Kaverin et al, 1983; Mikheera et al., 1982; Tobita et al., 1983). Muster et al. (1991) generated a mutant type A virus containing a segment in which the noncoding regions of a NA segment were replaced with those of the nonstructural (NS) gene of type B virus. Although the mutant virus replicated more slowly and achieved lower titers than wild-type virus, the generation of such a virus suggested that the noncoding regions of the type B NS segment were compatible with influenza virus type A components at the level of RNA transcription and replication. By contrast, an RNA segment possessing a foreign coding segment flanked by the 3' and 5' noncoding regions of an influenza A viral RNA segment, was not stably maintained in virions after repeated passage (Luytjes et al., 1989). Muster et al. (1991) also disclose that the mutant virus was attenuated in mice, and that animals infected with the mutant virus were resistant to challenge with the wild-type virus.

What is needed is a method to identify influenza virus sequences for incorporation and/or maintenance of linked sequence during influenza virus replication.

SUMMARY OF THE INVENTION

The invention provides an isolated recombinant nucleic acid molecule (polynucleotide), e.g., a vector, comprising incorporation sequences (a "packaging signal" or a vRNA encapsidation signal) for influenza virus and optionally a heterologous nucleic acid segment. Generally, incorporation sequences are present in the about 150 to about 250 nucleotides at one or each end of the coding region for each influenza vRNA segment. In one embodiment, influenza virus incorporation sequences comprise sequences corresponding to the 3' end of NA vRNA including sequences corresponding to the N-terminus of the NA coding region, e.g., 37 nucleotides of the 3' end of type A NA vRNA including 19 nucleotides of 3' noncoding sequence and at least nucleotides corresponding to the first 19 coding nucleotides for NA and, optionally, incorporation sequences corresponding to the 5' end of NA vRNA including sequences corresponding to the C-terminus of the NA coding region, e.g., 67 nucleotides of the 5' end of type A NA vRNA including 28 nucleotides of 5' noncoding sequence and at least 39 nucleotides corresponding to the 39 3' coding nucleotides of NA. In another embodiment, influenza virus incorporation sequences comprise sequences corresponding to the 3' end of NS vRNA including sequences corresponding to the N-terminus of the NS coding region. In yet another embodiment, influenza virus incorporation sequences comprise sequences corresponding to the 5' end of HA vRNA including sequences corresponding to the C-terminus of the HA coding region, e.g., 135 nucleotides of the 5' end of type A HA vRNA including 45 nucleotides of 5' noncoding sequence and at least 80 nucleotides corresponding to the 80 3' coding nucleotides of HA and, optionally, incorporation sequences corresponding to the 3' end of HA vRNA, including sequences corresponding to the N-terminus of the HA coding region, e.g., 36 nucleotides of the 3' end of type A HA vRNA including 33 nucleotides of 3' noncoding sequence and at least 3 nucleotides corresponding to the first 3 coding nucleotides of HA. In a further embodiment, influenza virus incorporation sequences comprise sequences corresponding to the 5' end of PB2 vRNA including sequences corresponding to the C-terminus of the PB2 coding region. In another embodiment, influenza virus incorporation sequences comprise sequences corresponding to the 3' end of M vRNA including sequences corresponding to the N-terminus of the M coding region, e.g., 247 nucleotides of the 3' end of type A M vRNA including 26 nucleotides of 3' noncoding sequence and 221 nucleotides of sequence corresponding to the N-terminus of the M coding region, and sequences corresponding to the 5' end of M vRNA including incorporation sequences corresponding to the C-terminus of the M coding region, e.g., 242 nucleotides of the 5' end of type A M vRNA including 23 nucleotides of 3' noncoding sequence and 219 nucleotides of sequence corresponding to the last 219 nucleotide for the C-terminus of the M coding region. In another embodiment, influenza virus incorporation sequences comprise sequences corresponding to the 5' end of NS vRNA including sequences corresponding to the N-terminus of the NS coding region, e.g., sequences including the 3' noncoding sequence and at least the first 30 nucleotides corresponding to the N-terminus of the NS coding region, and sequences corresponding to the 5' end of NS vRNA including incorporation sequences corresponding to the C-terminus of the NS coding region, e.g., sequences including the 5' noncoding sequence and at least the last 30 nucleotides of sequence corresponding to the C-terminus of the NS coding region. In one embodiment, influenza virus incorporation sequences comprise sequences corresponding to the 5' end of PB1 vRNA including sequences corresponding to the N-terminus of the PB1 coding region and sequences corresponding to the 5' end of PB1 vRNA including incorporation sequences corresponding to the C-terminus of the PB1 coding region. In yet another embodiment, influenza virus incorporation sequences comprise sequences corresponding to the 5' end of PA vRNA including sequences corresponding to the N-terminus of the PA coding region and sequences corresponding to the 5' end of PA vRNA including incorporation sequences corresponding to the C-terminus of the PA coding region. Influenza virus "incorporation sequences," as used herein, are sequences which, when present in vRNA with corresponding (homologous) 3' and 5' noncoding regions, result in the incorporation of a nucleic acid molecule comprising those sequences into virions and the maintenance of that molecule in virions during repeated passage.

As described hereinbelow, NA incorporation sequences were identified in mutant viruses with a truncated NA segment using plasmid-based reverse genetics. The NA incorporation sequences were in a region which included the 3' end of NA vRNA, which extended into a portion of the NA coding region. Thus, this region is useful for packaging and maintenance of wild-type NA RNA as well as mutant NA RNAs, e.g., RNAs with internal deletions and/or insertions including recombinant RNAs for expression of open reading frames of interest, e.g., a heterologous nucleic acid segment comprising an open reading frame of interest.

As also described herein, to gain insight into intertypic incompatibility between influenza type A and B viruses, reverse genetics was employed to generate a reassortant containing an intact type B HA segment in a type A virus background. However, no virus was produced, despite the fact that the type B HA segment was transcribed by the type A polymerase complex. Although a type A virus with a chimeric HA segment composed of the entire coding sequence of type B HA flanked by the noncoding sequence of type A HA was viable, it replicated only marginally. A series of type A-based viruses was generated containing chimeric HAs possessing the type A noncoding region together with either the sequence encoding the signal peptide or transmembrane/cytoplasmic region of type A virus, or both, and the rest of the region derived from type B HA. All of these viruses grew to more than $10^6$ tissue culture infectious dose$_{50}$/ml in cell culture, however, the viruses with more of the type A HA sequences replicated better, suggesting the role of protein-protein interaction or increased HA segment incorporation into virions in efficient viral growth. All of these A/B chimeric viruses were attenuated in mice as compared with wild-type A or B viruses. Moreover, all animals intranasally immunized with the chimeric viruses survived upon challenge with a lethal dose of wild-type type B virus, demonstrating a promising approach for the design of a novel live vaccine virus.

Thus, when an isolated nucleic acid molecule of the invention comprising incorporation sequences for a particular influenza virus segment, the homologous 3' and 5' noncoding sequences (regions) and a heterologous nucleic acid segment, is introduced to a cell in a vector for vRNA production and in the presence of viral proteins and/or viral protein coding vectors for one or more of PA, PB1, PB2, NP, HA, NA, M, e.g., M1 and/or M2, and/or NS, and vRNAs or vectors for vRNA production for one or more of PA, PB1, PB2, NP, HA, NA, M, e.g., M1 and M2, and/or NS, recombinant virus is produced. The recombinant virus may then be used to infect a cell. Preferably, vRNA corresponding to a nucleic acid molecule of the invention is incorporated into virions at an efficiency that is at least 10%, more preferably at least 30%, and even more preferably at least 50% or more, that of a corresponding wild-type vRNA. In one embodiment, the nucleic acid molecule includes sequences corresponding to a wild-type vRNA and a heterologous nucleic acid segment, wherein the heterologous nucleic acid segment is introduced to sequences in the vRNA corresponding to the coding region for that vRNA, which insertion preferably does not substantially disrupt the incorporation sequences. For instance, the heterologous nucleic acid segment is introduced after a sequence corresponding to the first 300 nucleotides of the NA coding region.

In another embodiment, the 3' NA incorporation sequences correspond to nucleotides 1 to 183, nucleotides 1 to 90, nucleotides 1 to 45, nucleotides 1 to 21, nucleotides 1 to 19 or any integer between 19 and 183, of the N-terminal NA coding region, and may include a mutation at the NA initiation codon. In another embodiment, the 5' NA incorporation sequences correspond to sequences in the C-terminal coding region of NA, sequences corresponding to the 3' most 39, 78, or 157, or any integer between 1 and 157, nucleotides for C-terminal NA coding region. In another embodiment, the 5' HA incorporation sequences correspond to sequences in the C-terminal coding region of HA, sequences corresponding to the 3' most 75, 80, 268, 291, or 518, or any integer between 1 and 518, nucleotides of the C-terminal HA coding region. The 3' HA incorporation sequences correspond to nucleotides 1 to 3, 1 to 6, 1 to 9, 1 to 15, 1 to 216, 1 to 468, or any integer between 1 and 468, of the N-terminal HA coding region. In one embodiment, the 3' PB1 incorporation sequences correspond to nucleotides 1 to 250, nucleotides 1 to 200, nucleotides 1 to 150, or any integer between 1 and 250, of the N-terminal PB1 coding region. In one embodiment, the 5' PB1 incorporation sequences correspond to the 3' most nucleotides, e.g., the 3' 1 to 250 nucleotides, 1 to 200 nucleotides, nucleotides 1 to 150, or any integer between 1 and 250, of the C-terminal PB1 coding region. In one embodiment, the 3' PA incorporation sequences correspond to nucleotides 1 to 250, nucleotides 1 to 200, nucleotides 1 to 150, or any integer between 1 and 250, of the N-terminal PA coding region. In one embodiment, the 5' PA incorporation sequences correspond to the 3' most nucleotides, e.g., the 3' 1 to 250 nucleotides, 1 to 200 nucleotides, nucleotides 1 to 150, or any integer between 1 and 250, of the C-terminal PA coding region. In another embodiment, the 3' M incorporation sequences correspond to nucleotides 1 to 250, nucleotides 1 to 242, nucleotides 1 to 240, or any integer between 1 and 250, of the N-terminal M coding region, and may include a mutation at the M initiation codon. In another embodiment, the 5' M incorporation sequences correspond to sequences in the C-terminal coding region of M, sequences corresponding to the 3' most 50, 100, or 220, or any integer between 1 and 250, nucleotides for C-terminal M coding region. In another embodiment, the 3' NS incorporation sequences correspond to nucleotides 1 to 250, nucleotides 1 to 200, nucleotides 1 to 150, nucleotides 1 to 30, nucleotides 1 to 20 or any integer between 1 and 250, of the N-terminal NS coding region, and may include a mutation at the NS initiation codon. In another embodiment, the 5' NS incorporation sequences correspond to sequences in the C-terminal coding region of NS, sequences corresponding to the 3' most 10, 30, 150, 200 or 250, or any integer between 1 and 250, nucleotides for the C-terminal NS coding region.

Accordingly, the invention provides influenza virus vectors which include sequences corresponding to the 3' and 5' noncoding regions of a particular vRNA, incorporation sequences of the corresponding vRNA, and a heterologous nucleic acid segment. Thus, in one embodiment, the vector includes the 3' noncoding region of NA vRNA, 3' or 5' NA vRNA incorporation sequences, and optionally both 3' and 5' NA incorporation sequences, a heterologous nucleic acid segment, and the 5' noncoding region of NA vRNA. In another embodiment, the vector includes the 3' noncoding region of HA vRNA, 5' or 3' HA vRNA incorporation sequences or both 5' and 3' HA incorporation sequences, a heterologous nucleic acid segment, and the 5' noncoding region of HA vRNA. In another embodiment, the vector includes the 3' noncoding region of NS vRNA, NS incorporation sequences, a heterologous nucleic acid segment, and the 5' noncoding region of NS vRNA. In another embodiment, the vector includes the 3' noncoding region of M vRNA, 5' or 3' M incorporation sequences or both 5' and 3' M incorporation sequences, a heterologous nucleic acid segment, and the 5' noncoding region of M vRNA. In yet another embodiment, the vector includes the 3' noncoding region of PB2 vRNA, a heterologous nucleic acid segment, PB2 incorporation sequences, and the 5' noncoding region of PB2 vRNA. When two incorporation sequences are employed in a vector, they preferably are separated by the heterologous nucleic acid segment. Each vector may be employed so as to prepare vRNA for introduction to a cell, or to express vRNA in a cell, in which other influenza virus vRNAs and proteins necessary for virus production, are present.

In one embodiment, the heterologous nucleic acid segment comprises sequences corresponding to an open reading frame for a marker gene. In another embodiment, the heterologous nucleic acid segment comprises sequences corresponding to an open reading frame for a therapeutic gene. In yet a further embodiment, the heterologous nucleic acid segment comprises sequences corresponding to an open reading frame for an immunogenic peptide or protein of a pathogen or a tumor cell, e.g., one useful to induce a protective immune response. For example, the heterologous nucleic acid segment may encode an immunogenic epitope useful in cancer therapy or a vaccine. The vector comprising the heterologous nucleic acid segment may be prepared such that transcription of vector vRNA results in mRNA encoding a fusion protein with an influenza protein such as NA. Thus, it is envisioned that the heterologous nucleic acid segment may be fused with viral incorporation sequences so as to encode a fusion protein, e.g., a fusion with the N-terminal 21 residues of NA. The fusion protein may comprise sequences from two different influenza virus proteins including sequences from two different NA or HA proteins. In another embodiment, the heterologous nucleic acid segment may comprise sequences corresponding to an IRES linked 5' to an open reading frame.

To prepare recombinant virus using plasmid-based reverse genetics with a plurality of influenza virus vectors, the influenza virus DNA in a vector may be in the sense or antisense orientation relative to the promoter. Thus, a vector may encode an influenza virus protein (sense), or vRNA (antisense) of an influenza virus A, B, or C, strain or isolate, or a recombinant influenza virus (see Chapters 45 and 46 of Fields *Virology* (Fields et al. (eds.), Lippincott-Raven Publ., Philadelphia, Pa. (1996), which are specifically incorporated by reference herein). Any promoter may be employed to express a viral protein and the resulting vector includes a promoter operably linked to a DNA for a particular influenza virus protein. Preferred promoters for the vectors encoding vRNA include, but are not limited to, a RNA polymerase I promoter, a RNA polymerase II promoter, a RNA polymerase III promoter, a T7 promoter, and a T3 promoter. In one embodiment, the RNA polymerase I promoter is a human RNA polymerase I promoter. Preferred transcription termination sequences for the vectors encoding vRNA include, but are not limited to, a RNA polymerase I transcription termination sequence, a RNA polymerase II transcription termination sequence, or a RNA polymerase III transcription termination sequence, or a ribozyme. Thus, a vector for vRNA includes a promoter operably linked to a cDNA for an influenza virus protein in antisense orientation relative to the promoter, which is operably linked to a transcription termination sequence. To produce recombinant virus with a vector of the invention, certain wild-type vRNA vectors may be omitted and certain wild-type viral protein coding vectors may be replaced. For instance, for a vRNA vector comprising HA 3' and 5' noncoding sequences, 5' HA incorporation sequences and a heterologous nucleic acid segment corresponding to a noninfluenza virus protein coding sequence, e.g., VSV G protein coding sequence, the HA wild-type vRNA vector may be omitted. The vectors of the invention may be introduced to a cell sequentially or simultaneously. Also provided is a composition comprising a plurality of the above-mentioned vectors, a host cell contacted with one or more of the vectors, virus prepared by the method, and a cell infected with the virus.

A plurality of the vectors of the invention may be physically linked or each vector may be present on an individual plasmid or other, e.g., linear, nucleic acid delivery vehicle.

Host cells augmented with recombinant DNA molecules as described hereinabove are useful to prepare infectious replication defective influenza virus. For example, a host cell stably transformed with recombinant DNA molecules encoding HA, NA, M1, M2 and NS2 may be contacted with a plurality of vectors, i.e., vectors which express vRNA comprising PA, vRNA comprising NP, vRNA comprising PB1, vRNA comprising PB2, and optionally, vRNA comprising a gene of interest; and vectors which encode PA, PB1, PB2, and NP.

The methods of producing virus described herein, which do not require helper virus infection, are useful in viral mutagenesis studies, and in the production of vaccines (e.g., for AIDS, influenza, hepatitis B, hepatitis C, rhinovirus, filoviruses, malaria, herpes, and foot and mouth disease) and gene therapy vectors (e.g., for cancer, AIDS, adenosine deaminase, muscular dystrophy, ornithine transcarbamylase deficiency and central nervous system tumors).

Thus, a recombinant virus for use in medical therapy (e.g., for a vaccine or gene therapy) is provided. For example, the invention provides a method to immunize an individual against a pathogen, e.g., a bacteria, virus, or parasite, or a malignant tumor. The method comprises administering to the individual an amount of at least one isolated virus of the invention, optionally in combination with an adjuvant, effective to immunize the individual. The virus comprises vRNA comprising a polypeptide encoded by the pathogen or a tumor specific polypeptide.

Also provided is a method to augment or increase the expression of an endogenous protein in a mammal having an indication or disease characterized by a decreased amount or a lack of the endogenous protein. The method comprises administering to the mammal an amount of a recombinant virus of the invention effective to augment or increase the amount of the endogenous protein in the mammal. Preferably, the mammal is a human.

Further provided is a method to inhibit influenza virus infection and/or replication. The method comprises contacting a cell with a composition comprising an isolated nucleic acid molecule comprising influenza virus incorporation sequences for NA, M, HA, NS, NP, PB1, PB2, PA, or any combination of such molecules, in an amount effective to inhibit influenza virus infection and/or replication. The cell may be an uninfected cell or one which is infected with influenza virus. The incorporation sequences may be specific for one or more types of NA or HA. In one embodiment, the cell is further contacted with a M2 channel inhibitor or a neuraminidase inhibitor.

Also provided is a method to identify an agent which specifically inhibits or prevents incorporation of influenza virus RNA into virions. The method comprises contacting a cell infected with influenza virus with an agent; and detecting or determining whether the agent specifically inhibits or prevents incorporation of influenza virus RNA, such as NA vRNA or recombinant NA vRNA, into virions. Agents identified by the method, and uses thereof, e.g., to inhibit or prevent influenza virus replication, are also provided.

DETAILED DESCRIPTION OF THE INVENTION

Figure 1A:
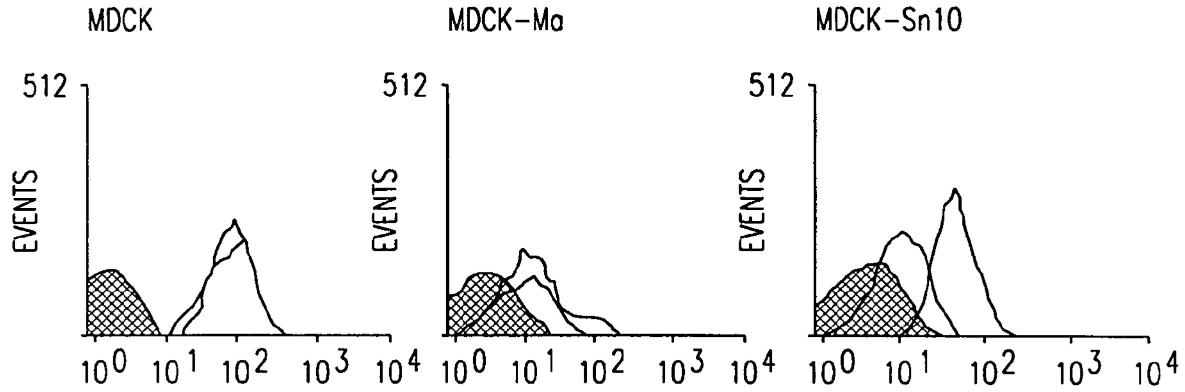
FIG. 1. Binding of lectin-resistant cell lines. For each cell line, cells were incubated with digoxigenin-labeled *Maakia amurensis* (MAA) or *Sambucus nigra* (SNA) lectins, followed by fluorescein isothiocyanate-labeled antidigoxigenin antibody, and then analyzed by FACS. Bold lines, binding of the MAA lectin; narrow lines, binding of the SNA lectin; shaded profiles, negative control (no lectin added).

As used herein, the terms “isolated and/or purified” refer to in vitro preparation, isolation and/or purification of a host cell or virus of the invention, so that it is not associated with in vivo substances, or is substantially purified from in vitro substances. As used herein, “substantially pure” means an object species is the predominant species present (i.e., on a molar basis it is more abundant than any other individual species in the composition), and preferably a substantially purified fraction is a composition wherein the object species comprises at least about 50 percent (on a molar basis) of all macromolecular species present. Generally, a substantially pure composition will comprise more than about 50 percent, more preferably more than about 80 percent of all macromolecular species present in the composition, and even more preferably more than about 85%, about 90%, about 95%, and about 99%. Most preferably, the object species is purified to essential homogeneity (contaminant species cannot be detected in the composition by conventional detection methods).

As used herein, the term “recombinant nucleic acid” or “recombinant DNA sequence or segment” refers to a nucleic acid, e.g., to DNA, that has been derived or isolated from a source, that may be subsequently chemically altered in vitro, so that its sequence is not naturally occurring, or corresponds to naturally occurring sequences that are not positioned as they would be positioned in the native genome. An example of DNA “derived” from a source, would be a DNA sequence that is identified as a useful fragment, or reverse transcribed from RNA, and which is then synthesized in essentially pure form. An example of such DNA “isolated” from a source would be a useful DNA sequence that is excised or removed from said source by chemical means, e.g., by the use of restriction endonucleases, so that it can be further manipulated, e.g., amplified, for use in the invention, by the methodology of genetic engineering. Recombinant virus is prepared from recombinant nucleic acid.

As used herein, a “heterologous” nucleic acid segment, sequence or molecule means that the segment, sequence or molecule is derived from a source that is different than a reference nucleic acid segment, sequence or molecule. For example, a type A influenza virus segment or a portion thereof is heterologous to the corresponding type B influenza virus segment or a portion thereof, a NA viral segment of one influenza strain or serotype is heterologous to a NA viral segment of a different strain or serotype, and a non-influenza virus nucleic acid molecule, e.g., HIV gp160, is heterologous to an influenza virus nucleic acid molecule. In contrast, a homologous nucleic acid segment is derived from the same source as a reference nucleic acid segment. Thus, the nucleic acid molecule of the invention is a chimeric molecule which includes a 3' noncoding region, at least one incorporation sequence and a 5' noncoding sequence which are homologous to each other.

The phrase “efficient replication” in the context of the present invention, is defined as producing high infectivity titers in in vitro tissue culture systems, such as $10^4$-$10^{10}$ PFU/ml, and preferably $10^6$-$10^9$ PFU/ml. The screening of influenza viruses for use in replication or vaccine production, can be assayed using any known and/or suitable assay, as is known in the art. Such assays (alone or in any combination) that are suitable for screening include, but are not limited to, viral replication, quantitative and/or qualitative measurement of inactivation (e.g., by antisera), transcription, replication, translation, virion incorporation, virulence, HA or NA activity, viral yield, and/or morphogenesis, using such methods as reverse genetics, reassortment, complementation, and/or infection. For example, virus replication assays can be used to screen for attenuation or inactivation of the virus. See, e.g., Krug, R. M., ed., The Influenza Viruses, Plenum Press, New York, (1989).

“Sialic acid” refers to a family of amino sugars containing 9 or more carbon atoms, e.g., N- and O-substituted derivatives of neuraminic acid.

As used herein, “site-specific recombination” is intended to include the following three events: 1) deletion of a target DNA segment flanked by site-specific recombination sites or sequences, e.g., lox sites; 2) inversion of the nucleotide sequence of a target DNA segment flanked by site-specific recombination sites or sequences, e.g., lox sites; and 3) reciprocal exchange of target DNA segments proximate to site-specific recombination sites or sequences, e.g., lox sites located on different DNA molecules. Site-specific recombinase systems include, but are not limited to, the Cre/lox system of bacteriophage P1 (U.S. Pat. No. 5,658,772), the FLP/FRT system of yeast (Golic and Lindquist, 1989), the Gin recombinase of Mu (Maeser et al., 1991), the Pin recombinase of *E. coli* (Enomoto et al., 1983), and the R/RS system of the pSR1 plasmid (Araki et al., 1992).

Cell Lines and Influenza Viruses That Can Be Used in the Present Invention

According to the present invention, any cell which supports efficient replication of influenza virus can be employed in the invention, including mutant cells which express reduced or decreased levels of one or more sialic acids which are receptors for influenza virus. Viruses obtained by the methods can be made into a reassortant virus.

Preferably, the cells are WHO certified, or certifiable, continuous cell lines. The requirements for certifying such cell lines include characterization with respect to at least one of genealogy, growth characteristics, immunological markers, virus susceptibility tumorigenicity and storage conditions, as well as by testing in animals, eggs, and cell culture. Such characterization is used to confirm that the cells are free from detectable adventitious agents. In some countries, karyology may also be required. In addition, tumorigenicity is preferably tested in cells that are at the same passage level as those used for vaccine production. The virus is preferably purified by a process that has been shown to give consistent results, before being inactivated or attenuated for vaccine production (see, e.g., World Health Organization, 1982).

It is preferred to establish a complete characterization of the cell lines to be used, so that appropriate tests for purity of the final product can be included. Data that can be used for the characterization of a cell to be used in the present invention includes (a) information on its origin, derivation, and passage history; (b) information on its growth and morphological characteristics; (c) results of tests of adventitious agents; (d) distinguishing features, such as biochemical, immunological, and cytogenetic patterns which allow the cells to be clearly recognized among other cell lines; and (e) results of tests for tumorigenicity. Preferably, the passage level, or population doubling, of the host cell used is as low as possible.

It is preferred that the virus produced in the cell is highly purified prior to vaccine or gene therapy formulation. Generally, the purification procedures will result in the extensive removal of cellular DNA, other cellular components, and adventitious agents. Procedures that extensively degrade or denature DNA can also be used. See, e.g., Mizrahi, 1990.

Vaccines

A vaccine of the invention may comprise immunogenic proteins including glycoproteins of any pathogen, e.g., an immunogenic protein from one or more bacteria, viruses, yeast or fungi. Thus, in one embodiment, the influenza viruses of the invention may be vaccine vectors for influenza virus or other viral pathogens including but not limited to lentiviruses such as HIV, hepatitis B virus, hepatitis C virus, herpes viruses such as CMV or HSV or foot and mouth disease virus.

A complete virion vaccine is concentrated by ultrafiltration and then purified by zonal centrifugation or by chromatography. It is inactivated before or after purification using formalin or beta-propiolactone, for instance.

A subunit vaccine comprises purified glycoproteins. Such a vaccine may be prepared as follows: using viral suspensions fragmented by treatment with detergent, the surface antigens are purified, by ultracentrifugation for example. The subunit vaccines thus contain mainly HA protein, and also NA. The detergent used may be cationic detergent for example, such as hexadecyl trimethyl ammonium bromide (Bachmeyer, 1975), an anionic detergent such as ammonium deoxycholate (Layer & Webster, 1976); Webster et al., 1977); or a nonionic detergent such as that commercialized under the name TRITON X100. The hemagglutinin may also be isolated after treatment of the virions with a protease such as bromelin, then purified by a method such as that described by Grand and Skehel (1972).

A split vaccine comprises virions which have been subjected to treatment with agents that dissolve lipids. A split vaccine can be prepared as follows: an aqueous suspension of the purified virus obtained as above, inactivated or not, is treated, under stirring, by lipid solvents such as ethyl ether or chloroform, associated with detergents. The dissolution of the viral envelope lipids results in fragmentation of the viral particles. The aqueous phase is recuperated containing the split vaccine, constituted mainly of hemagglutinin and neuraminidase with their original lipid environment removed, and the core or its degradation products. Then the residual infectious particles are inactivated if this has not already been done.

Inactivated Vaccines. Inactivated influenza virus vaccines of the invention are provided by inactivating replicated virus of the invention using known methods, such as, but not limited to, formalin or β-propiolactone treatment. Inactivated vaccine types that can be used in the invention can include whole-virus (WV) vaccines or subvirion (SV) (split) vaccines. The WV vaccine contains intact, inactivated virus, while the SV vaccine contains purified virus disrupted with detergents that solubilize the lipid-containing viral envelope, followed by chemical inactivation of residual virus.

In addition, vaccines that can be used include those containing the isolated HA and NA surface proteins, which are referred to as surface antigen or subunit vaccines. In general, the responses to SV and surface antigen (i.e., purified HA or NA) vaccines are similar. An experimental inactivated WV vaccine containing an NA antigen immunologically related to the epidemic virus and an unrelated HA appears to be less effective than conventional vaccines (Ogra et al., 1977). Inactivated vaccines containing both relevant surface antigens are preferred.

Live Attenuated Virus Vaccines. Live, attenuated influenza virus vaccines, can also be used for preventing or treating influenza virus infection, according to known method steps. Attenuation is preferably achieved in a single step by transfer of attenuated genes from an attenuated donor virus to a replicated isolate or reassorted virus according to known methods (see, e.g., Murphy, 1993). Since resistance to influenza A virus is mediated by the development of an immune response to the HA and NA glycoproteins, the genes coding for these surface antigens must come from the reassorted viruses or high growth clinical isolates. The attenuated genes are derived from the attenuated parent. In this approach, genes that confer attenuation preferably do not code for the HA and NA glycoproteins. Otherwise, these genes could not be transferred to reassortants bearing the surface antigens of the clinical virus isolate.

Many donor viruses have been evaluated for their ability to reproducibly attenuate influenza viruses. As a non-limiting example, the A/Ann Arbor(AA)/6/60 ($H_2N_2$) cold adapted (ca) donor virus can be used for attenuated vaccine production (see, e.g., Edwards, 1994; Murphy, 1993). Additionally, live, attenuated reassortant virus vaccines can be generated by mating the ca donor virus with a virulent replicated virus of the invention. Reassortant progeny are then selected at 25° C., (restrictive for replication of virulent virus), in the presence of an $H_2N_2$ antiserum, which inhibits replication of the viruses bearing the surface antigens of the attenuated A/AA/6/60 ($H_2N_2$) ca donor virus.

A large series of H1N1 and $H_3N_2$ reassortants have been evaluated in humans and found to be satisfactorily: (a) infectious, (b) attenuated for seronegative children and immunologically primed adults, (c) immunogenic and (d) genetically stable. The immunogenicity of the ca reassortants parallels their level of replication. Thus, the acquisition of the six transferable genes of the ca donor virus by new wild-type viruses has reproducibly attenuated these viruses for use in vaccinating susceptible adults and children.

Other attenuating mutations can be introduced into influenza virus genes by site-directed mutagenesis to rescue infectious viruses bearing these mutant genes. Attenuating mutations can be introduced into non-coding regions of the genome, as well as into coding regions. Such attenuating mutations can also be introduced into genes other than the HA or NA, e.g., the PB2 polymerase gene (Subbarao et al., 1993). Thus, new donor viruses can also be generated bearing attenuating mutations introduced by site-directed mutagenesis, and such new donor viruses can be used in the reduction of live attenuated reassortants H1N1 and $H_3N_2$ vaccine candidates in a manner analogous to that described above for the A/AA/6/60 ca donor virus. Similarly, other known and suitable attenuated donor strains can be reasserted with influenza virus of the invention to obtain attenuated vaccines suitable for use in the vaccination of mammals (Ewami et al., 1990; Muster et al., 1991; Subbarao et al., 1993).

It is preferred that such attenuated viruses maintain the genes from the virus that encode antigenic determinants substantially similar to those of the original clinical isolates. This is because the purpose of the attenuated vaccine is to provide substantially the same antigenicity as the original clinical isolate of the virus, while at the same time lacking infectivity to the degree that the vaccine causes minimal change of inducing a serious pathogenic condition in the vaccinated mammal.

The virus can thus be attenuated or inactivated, formulated and administered, according to known methods, as a vaccine to induce an immune response in an animal, e.g., a mammal. Methods are well-known in the art for determining whether such attenuated or inactivated vaccines have maintained similar antigenicity to that of the clinical isolate or high growth strain derived therefrom. Such known methods include the use of antisera or antibodies to eliminate viruses expressing antigenic determinants of the donor virus; chemical selection (e.g., amantadine or rimantidine); HA and NA activity and inhibition; and DNA screening (such as probe hybridization or PCR) to confirm that donor genes encoding the antigenic determinants (e.g., HA or NA genes) are not present in the attenuated viruses. See, e.g., Robertson et al., 1988; Kilbourne, 1969; Aymard-Henry et al., 1985; Robertson et al., 1992.

Pharmaceutical Compositions

Pharmaceutical compositions of the present invention, suitable for inoculation or for parenteral or oral administration, comprise attenuated or inactivated influenza viruses, optionally further comprising sterile aqueous or non-aqueous solutions, suspensions, and emulsions. The compositions can further comprise auxiliary agents or excipients, as known in the art. See, e.g., Berkow et al., 1987; Goodman et al., 1990; *Avery's Drug Treatment,* 1987; Osol, 1980; Katzung, 1992. The composition of the invention is generally presented in the form of individual doses (unit doses).

Conventional vaccines generally contain about 0.1 to 200 μg, preferably 10 to 15 μg, of hemagglutinin from each of the strains entering into their composition. The vaccine forming the main constituent of the vaccine composition of the invention may comprise a virus of type A, B or C, or any combination thereof, for example, at least two of the three types, at least two of different subtypes, at least two of the same type, at least two of the same subtype, or a different isolate(s) or reassortant(s). Human influenza virus type A includes H1N1, $H_2N_2$ and $H_3N_2$ subtypes.

Preparations for parenteral administration include sterile aqueous or non-aqueous solutions, suspensions, and/or emulsions, which may contain auxiliary agents or excipients known in the art. Examples of non-aqueous solvents are propylene glycol, polyethylene glycol, vegetable oils such as olive oil, and injectable organic esters such as ethyl oleate. Carriers or occlusive dressings can be used to increase skin permeability and enhance antigen absorption. Liquid dosage forms for oral administration may generally comprise a liposome solution containing the liquid dosage form. Suitable forms for suspending liposomes include emulsions, suspensions, solutions, syrups, and elixirs containing inert diluents commonly used in the art, such as purified water. Besides the inert diluents, such compositions can also include adjuvants, wetting agents, emulsifying and suspending agents, or sweetening, flavoring, or perfuming agents. See, e.g., Berkow et al., 1992; Goodman et al., 1990; Avery's, 1987; Osol, 1980; and Katzung, 1992.

When a composition of the present invention is used for administration to an individual, it can further comprise salts, buffers, adjuvants, or other substances which are desirable for improving the efficacy of the composition. For vaccines, adjuvants, substances which can augment a specific immune response, can be used. Normally, the adjuvant and the composition are mixed prior to presentation to the immune system, or presented separately, but into the same site of the organism being immunized. Examples of materials suitable for use in vaccine compositions are provided in Osol (1980).

Heterogeneity in a vaccine may be provided by mixing replicated influenza viruses for at least two influenza virus strains, such as 2-50 strains or any range or value therein. Influenza A or B virus strains having a modern antigenic composition are preferred. According to the present invention, vaccines can be provided for variations in a single strain of an influenza virus, using techniques known in the art.

A pharmaceutical composition according to the present invention may further or additionally comprise at least one chemotherapeutic compound, for example, for gene therapy, immunosuppressants, anti-inflammatory agents or immune enhancers, and for vaccines, chemotherapeutics including, but not limited to, gamma globulin, amantadine, guanidine, hydroxybenzimidazole, interferon-α, interferon-β, interferon-γ, tumor necrosis factor-alpha, thiosemicarbarzones, methisazone, rifampin, ribavirin, a pyrimidine analog, a purine analog, foscamet, phosphonoacetic acid, acyclovir, dideoxynucleosides, a protease inhibitor, or ganciclovir. See, e.g., Katzung (1992), and the references cited therein on pages 798-800 and 680-681, respectively.

The composition can also contain variable but small quantities of endotoxin-free formaldehyde, and preservatives, which have been found safe and not contributing to undesirable effects in the organism to which the composition is administered.

Pharmaceutical Purposes

The administration of the composition (or the antisera that it elicits) may be for either a "prophylactic" or "therapeutic" purpose. When provided prophylactically, the compositions of the inventions which are vaccines, are provided before any symptom of a pathogen infection becomes manifest. The prophylactic administration of the composition serves to prevent or attenuate any subsequent infection. When provided therapeutically, the attenuated or inactivated viral vaccine is provided upon the detection of a symptom of actual infection.

The therapeutic administration of the compound(s) serves to attenuate any actual infection. See, e.g., Berkow et al., 1992; Goodman et al., 1990; Avery, 1987; and Katzung, 1992.

An attenuated or inactivated vaccine composition of the present invention may thus be provided either before the onset of infection (so as to prevent or attenuate an anticipated infection) or after the initiation of an actual infection.

Similarly, for gene therapy, the composition may be provided before any symptom of a disorder or disease is manifested or after one or more symptoms are detected.

A composition is said to be "pharmacologically acceptable" if its administration can be tolerated by a recipient patient. Such an agent is said to be administered in a "therapeutically effective amount" if the amount administered is physiologically significant. A composition of the present invention is physiologically significant if its presence results in a detectable change in the physiology of a recipient patient, e.g., enhances at least one primary or secondary humoral or cellular immune response against at least one strain of an infectious influenza virus.

The "protection" provided need not be absolute, i.e., the influenza infection need not be totally prevented or eradicated, if there is a statistically significant improvement compared with a control population or set of patients. Protection may be limited to mitigating the severity or rapidity of onset of symptoms of the influenza virus infection.

Pharmaceutical Administration

A composition of the present invention may confer resistance to one or more pathogens, e.g., one or more influenza virus strains, by either passive immunization or active immunization. In active immunization, an inactivated or attenuated live vaccine composition is administered prophylactically to a host (e.g., a mammal), and the host's immune response to the administration protects against infection and/or disease. For passive immunization, the elicited antisera can be recovered and administered to a recipient suspected of having an infection caused by at least one influenza virus strain.

In a second embodiment, the vaccine is provided to a mammalian female (at or prior to pregnancy or parturition), under conditions of time and amount sufficient to cause the production of an immune response which serves to protect both the female and the fetus or newborn (via passive incorporation of the antibodies across the placenta or in the mother's milk).

The present invention thus includes methods for preventing or attenuating a disorder or disease, e.g., an infection by at least one strain of pathogen. As used herein, a vaccine is said to prevent or attenuate a disease if its administration results either in the total or partial attenuation (i.e., suppression) of a symptom or condition of the disease, or in the total or partial immunity of the individual to the disease.

At least one inactivated or attenuated influenza virus, or composition thereof, of the present invention may be administered by any means that achieve the intended purposes, using a pharmaceutical composition as previously described.

For example, administration of such a composition may be by various parenteral routes such as subcutaneous, intravenous, intradermal, intramuscular, intraperitoneal, intranasal, oral or transdermal routes. Parenteral administration can be by bolus injection or by gradual perfusion over time. A preferred mode of using a pharmaceutical composition of the present invention is by intramuscular or subcutaneous application. See, e.g., Berkow et al., 1992; Goodman et al., 1990; Avery, 1987; and Katzung, 1992.

A typical regimen for preventing, suppressing, or treating an influenza virus related pathology, comprises administration of an effective amount of a vaccine composition as described herein, administered as a single treatment, or repeated as enhancing or booster dosages, over a period up to and including between one week and about 24 months, or any range or value therein.

According to the present invention, an "effective amount" of a vaccine composition is one that is sufficient to achieve a desired biological effect. It is understood that the effective dosage will be dependent upon the age, sex, health, and weight of the recipient, kind of concurrent treatment, if any, frequency of treatment, and the nature of the effect wanted. The ranges of effective doses provided below are not intended to limit the invention and represent preferred dose ranges. However, the most preferred dosage will be tailored to the individual subject, as is understood and determinable by one of skill in the art. See, e.g., Berkow et al., 1992; Goodman et al., 1990; Avery's, 1987; Ebadi, 1985; and Katsung, 1992.

The dosage of an attenuated virus vaccine for a mammalian (e.g., human) or avian adult organism can be from about $10^3$-$10^7$ plaque forming units (PFU)/kg, or any range or value therein. The dose of inactivated vaccine can range from about 0.1 to 200, e.g., 50 μg of hemagglutinin protein. However, the dosage should be a safe and effective amount as determined by conventional methods, using existing vaccines as a starting point.

The dosage of immunoreactive HA in each dose of replicated virus vaccine can be standardized to contain a suitable amount, e.g., 1-50 μg or any range or value therein, or the amount recommended by the U.S. Public Heath Service (PHS), which is usually 15 μg, per component for older children ≧3 years of age, and 7.5 μg per component for older children <3 years of age. The quantity of NA can also be standardized, however, this glycoprotein can be labile during the processor purification and storage (Kendal et al., 1980; Kerr et al., 1975). Each 0.5-ml dose of vaccine preferably contains approximately 1-50 billion virus particles, and preferably 10 billion particles.

The invention will be further described by the following non-limiting examples.

EXAMPLE 1

Materials and Methods

Viruses and cells. Human $H_3N_2$ viruses isolated from a single patient, either in embryonated chicken eggs (A/Tottori/AT1/AM2AL3/94; AM1AL3) of Madin-Darby canine kidney (MDCK) cells (A/Tottori/872/K4/94; K4), were obtained from T. Ito (Tottori University, Tottori, Japan). Virus stocks were grown either in 10 day-old embryonated chicken eggs (AMZAL3 virus) or on MDCK cells (K4 virus) in minimal essential medium (MEM) supplemented with 0.3% bovine serum albumin and 0.5 mg of trypsin/ml. MDCK cells were maintained in MEM supplemented with 5% newborn calf serum (Sigma, St. Louis, Mo.).

Generation of lectin-resistant cell lines. MDCK cells grown to 75% confluency were washed three times with phosphate-buffered saline and incubated with *Maakia amurensis* (MAA) lectin (100 mg/ml; Boehringer Mannheim, Mannheim, Germany) or *Sambucus nigra* (SNA) lectin (100 mg/ml; Boehringer Mannheim) in MEM containing 0.3% bovine serum albumin. After a 48 hour incubation, the medium was replaced with growth medium (MEM-5% fetal calf serum). Lectin selection was repeated as above two additional times. Surviving cell colonies were then cloned, and the SNA- and MAA-selected cell lines were designated MDCK-Sn10 and MDCK-Ma, respectively.

Fluorometric HPLC method for determination of sialic acid content. The sialic acid (N-acetylneuraminic acid [NeuAc] and N-glycolylneuraminic acid [NeuGc]) content of both cell lines and the purified virus was determined fluorometrically by high-performance liquid chromatography as described in Suzuki et al. (1997). Each sample was placed in a 5-ml ground glass-topped vial and mixed with 100 μl (25 mM) of sulfuric acid. The vials were then heated at 60° C. for 12 hours to hydrolize sialo-sugar chains. After cooling, 50 μl of 1,2-diamino-4,5-methylene dioxybenzene was added to 50 μl of the hydrolyte, and the mixture was heated to 60° C. for 2.5 hours in the dark to develop the fluorescence of the sialic acid. A 10 μl aliquot of the resulting solution was then injected into an 880-PU high performance liquid chromatograph (JASCO, Tokyo Japan) equipped with a sample injector valve (model 7125; Reodyne) and a fluorescent spectrophotometer (650-105; Hirachi, Tokyo, Japan) with a 20-μl flow cell and a recorder (Chromatopac C-RSA; Shionadzu, Kyoto, Japan). The fluorescence spectrophotometer was positioned at an excitation wavelength of 373 nm and an emission wavelength of 448 nm. Standard mixtures (200 pmol/μl) of NeuAc (Sigma) and NeuGc (Sigma) were used to establish calibration curves.

Fluorometric sialidase activity assay. Virus sialidase activity ($5\times10^5$ PFU was measured with 2'-(4-methylumbelliferyl)-α-D-N-acetylneuraminic acid (Sigma) as a substrate as described in Hara et al. (1987). Briefly the fluorogenic substrate, dilute 1:2 with 0.5 M sodium acetate (pH 4.6), was added to an equal volume of virus samples and incubated for 30 minutes at 37° C. Reactions were stopped with 200 ml of 0.5 M $Na_2CO_2$ (pH 10.7), and fluorescence was then incubated at an excitation wavelength of 360 nm and an emission wavelength of 460 nm. All reactions were performed in duplicate.

Sequence analysis of the NA and HA genes. Total viral RNA (vRNA) was obtained from virus sample with use of the Qiappin vRNA purification kit as instructed by the manufacturer (Qiagen, Inc., Valencia, Calif.). For cDNA production, the oligonucleotide Uni-12, complementary to the conserved 12 vRNA 3' terminal nucleotides of influenza A virus gene segments was used as a primer for the Moloney Murine Leukemia Virus reverse transcriptase (Promega, Madison, Wis.) reaction. The NA gene cDNA was amplified during 30 rounds of PCR with the NA gene-specific primers JN2-43 (5' cRNA sense sequence: 5'-TGGCTCGTTTCTCTCACTATTGCC-3'; SEQ ID NO:1) and JN2-1410r (3'-cRNA antisense sequence: 5'-TTATATAGGCATGAGATTGATGTCCG-3'; SEQ ID NO:2) and 10 U of Pwo DNA polymerase (Boehringer Mannheim). The resulting PCR products were subcloned into the vector pCR21 (Invitrogen, Carlsbad, Calif.) and used for automated fluorescent sequencing. The HA gene were cloned in a similar fashion with the HA gene-specific primers JH3-Up (5' cRNA sense primer sequence, 5'-AGCAAAAGCAGGGGATAATTCTATTAACCATGAAGAC-3'; SEQ ID NO:3) and JH3-Down (3' cRNA antisense primer sequence 5'-AGTAGAAACAAGGGTGTTTTTAATTAATGCACTC-3'; SEQ ID NO:4). For each isolate, three clones were examined to obtain a NA and HA consensus sequences.

Results

Generation of lectin-resistant cell lines. To produce cell lines with a decreased level of sialic acid expression on the cell surface, two lectins were used, SNA and MAA, that differ in sialic acid-binding specificity. The MAA lectin binds to sialic acid linked to galactose by α(2,3) linkages (Wang et al., 1988), while the SNA lectin is specific for sialic acids linked to galactose or N-acetylgalactosamine by α(2-6) linkages (Shibuya et al., 1987). The MDCK cell line, which supports the growth of influenza viruses, was used as a parent cell for lectin selection. When incubated in the presence of either lectin, the majority of cells died within a week. Resistant cell clones were then grown out for stock cultures. The cell lines resulting from MAA and SNA lectin selection were designated MDCK-Ma and MDCK-Sn10, respectively.

Fluorescent-activated cell sorting (FACS) with digoxigenin-labeled MAA and SNA lectins (FIG. 1A) demonstrated high levels of binding of MDCK cells to both lectins, as previously reported (Ito et al., 1997). MDCK-Sn10 cells, selected with α(2,6) linkage-specific lectin, retained strong binding to the α(2,3) specific MAA lectin but showed SNA lectin binding weaker than that of the MDCK parent. By contrast, MDCK-Ma cells, selected with the α(2-3) linkage-specific lectin, bound both lectins much more weakly than MDCK cells.

Viral growth in MDCK-Sn10 and MDCK-Ma cell lines. To learn how influenza viruses adapt to cells with reduced receptor expression, two influenza virus variants (AM2AL3 and K4) were chosen with known sialic acid receptor linkage specificity (Ito et al., 1997). The K4 virus specifically recognizes NeuAc linked to galactose by α(2-6) linkages [NeuAcα(2-6)Gal], while the AM2AL3 virus is specific for NeuAcα(2-3)Gal. Both viruses replicated almost as well in MDCK-Sn10 cells as in MDCK cells (Table 1). However, the titers of both viruses in MDCK-Ma cells were 1 log lower than in MDCK cells. Also, after infection with either virus, even at a multiplicity of infection of 10, a small percentage of MDCK-Ma cells continued to grow to confluency without any cytopathic effects. Virus production could not be detected in these surviving cells by hemagglutination assay upon replacement of the medium with that containing trypsin, which promotes virus growth. The cells were also negative by immunochemical staining for both influenza virus HA and NP proteins (data not shown), thus demonstrating that the cells were not persistently infected. The surviving cells were designated MaKS.

TABLE 1

Replication of influenza viruses in lectin-resistant cell lines*

| Cell line | Titer ($TCID_{50}$/ml) AM2AL3 | K4 |
|---|---|---|
| MDCK | $1.8\times10^9$ | $5.6\times10^4$ |
| MDCK-Sn10 | $5.6\times10^8$ | $3.2\times10^4$ |
| MDCK-Ma | $1.8\times10^8$ | $5.6\times10^3$ |

*The susceptibility of each cell line was determined by infecting cells with AM2AL3 or K4 with virus and determining the dose required to infect 50% of tissue culture cells ($TCID_{50}$).

Figure 1B:
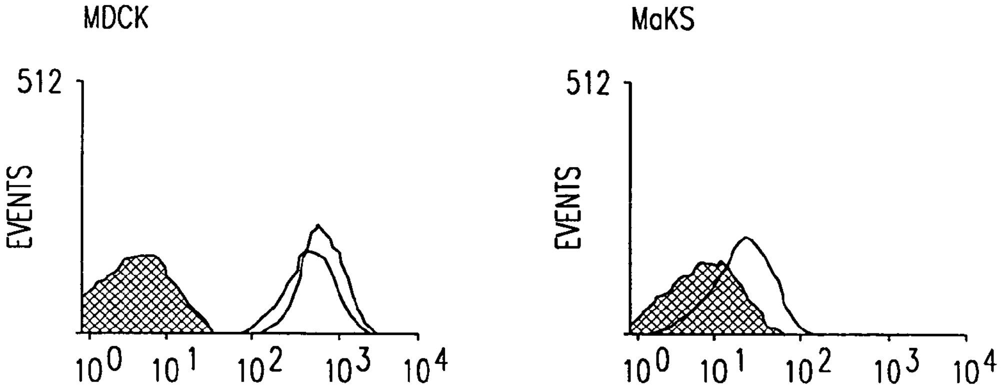

FACS analysis with both SNA and MAA lectins demonstrated that the MaKS cells, like the MDCK-Ma cells from which they were derived, bound the α(2,6)-specific SNA lectin much more weakly than did MDCK cells (FIG. 1B). In addition, the MAA lectin-binding peak of MaKS cells was much narrower than that of the MDCK-Ma cell line, with loss of a small shoulder peak representing a higher MAA-binding population (FIG. 1).

To determine whether reduced amounts of sialic acid were responsible for the reduced lectin binding of MaKS cells, the sialic acid levels present in the MaKS cells were quantified by liquid chromatographic analysis. The MaKS cell line showed much lower levels of both NeuAc and NeuGc (8.2 and 0.4 pmol/μg of protein, respectively) than MDCK cells (216.0 and 2.5 pmol/μg protein), although the NeuGc content was much lower. These data demonstrate an extensive reduction of sialic acid receptor determinant in MaKS cells.

Adaptation of virus in MaKS cells. To determine how AM2AL3 and K4 viruses propagate and adapt to growth in cells expressing very low levels of virus receptor, both viruses were serially passaged in MaKS cells in liquid culture. Since both viruses replicated more poorly in MaKS cells than in MDCK cells (Table 2), passages 1 through 3 were performed without dilution, and passages 4 through 13 were performed at 1:1,000 dilution. After passage 8, the diameter of plaques produced by either variant had changed from large (greater than 3 mm) to smaller (approximately 1 nm). By passage 10 and higher, only smaller plaques were present when the viruses were assayed with MDCK cells (data not shown). After 13 serial passages, both viruses were able to grow in MaKS cells as well as or better than in MDCK cells (Table 2). Virus stocks produced from either variant after passage 13 were amplified and designated AL3(MaKS)-13 and K4(MaKS)-13, respectively.

TABLE 2

Replication of viruses adapted to growth in lectin-selected cells*

| | Titer ($TCID_{50}$/ml) | | | |
|---|---|---|---|---|
| Cell line | AM2AL3 | AL3(MaKS)-13 | K4 | K4(MaKS)-13 |
| MDCK | $1.8 \times 10^9$ | $5.6 \times 10^4$ | $5.6 \times 10^4$ | $5.6 \times 10^4$ |
| MaKS | $5.6 \times 10^6$ | $5.6 \times 10^4$ | $1.8 \times 10^3$ | $1.8 \times 10^3$ |
| Resin, MDCK titer/MaKS titer | 321 | 1 | 31 | 0.3 |

*The susceptibility of each cell line was determined by infecting cells with AM2AL3 (grown in eggs), K4 (grown in MDCK cells). AL3(MaKS)-13 (grown in MaK3 cells), or K4(MaKS)-13 (grown in MaKs cells) stock virus and determining the dose required to infect 50% of tissue culture cells ($TCID_{50}$). Note that both viruses adapted in MaKS cells grow in these cells as well as [AL3(MaKS)-13] or better than [K4(MaKS)-13] in MDCK cells, while the original viruses grow better in MDCK cells.

Mutational analysis of the HA and NA genes of AL3 (MaKS)-13 and K4(MaKS)-13 viruses. To determine the molecular basis of virus adaptation to a cellular environment characterized by a reduced receptor concentration, the HA genes of the AL3(MaKS)-13 and K4(MaKS)-13 viruses were reverse transcribed, the cDNAs amplified by PCR, and the resulting products sequenced. Neither of the genes contained mutations by comparison with the corresponding HA genes from the two parental viruses.

Figure 2:
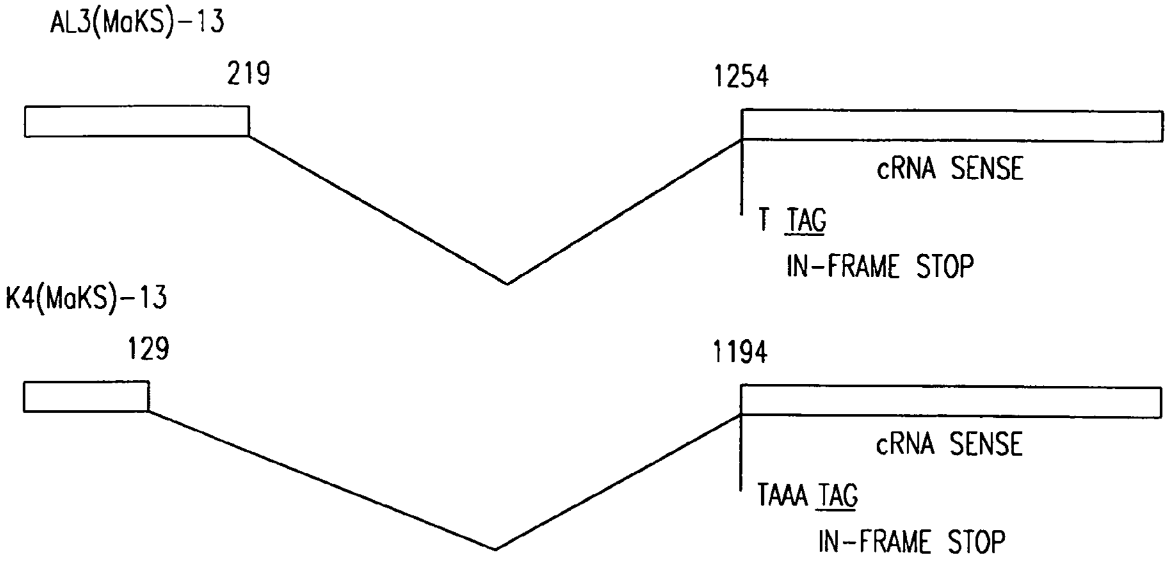
FIG. 2. Structures of the NA genes of the AL3(MaKS)-13 and K4(MaKS)-13 mutants. (A) The AL3(MaKS)-13 contains a 936-nucleotide deletion (from bases 220 to 1253) that removes a large portion of the NA gene coding sequence. This mutation also brings a TAG stop codon into frame two bases beyond the deletion, so that the gene encodes only a 66-amino-acid peptide, corresponding to the cytoplasmic tail, transmembrane region, stalk, and a portion of the head of NA. (B) The K4(MaKS)-13 NA gene contains a 1,066-nucleotide deletion (from bases 130 to 1193) that removes a large portion of the NA gene coding sequence. This mutation brings a TAG stop codon into frame four bases beyond the deletion, so that the gene encodes only a 38-amino-acid peptide, corresponding to the cytoplasmic tail and transmembrane region of the NA gene.

Since changes in NA sialidase activity likely influence HA receptor-binding activity, the NA sequence of the AL3 (MaKS)-13 and K4(MaKS)-13 viruses was determined. Sequence analysis of the NA genes of both variants revealed large internal deletions (FIG. 2). In AL3(MaKS)-13, the deletion extended from nucleotides 220 to 1253, shifting a reading frame and thus generating a stop codon immediately after the deletion. The coding capacity of this NA is 66 amino acids, corresponding to the cytoplasmic tail, the transmembrane domain, stalk region, and a short portion of the head region of NA. Similarly, the K4(MaKS)-13 isolate contained a deletion in the NA gene from bases 130 to 1193, bringing a stop codon into frame at codon 39. Like the AL3(MaKS)-13 virus, the gene no longer encoded a full catalytic head region. Thus, viruses passaged in a cell line with very low receptor expression lost their NA catalytic activity.

Figure 3:
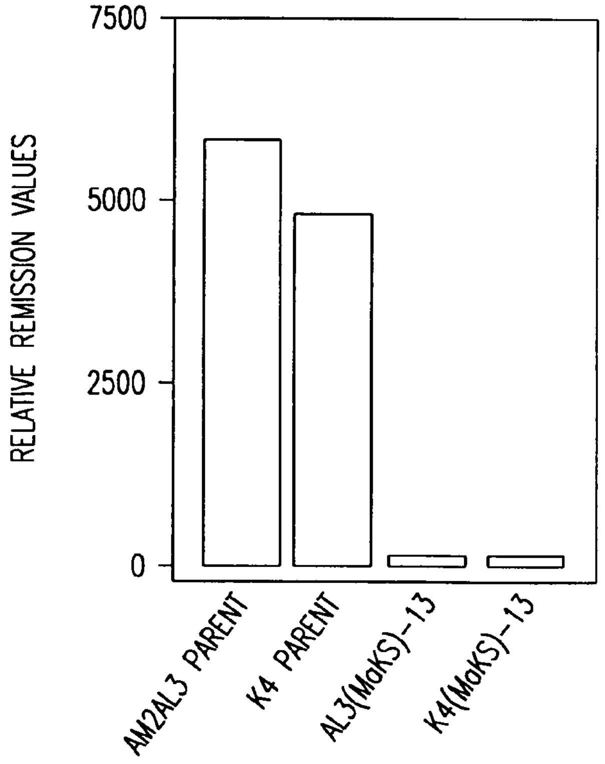
FIG. 3. Sialidase activity of the parental AM2AL3 and K4 viruses and the AL3(MaKS)-13 and K4(MaKS)-13 mutants. For each sample, virus ($5\times10^2$ PFU) was incubated in duplicate for 1 hour at 37° C. in the presence of a fluorogenic sialidase substrate (4-methylumbelliferyl-α-N-acetylneuraminic acid). The fluorescence of released 4-methylumbelliferone was determined with a fluorometer (Labsystems Fluoroskan II) with excitation at 360 nm and emission at 460 nm.

To confirm this result, the AL3(MaKS)-13 and K4 (MaKS)-13 variants were analyzed for sialidase activity, using a fluorescent sialidase substrate [2'(4-methylumbelliferyl)-α-D-N-acetylneuraminic acid]. Unlike the parental viruses, neither of the NA deletion mutants had detectable sialidase activity (FIG. 3).

Extent of sialylation of viral glycoproteins. During normal infection, viruses with reduced sialidase activity fail to grow efficiently and aggregate at the cell surface (Palese et al., 1974; Shibata et al., 1993). Why, then, do AL3(MaKS)-13 and K4(MaKS)-13 viruses, which lack sialidase activity, grow in MaKS cells? One possible explanation would be that since the sialic acid content of these cells is low, the extent of sialylation of the HA and NA oligosaccharides may also be low, preventing the aggregation of viruses at the infected cell surface, even when viral sialidase activity is absent. To test this hypothesis, the sialic acid content in purified virus preparations was compared between AM2AL3 and K4 viruses grown in MDCK cells and AL3(MaKS)-13 virus grown in MaKS cells. The NeuAc content was similar among the virus samples, although the AM2AL3 virus had lower sialic acid content (0.9 pmol of NeuAc/g of protein) than the other samples (A/Tottori/872/K4/94, 3.8 pmol of NeuAc/g of protein; AL3(MaKS)-13, 2.6 pmol of NeuAc/g of protein).

Thus, viruses lacking sialidase activity can grow efficiently in cells expressing a reduced level of sialic acid because the viral glycoproteins are not sialylated extensively compared with those in normal cell lines and are not bound by the HA, thus preventing viral aggregation.

Discussion

In previous studies, the passage of influenza A viruses in the presence of an exogenous bacterial sialidase activity and antibodies to the viral NA led to deletion of the viral NA gene (Liu et al., 1993; Liu et al., 1995; Yang et al., 1997). Moreover, NA mutants obtained by such passaging were able to grow in cell cultures lacking exogenous sialidase activity, as well as in eggs and mice, as a result of compensatory mutations in the HA protein that reduce the molecule's affinity for sialic acid residues (Hughes et al., 2000). As described herein, influenza A viruses can adapt to growth in cells with greatly reduced receptor expression by large NA gene deletion mutations that abolish sialidase activity. Even though the reduction of viral receptors could theoretically affect the receptor-binding HA protein, only the NA gene was altered.

What is the molecular basis of this finding? In normal cellular environments where sialic acid receptors are abundant, the loss of NA activity can be compensated for by reduction of the viral HA affinity for sialic acid, allowing efficient release of progeny from the host cell surface and preventing virion aggregation (Hughes et al., 2000). In the absence of high levels of viral receptors, as in our MaKS cells, a reduction of HA affinity is not necessary to release viral progeny and allow the growth of NA deletion mutants. In fact, high-affinity binding of the HA protein must be maintained for viral replication in cells expressing low levels of viral receptor. Sialidase activity, however, is not required for virion release and prevention of virion aggregation in such an environment, since the amounts of sialic acid on cell surface molecules are quite low and the sialic acid contents of NA deletion virions are similar to that of wild-type virions. In fact, sialidase activity is likely deleterious for viral growth because it further removes receptor determinant sialic acid from the cell surface. Recently, it was shown that influenza A virus lacking an NA stalk, and thus unable to grow in eggs, acquired a stalk insertion of up to 22 amino acids through nonhomologous RNA-RNA recombination (Mitnau et al., 2000). Taken together, these finding indicate that influenza viruses can adapt to new host environments by undergoing radical genetic changes, including large insertions and deletions.

In both this and previous studies (Hughes et al., 2000; Liu et al., 1993), viruses lost sialidase activity by internal deletions in the NA gene segment that spared segment ends encoding the cytoplasmic tail and transmembrane region. Thus, the preserved regions of the NA gene in these mutants may be necessary for functions such as virion morphogenesis and stability.

MaKS cells have a lower sialic acid content than their parental (MDCK) cells. Although similar cell lines have been produced from CHO cells (Ray et al., 1991), they have not proven useful for influenza virus studies because of their inability to support efficient influenza virus. By contrast, MaKS cells were derived from MDCK cells, a standard cell line in studies of influenza viruses, and should be useful in viral receptor-based analyses. For example, since exogenously added gangliosides are known to be incorporated into host cell membranes (Carroll et al., 1985), one could therefore incubate known gangliosides with MaKS cells and test their ability to serve as viral receptors.

During the past century, three influenza A virus pandemics arose when the HA or both the HA and NA genes of emerging viruses were introduced into a human population. Comparative studies of viruses from different host animals suggest that in these pandemic strains, mutations were introduced in the HA gene (Bean et al., 1992). Whether similar mutations are required in the NA to enable the virus to cross host species barriers remains unknown; however, the substrate specificity of the human virus N2 NA, which was derived from an avian virus, gradually changed during its replication in humans (Baum et al., 1991). Results described hereinabove indicate that NA mutations can indeed contribute to the ability of influenza A viruses to adapt to new environments. For example, a reassortment virus with human virus NA and the remaining genes from a duck virus failed to replicate in ducks (Hinshaw et al., 1983), even though the NA of the human virus originated from an avian virus (Scholtissek et al., 1978). This suggests that mutations likely occurred in the NA gene during adaptation in humans. Comparative studies of viral NAs from different animal hosts, in conjunction with recently developed plasmid-based reverse genetics (Fodor et al., 1999; Neumann et al., 1999), may yield useful insights into how these surface glycoproteins contribute to adaptive changes among influenza viruses in nature.

EXAMPLE 2

Materials and Methods

Cells. 293T human embryonic kidney cells were maintained in Dulbecco's medium supplemented with 10% fetal calf serum (FCS) and Madin-Darby canine kidney (MDCK) cells were maintained in Eagle's medium supplemented with 5% newborn calf serum.

Figure 4A:
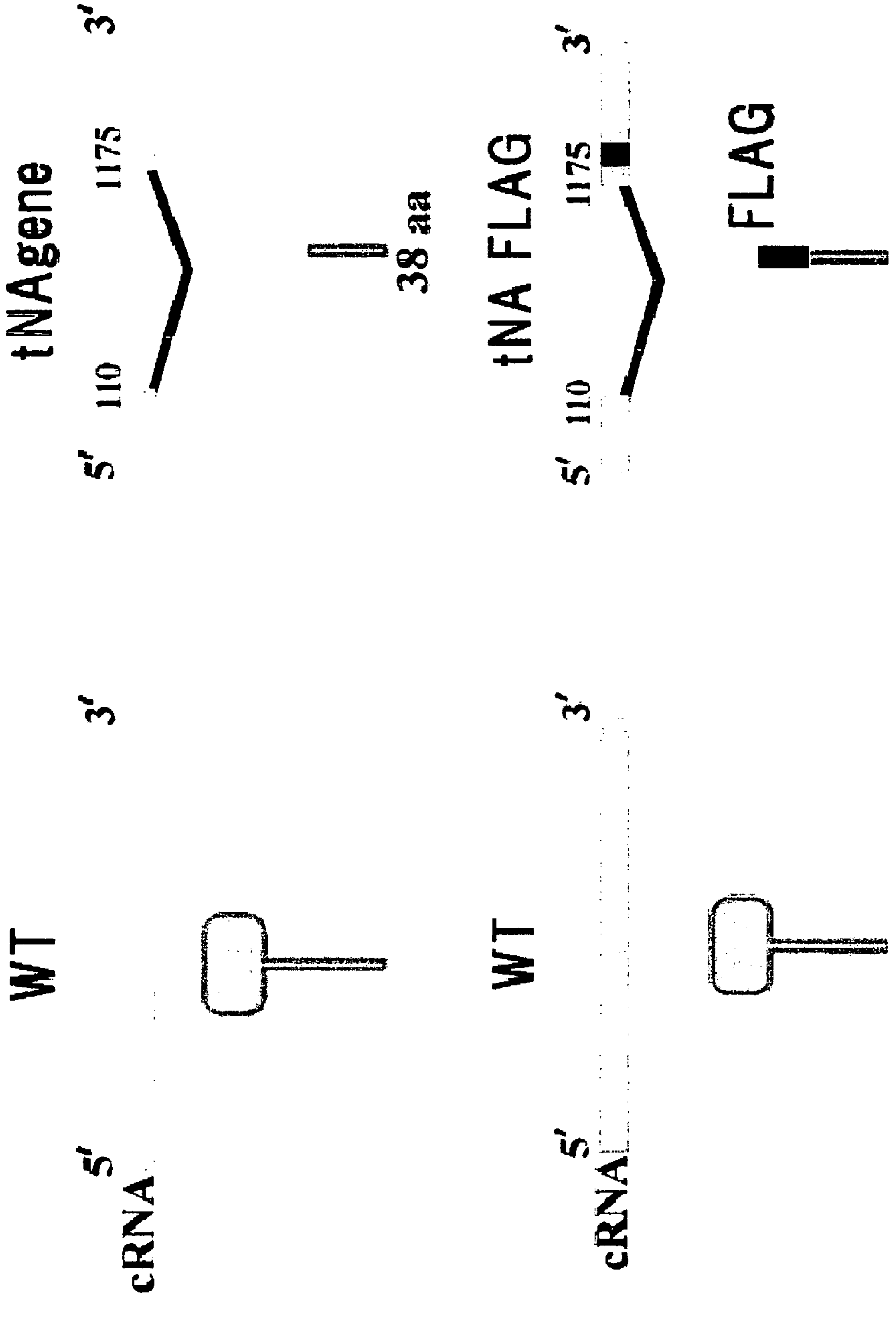
FIG. 4A. Schematic of wild-type and NAFLAG vectors.
Figure 4B:
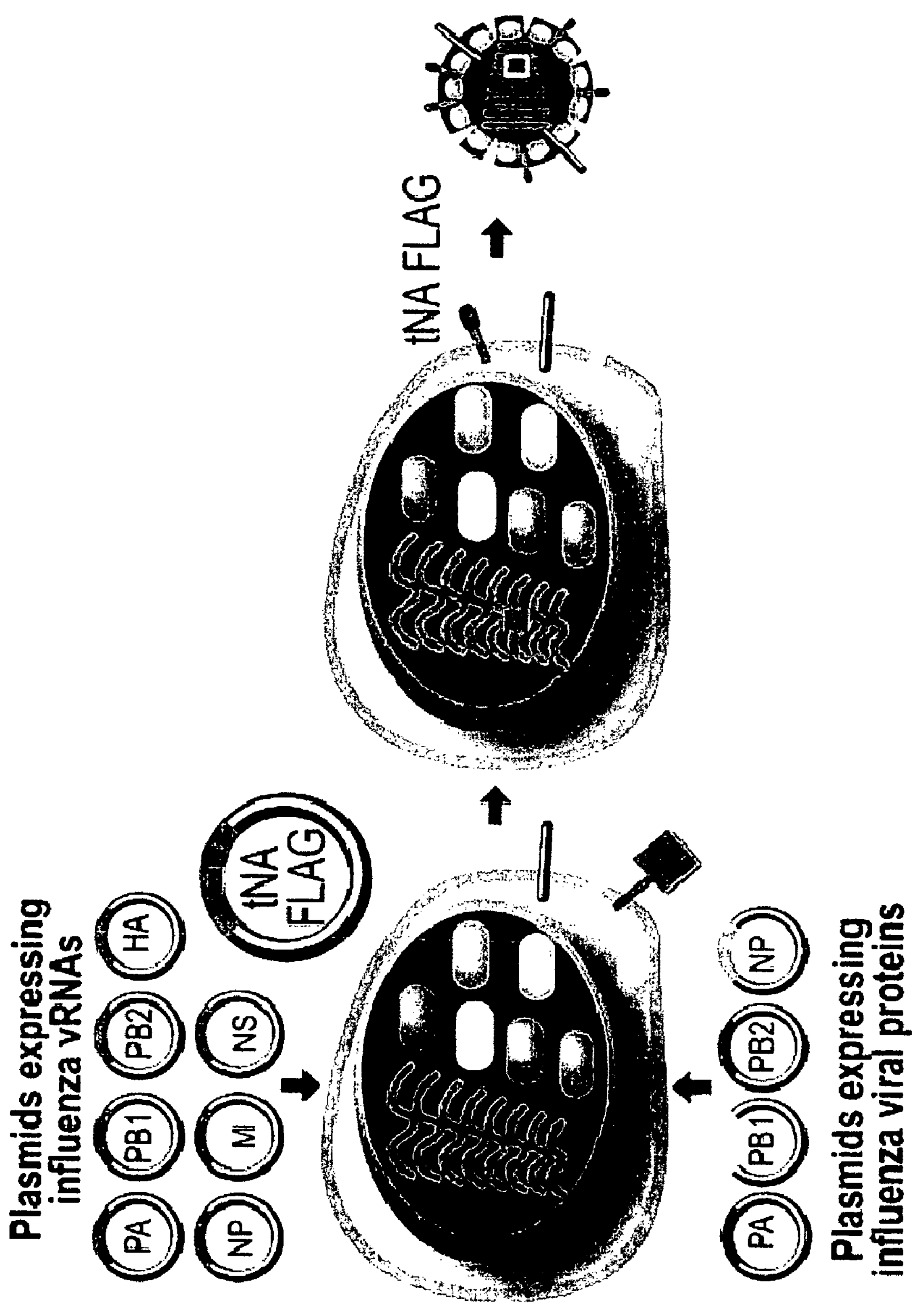
FIG. 4B. Schematic of method for NAFLAG virus production.

Plasmid-based reverse genetics. Influenza A viruses were generated using plasmids possessing the cDNA of A/WSN/33(H1N1) viral genes under the control of an RNA polymerase I promoter and terminator (referred to as PolI plasmids) and pCAGGS/MCS plasmids expressing influenza viral proteins as described in Neumann et al. (1999) (FIG. 4B). Briefly, PolI plasmids and protein expression plasmids were mixed with a transfection reagent, Trans IT LT-1 (Panvera, Madison, Wis.), incubated at room temperature for 10 minutes, and added to $1\times10^6$ 293T cells cultured in Opti-MEM (GIBCO/BRL). Forty-eight hours post-transfection, 0.5 µg per ml of trypsin was added to the medium to activate the HA protein, followed by incubation for 1 hour at 37° C. The supernatant was then collected.

Plasmids. The NAFLAG gene contains the 5' noncoding region of NA cRNA; 51 codons of NA corresponding to the cytoplasmic tail (6 amino acids), transmembrane (29 amino acids) and stalk region (16 amino acids) (FIG. 4A); the FLAG epitope (Asp-Tyr-Lys-Asp-Asp-Asp-Asp-Lys; SEQ ID NO:5); two sequential stop codons (TAA TAG; SEQ ID NO:6); and 185 bases of 3' terminus sequence of NA cRNA. This length of 3' terminus sequence is the shortest found in a truncated NA segment (Yang et al., 1997). pPol1-NAFLAGWT, which produces negative sense NAFLAG RNA, was made by deleting nucleotides 173 to 1070 (in the positive sense) of the WSN NA gene in pT7Blue-NA (which contains the full-length A/WSN/33 NA gene flanked by BsmB1 sites) and inserting the FLAG sequences, two stop codons and a StuI site by PCR. This fragment was digested by StuI, and self-ligated. The NAFLAG gene was excised with BsmBI and inserted into the BsmBI site of pHH21.

pPol1-NAFLAGM(−), for the production of NAFLAGM (−) vRNA, lacks the start codon for the NA protein. This was achieved by changing the ATG initiation codon for the truncated NAFLAG protein to GCG by in vitro site directed mutagenesis system (GeneEditor, Promega).

pPol1NA-(183)GFP(157), which generates RNA containing the 3' noncoding end of NA vRNA and complementary sequence encoding a fusion protein with 61 N-terminal NA codons, enhanced green fluorescent protein (eGFP, Clontech), and 185 bases of the 5' end of NA vRNA, was produced by replacing nucleotides 203 to 1109 (in positive sense) of WSN NA gene in pT7Blue-NA with a BglII site by inverted PCR. The eGFP gene was cloned into this BglII site and StuI site at position 1226 (in the wild-type NA gene) in frame with the NA protein. The NA-(183)GFP(157) gene was then inserted into the BsmBI site of pHH21.

The NA(0)GFP(0) gene, which contains the 3' noncoding region of NA vRNA, the complementary coding sequence of eGFP, and the 5' noncoding region of NA vRNA, was produced by PCR with oligonucleotide primers possessing a BbsI site. This PCR fragment was digested by BbsI and inserted into the BsmBI site of pHH21 so that upon introduction of the plasmid into cells, RNA containing eGFP coding sequence in negative-sense orientation flanked by 5' and 3' noncoding NA vRNA regions, is synthesized.

A series of deletion mutants were produced by PCR mutagenesis. The deletion mutants of NA-eGFP fusion protein were made from NA-(183)GFP(157) gene in pT7blue vector. The NA-(183)GFP(0) gene, which lacks the entire 3' terminus (positive sense) of the NA coding region of NA-(183)GFP(157), was produced by PCR mutagenesis. This mutant contains the 5' noncoding region (positive sense), 61 amino acids of NA sequence, the eGFP gene, two stop codons, and the 3' noncoding region. The PCR mutants, NA-(90)GFP(0), NA-(45)GFP(0), NA-(21)GFP(0) and NA-(18) GFP(0) contain 30, 15, 7, or 6 N-terminal amino acid deletions of the NA coding region of NA-(183)GFP(0), respectively.

The NA0G185 gene, which contains the 5' noncoding region, eGFP gene, two stop codons and 185 nucleotides of the 3' end of NA (positive sense) was made in the same manner from NA(61)GFP gene. This mutant has the 5' noncoding region of NA vRNA (28 nucleotides) and 157 nucleotides of NA 5' coding region of vRNA. The NA-(183)GFP (78) and NA-(183)GFP(39) mutants are deletion mutants of NA0G185, which have one-half or one-fourth of the NA 5' coding region as NA0G185, respectively.

Immunostaining. To detect the FLAG epitope attached to the C-terminus of the truncated NA protein, MDCK cells were infected with virus possessing this epitope and overlayed with 0.6% agarose containing 0.5 μg per ml of trypsin and 100 μU per ml of *Vibrio Cholerae* sialidase (GIBCO/BRL). The infected cells were fixed with 3% formaldehyde solution, permeated by 0.1% Triton-X100 in 3% formaldehyde solution. The FLAG epitope was then detected using a Vectastain ABC kit (Vector, Burlingame, Calif.) and anti-FLAG monoclonal antibody M2 (Sigma) as the primary antibody and biotinylated anti-mouse IgG as the secondary antibody. To identify WSN virus infected cells, a rabbit anti-WSN sera was employed as the primary antibody.

In situ hybridization. Infected cells were hybridized with digoxigenin(DIG)-labeled probe and stained using a DIG Nucleic Acid Detection Kit (Roche), according to the manufacturer's protocol. An oligonucleotide (100 pmol) complementary to the nucleotide sequence encoding the FLAG epitope (GACTACAAGGACGACGATGACAAG; SEQ ID NO:7) was labeled by DIG Oligonucleotide Tailing Kit (Roche) at 37° C. for 6 hours. Virus-infected cells were fixed with 3% formaldehyde solution, permeated by 0.1% Triton-X 100 in 3% formaldehyde solution and prehybridized at 65° C. for 30 minutes in prehybridization buffer (5×SSC, 1% Blocking Reagent of the Detection Kit, 0.1% N-lauroylsarcosine, 0.02% sodium dodecyl sulfate [SDS]) containing 0.1 mg/ml of Poly(A)-DNA of the Detection Kit). Oligonucleotide probes (10 pmol) were added to the prehybridization buffer and hybridized at 55° C. for 1 hour. The hybridized cells were washed for 5 minutes with wash buffer (0.1 M maleic acid, 0.15 M NaCl, 0.3% Tween 20, pH 7.5), blocked with 1% Blocking Reagent for 30 minutes at room temperature, and incubated with anti-DIG antibody (1:500) conjugated with alkaline phosphatase for 30 minutes at room temperature. Cells were then washed with the wash buffer and incubated with nitroblue tetrazolium chloride/5-bromo-4-chloro-3-indolyl-phosphate (NBT/BCIP) in the detection buffer (0.1 M Tris-HCl, 0.1 M NaCl, pH 9.5) at room temperature for 3 hours in the dark.

Competitive passages. NAFLAGWT or NAFLAGM(−) virus (300 plaque forming units [PFU]) was mixed with $3\times10^4$ PFU of NA(−) virus and used to infect subconfluent MDCK cells (multiplicity of infection of 0.01) and incubated for 72 hours in medium containing 0.5 μg per ml of trypsin and 100 μU per ml of *Vibrio cholerae* sialidase. The viruses harvested were used to infect MDCK cells. This process was repeated 5 times.

Results

An influenza A virus lacking the NA gene segment is viable. The maintenance of truncated NA gene after repeated passage suggested its importance for viral replication. To generate a mutant influenza A virus without the NA RNA segment, 293T cells were transfected with plasmids for the production of vRNA, with the exception of NA vRNA, and those for the expression of nine structural proteins. Upon incubation of supernatant of the 293T cell culture with MDCK cells in the presence of *Vibrio Cholerae* sialidase, plaques (189±15.6 μm diameters) were observed. In liquid culture, this virus (designated NA(−)) grew up to $10^5$ PFU/ml. Thus, an influenza A virus with only 7 vRNA segments was viable.

Figure 4C:
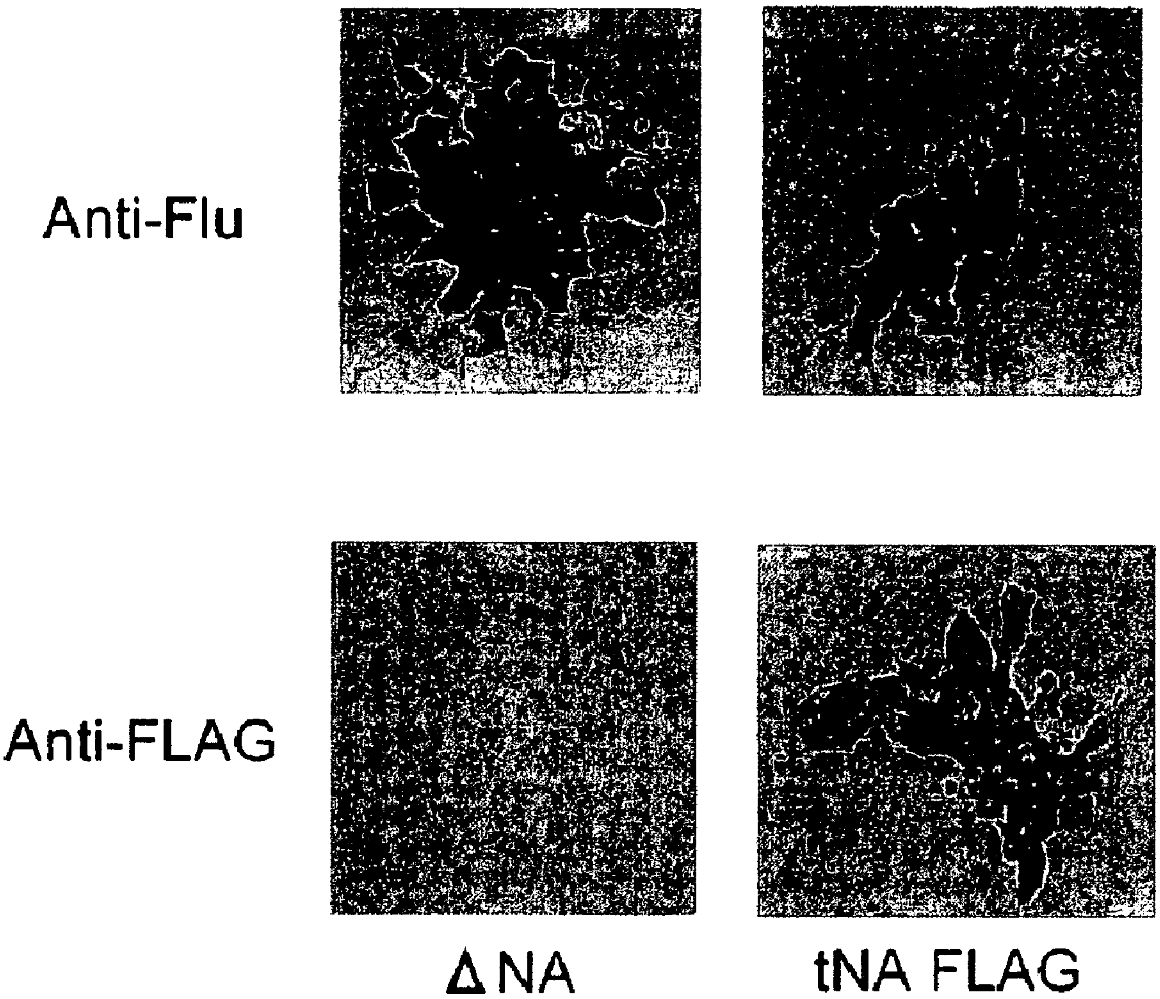
FIG. 4C. Immunostaining of MDCK cells infected with NAFLAGWT virus or NA(−) virus. The cells were stained with anti-FLAG monoclonal antibody (MAb) M2 or anti-WSN polyclonal antibody.

A truncated NA segment is required for efficient viral growth. To understand the molecular basis for the stable maintenance of the truncated NA gene after repeated passage, the growth of virus containing a truncated NA gene was compared to virus lacking the start codon for the NA gene, coding NA(−) virus. A mutant virus, NAFLAGWT, was generated by reverse genetics. NAFLAGWT has an NA gene with an internal deletion and a FLAG epitope sequence fused to the truncated NA gene. NAFLAGWT grew up to $10^5$ PFU/ml and produced plaques in the presence of a bacterial sialidase. The plaques were immunostained with anti-FLAG monoclonal antibody or anti-WSN polyclonal antibody (FIG. 4C). Plaques produced by NA(−) or NAFLAGWT virus were stained with anti-WSN antibody but only those of the latter virus were stained with the anti-FLAG antibody.

Figure 5:
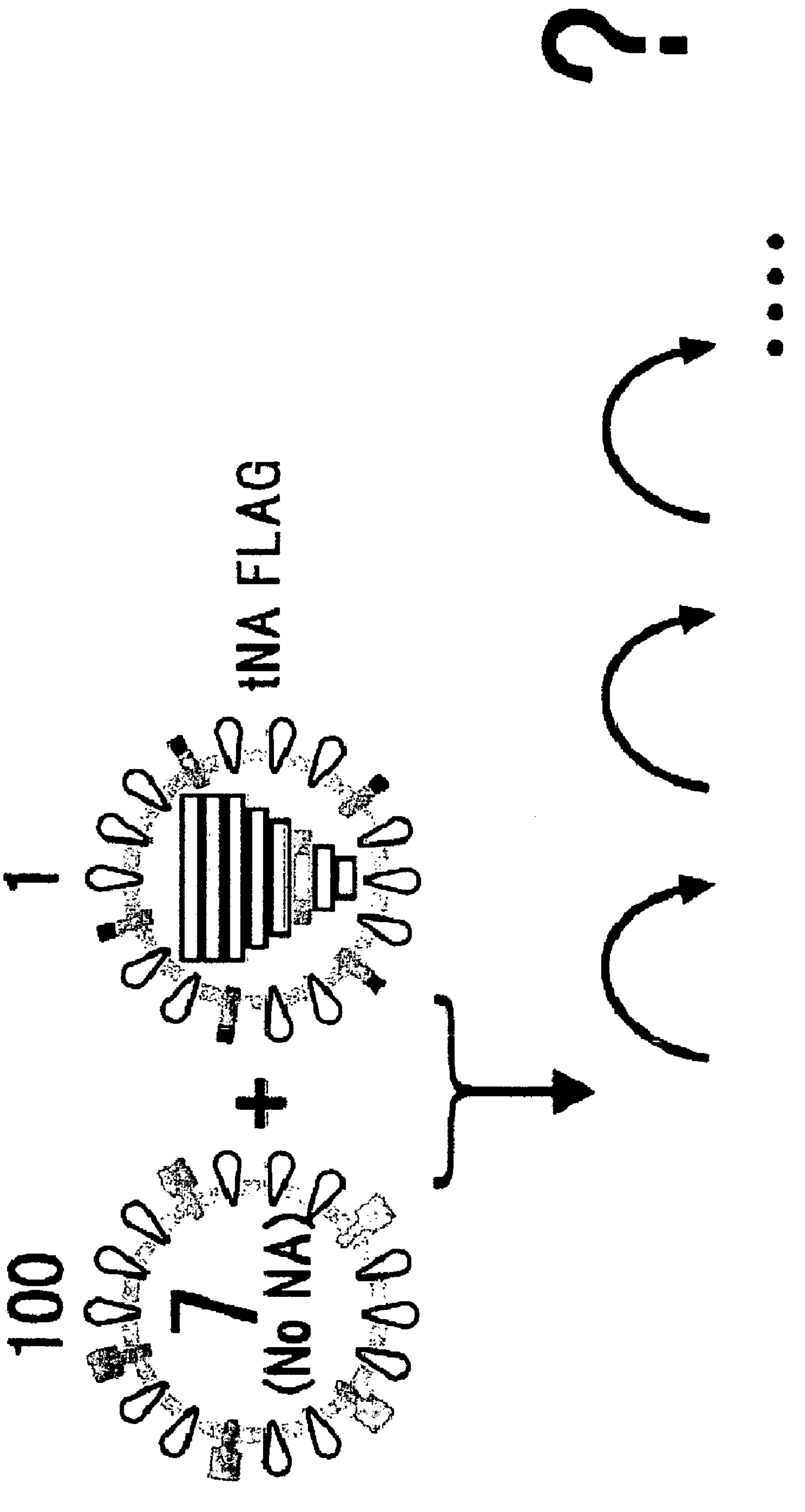
FIG. 5. Schematic of competition analysis for a recombinant 7 segment influenza virus and NAFLAG virus.
Figure 7A:
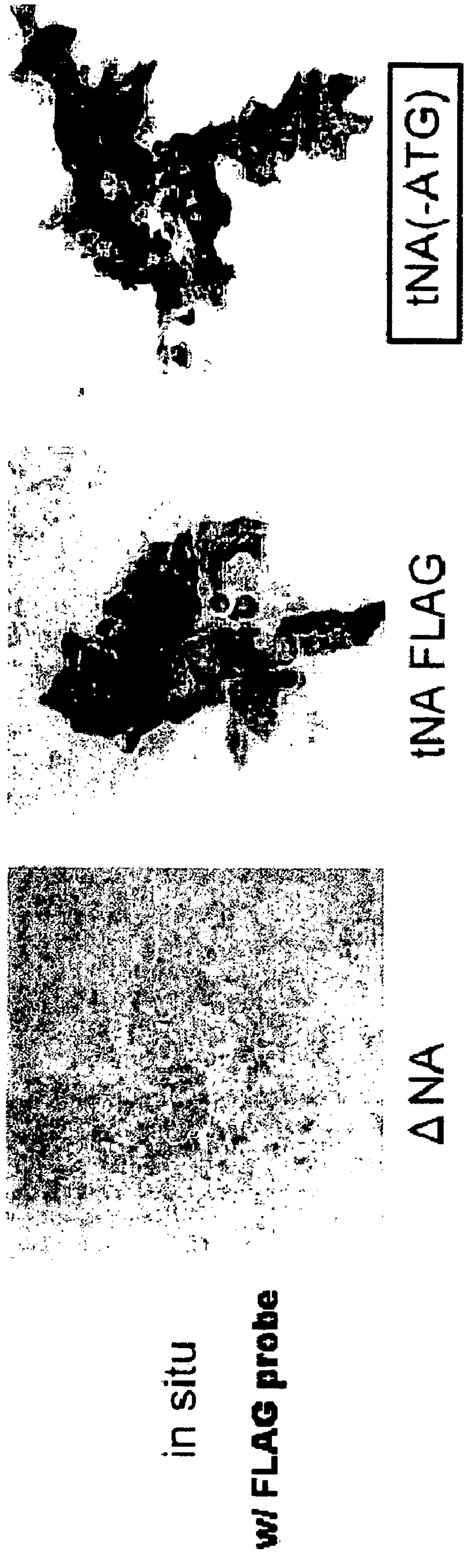
FIG. 7A. In situ hybridization analysis of NAFLAG and NAFLAGM(−) infected cells for FLAG sequence.
Figure 7B:
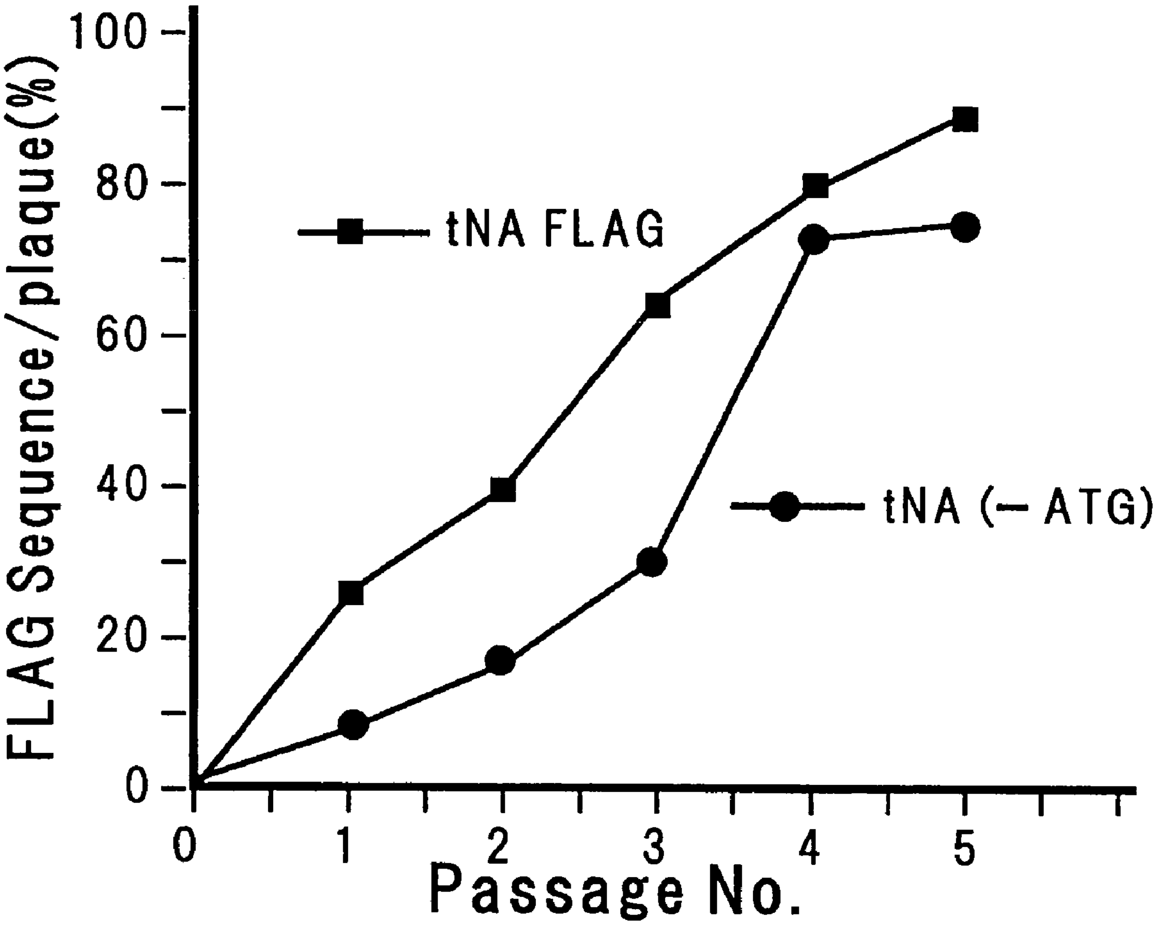
FIG. 7B. Replication efficiency of NAFLAGWT virus or NAFLAGM(−) virus.

To determine the difference in replicative ability, NA(−) and NAFLAGWT viruses were mixed at a ratio of 100:1 and this mixture incubated with MDCK cells (FIG. 5). At 48 hours post-infection, the supernatant was removed and used for the production of plaques, which were immunostained with anti-FLAG monoclonal antibody. The prevalence of virus with the truncated NA segment was determined by calculating the percentage of FLAG-positive plaques among total plaques. This procedure was repeated 4 more times. As shown in FIG. 7B, the FLAG-positive plaques in the population gradually increased during passage, reaching nearly 90% by the fifth passage. This result shows that a virus with 8 segments (even though the truncated NA gene does not encode a functional sialidase) grows better than a virus with 7 segments.

Figure 6A:
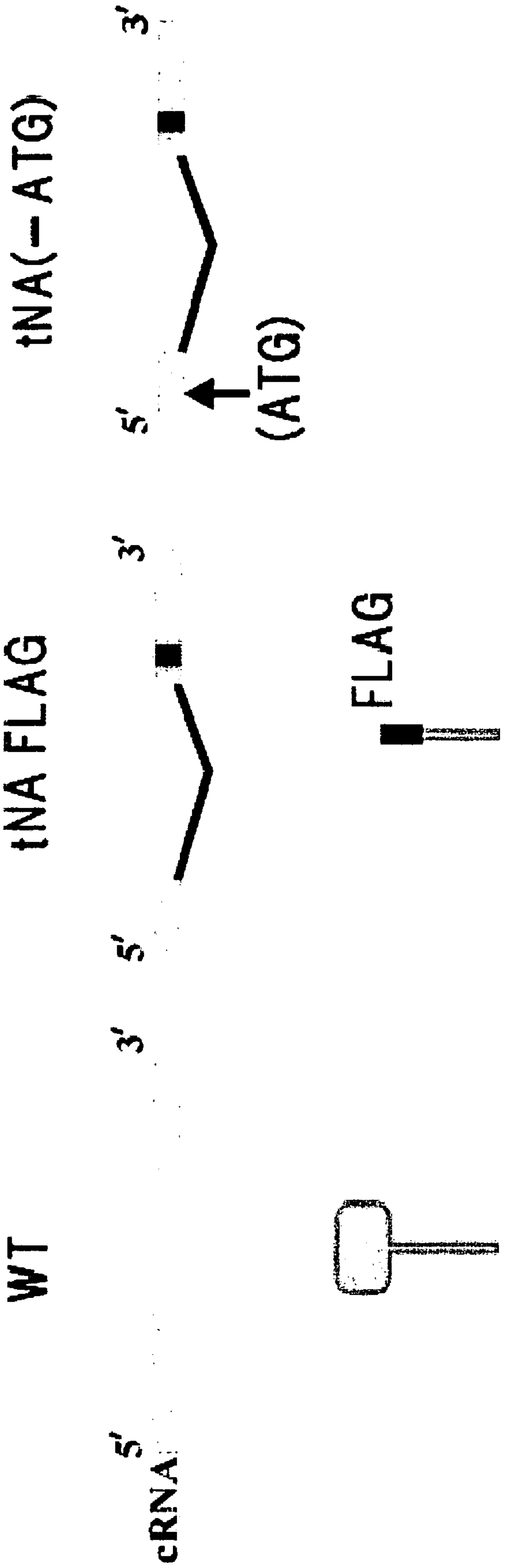
FIG. 6A. Schematic of NAFLAG and NAFLAGM(−)("−ATG") vectors.
Figure 6B:
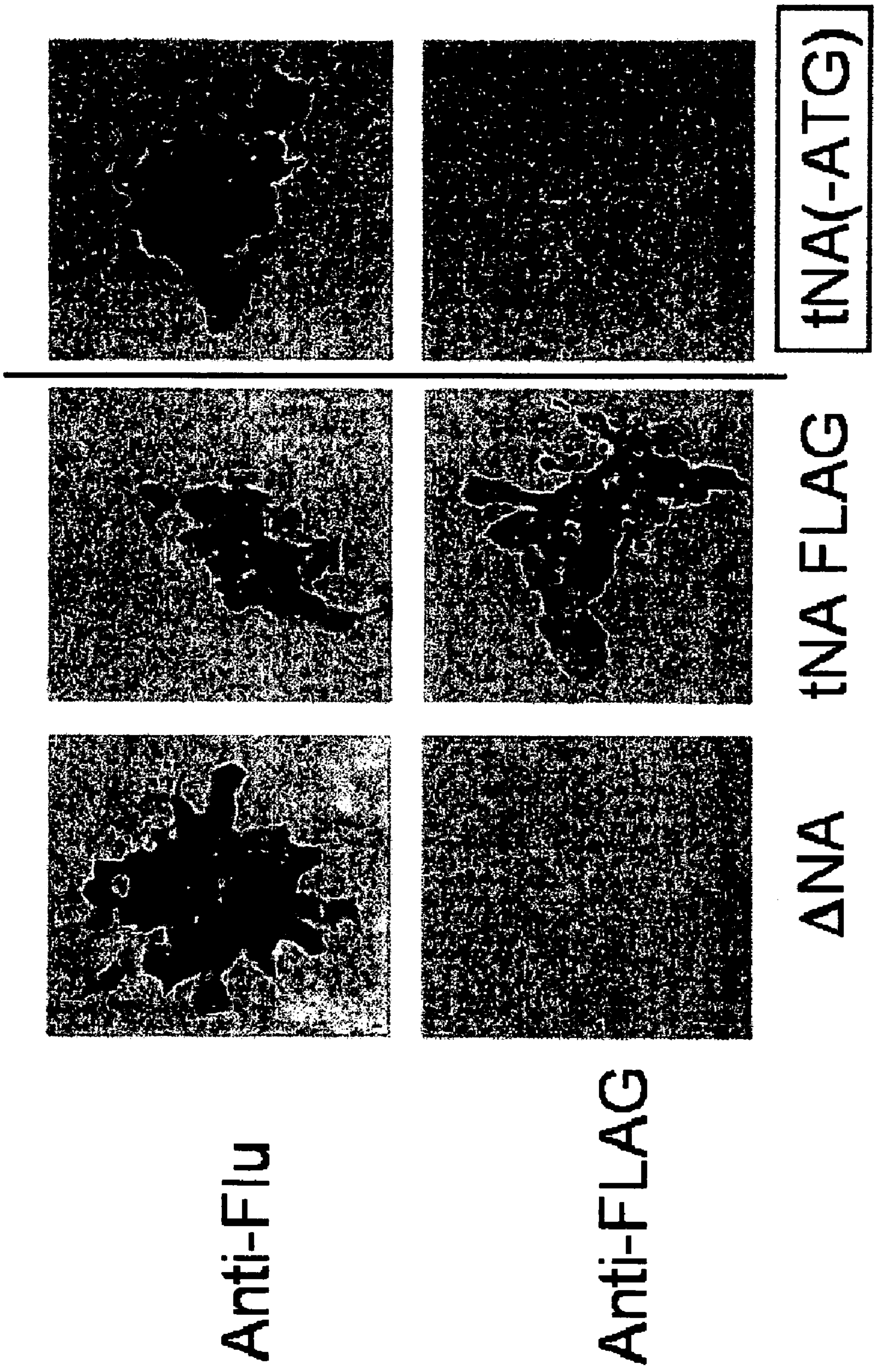
FIG. 6B. Immunostaining of MDCK cells infected with NAFLAGM(−) virus. The cells were stained with anti-FLAG monoclonal antibody M2 or anti-WSN polyclonal antibody.

Viral RNA is important for efficient viral growth. To determine whether a truncated NA protein or viral RNA is important for efficient viral replication, a NAFLAGM(−) gene was constructed which lacks both the NA start codon and another in frame ATG codon (the fifteenth codon) (FIG. 6A). Plaques produced by NAFLAGM(−) virus were not detected by anti-FLAG antibody (FIG. 6B), indicating that the protein was not translated. To ensure that NAFLAGM(−) virus possesses the NAFLAGM(−) gene, in situ hybridization was performed on plaques produced by this virus using a FLAG sequence-specific probe. These plaques reacted with the probe, confirming the presence of the NAFLAGM(−) gene in this virus. The replicative ability of this virus was then compared with the 7 segment virus described above. The percentage of plaques labeled with the FLAG sequence-specific probe gradually increased (FIG. 7B), and nearly 80% of the plaques became FLAG sequence-positive by the fifth passage (FIG. 7A). There were no revertants to those expressing the truncated NA protein during passage, as demonstrated by the lack of staining with anti-FLAG antibody. Thus, viral RNA itself seems to play an important role in efficient viral replication, although the truncated NA protein may also play a role in efficient viral replication since the rate at which the NAFLAGM(−) became dominant in the mixed infection was slower than that of NAFLAGWT virus.

Figures 8A, 8B:
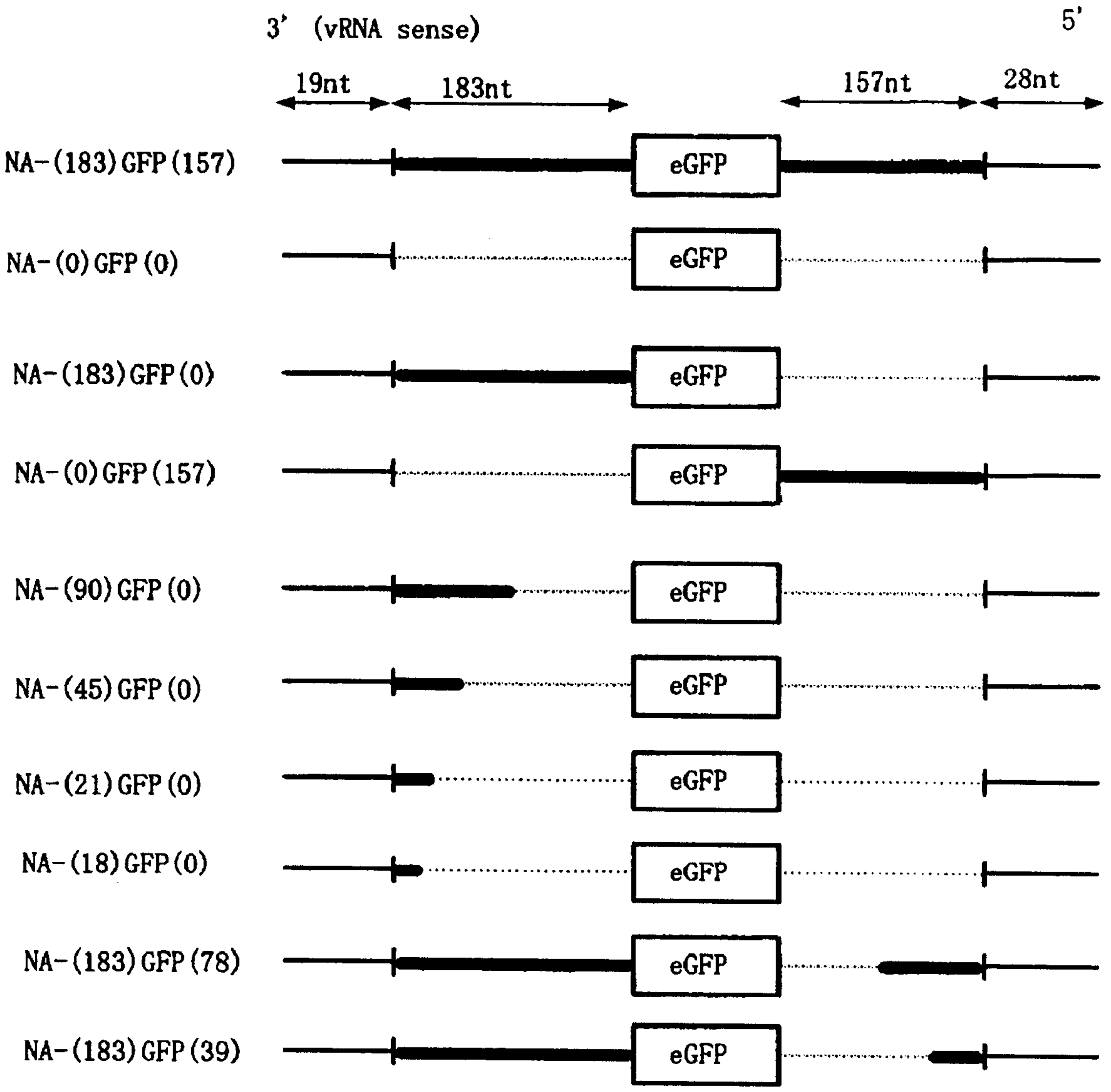
FIG. 8A. Schematic of NA deletion viruses.
FIG. 8B. Packaging rate of NA deletion viruses.

A packaging signal of viral NA RNA extends into the coding sequence. Even after extensive passage of CK2-29 and E17E virus (Hughes et al., 2000), the truncated NA gene was maintained, suggesting that the signal for vRNA incorporation into virions (i.e., packaging signal) is present in the coding region of the NA RNA segment. To test this hypothesis, an eGFP coding sequence was inserted into the truncated NA gene in-frame where the NA sequence was deleted. Thus, this recombinant gene, designated NA-(183)GFP(157), possesses the 3' noncoding end of NA vRNA and 61 codons of the N-terminal NA coding region, an eGFP coding region, and 185 nucleotides of the 5' end of NA vRNA. A virus possessing the NA-(183)GFP(157) gene instead of the corresponding wild type NA gene was prepared and plaque assays performed (FIG. 8A). Over 90% of the plaques expressed eGFP indicating that the NA-(183)GFP(157) gene was incorporated into virions and maintained during viral replication (FIG. 8B). This finding was interesting considering that the CAT sequence flanked by NS noncoding sequences was not maintained for more than 5 passages (Luytjes et al., 1989).

Since the difference between the NA-(183)GFP(157) and the CAT constructs is the presence of the viral coding sequence, a gene similar to the CAT construct was generated, NA(0)GFP(0), that contains eGFP coding sequence flanked by the 3' and 5' NA noncoding regions. This construct lacks the NA coding sequence. Although the virus generated with this gene produced plaques, only a minor population (0.1%) of plaques had one or two eGFP-expressing cells, indicating that the NA(0)GFP(0) gene was not maintained in virus during viral replication. In 293T cells transfected with plasmids, including one expressing the NA(0)GFP(0) gene for viral production, eGFP was expressed at a lesser extent as compared with those transfected with the plasmid expressing NA(61)GFP. The amount of PolI plasmid for NA(0)GFP(0) was increased by 10-fold, resulting in a similar number of eGFP-expressing 293T cells as cells transfected with PolI plasmid for NA(61)GFP. Even with the 10-fold higher amount of the PolI plasmid for this gene, only 1% of the plaques produced by the NA(0)GFP(0) virus contained eGFP positive cells and only a few cells in these plaques expressed eGFP. These results indicated that the packaging signal of viral NA RNA extends into the NA coding sequence.

Figure 9:
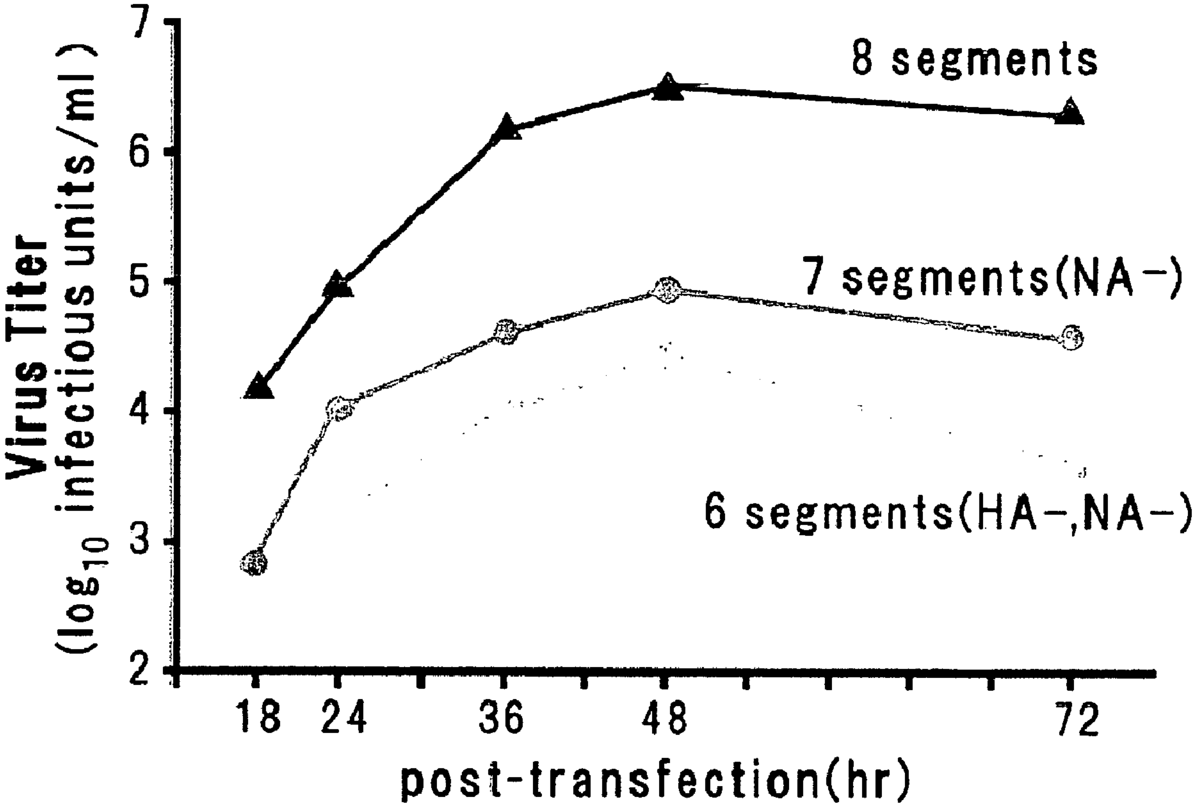
FIG. 9. Virus titer over time for influenza viruses with 6, 7 or 8 segments.
Figure 10:
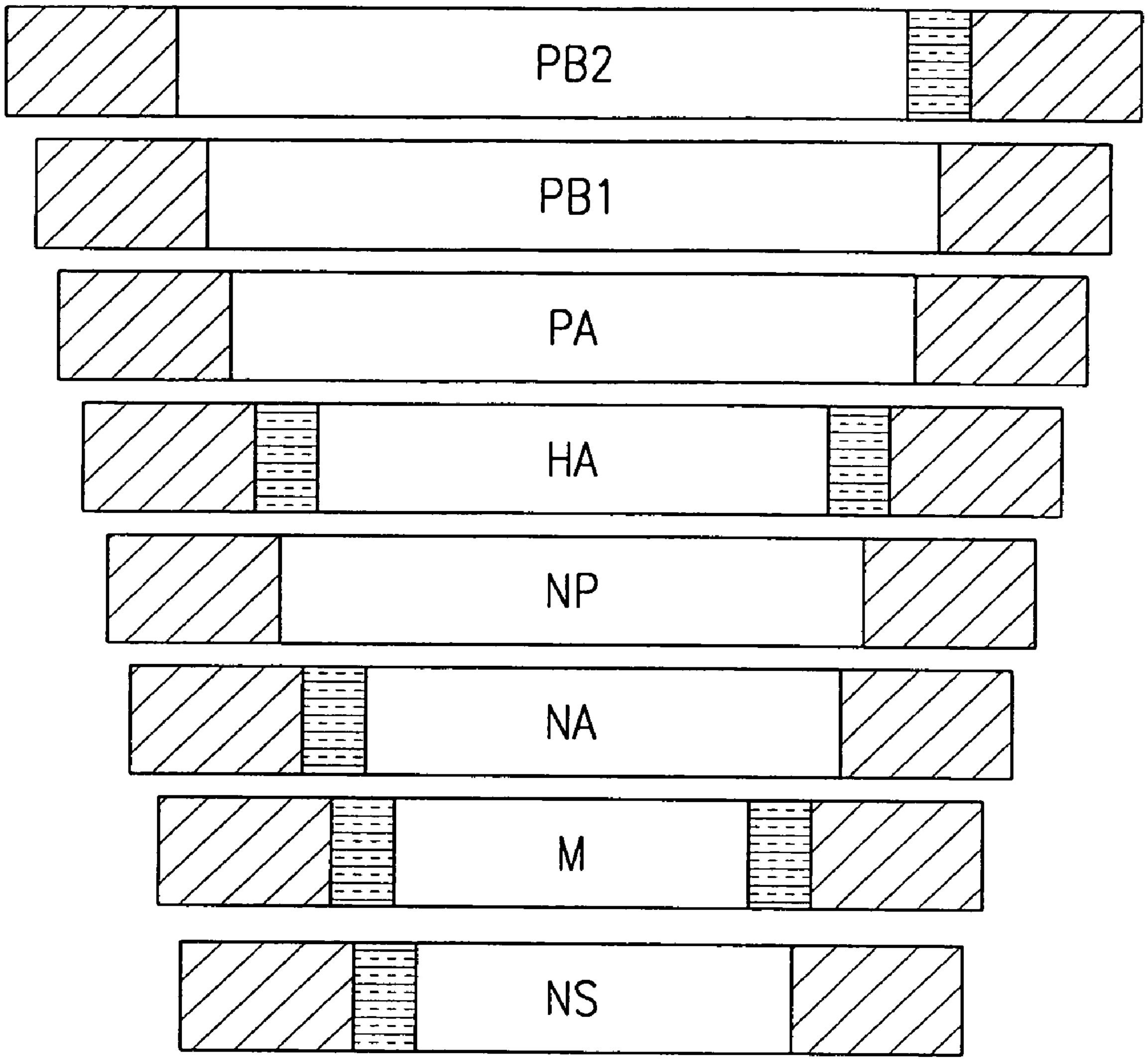
FIG. 10. Schematic showing incorporation signals for influenza viral segments (stipled).

The role of RNA segments in efficient virion production. To understand why a virus with 8 RNA segments grows better than one with 7 segments, infectious virion production was compared among viruses possessing 6, 7, or 8 viral RNA segments (FIG. 9). To produce an 8 segment virus, 293T cells were transfected with protein expression plasmids for all 9 structural proteins and 8 PolI plasmids for normal viral production. Also, a NS PolI plasmid which has two mutations that eliminate NS2 production was used; thus, virus produced from 293T cells does not undergo multiple cycles of replication. In addition, HA and NA PolI plasmids were used that have mutations that eliminate production of HA and NA proteins, respectively, so that the effect of the elimination of gene segments is restricted only to the RNA segment, not the gene product. For the production of a 7 segment virus, the PolI plasmid for the NA gene was eliminated, however, a plasmid for the expression of NA protein was included. To prepare a virus with 6 segments, the plasmids for HA and NA RNAs were omitted, however, plasmids for the expression of HA and NA proteins were included.

To compare virion production among these viruses, the number of infectious virions produced from plasmid-transfected cells was titrated by infecting MDCK cells with these viruses and immunostained infected cells with anti-WSN antibody 48 hours postinfection. As shown in FIG. 9, the efficiency of infectious virion production was correlated with the number of viral RNA segments; the higher the number of viral RNA segments, the better the virion production. These results indicate the role of viral RNA segments in efficient virion productions.

The 3' end of NA vRNA is important for its packaging into virions. To narrow down the packaging signal in NA vRNA, viruses were prepared that had truncated NA genes with further deletions in the 3' or 5' (vRNA sense) coding region (FIG. 8A). Approximately 40% of plaques produced by NA-(183) GFP(0) virus, which lacks the 5' terminus of the NA coding region, expressed eGFP, while only 1.8% of plaques produced by NA0G185 virus which lacks the 3' terminus of NA coding region expressed eGFP. These data indicate that 3' terminus of the NA vRNA coding region is important for virion packaging (FIG. 8).

Discussion

Figure 22:
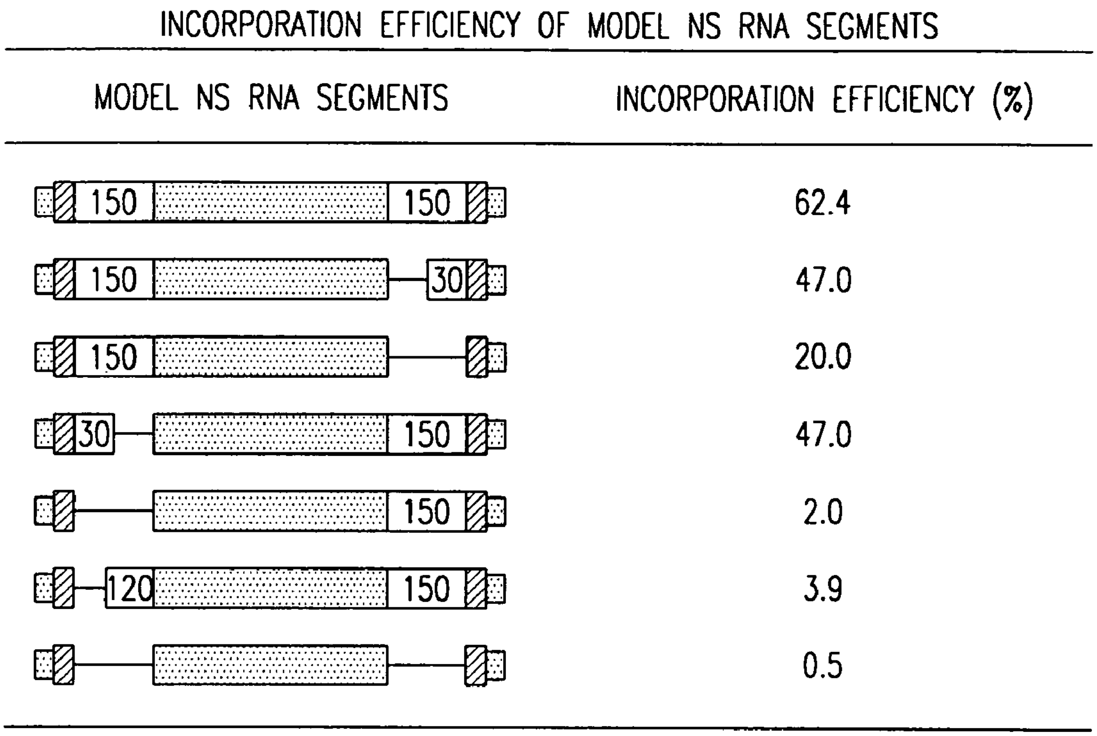
FIG. 22. Schematic diagram of mutant NS vRNAs and their efficiency of incorporation.
Figure 23:
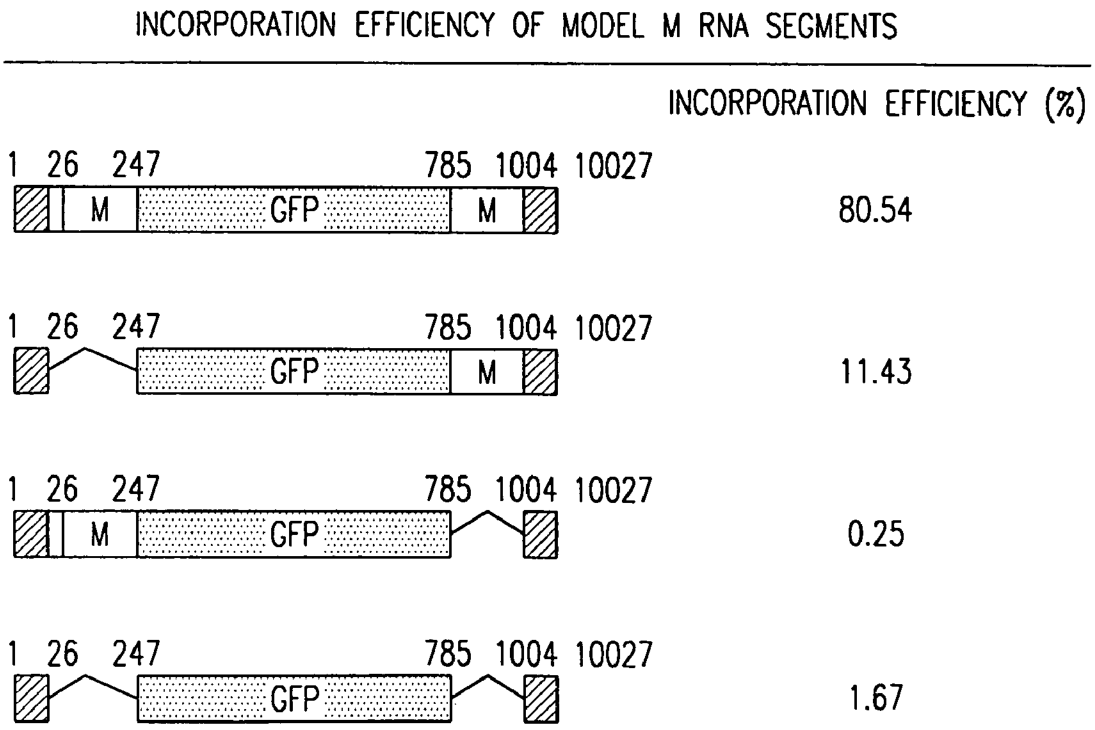
FIG. 23. Schematic diagram of mutant M vRNAs and their efficiency of incorporation.

By making deletion constructs, the NA coding region which resulted in the incorporation of the NA segment into virions was determined. Both ends of the coding regions were found to be important, but the 3' end of vRNA corresponding to the 5' terminus of the NA coding region was more consequential than the other end. For the NS segment, the 3' end of vRNA corresponding to the 5' terminus of the NS coding region appears more important than the other end for incorporation (FIG. 22). By contrast, for the HA, M, and NP segments, both ends are important, and for PB2 the 5' end of vRNA corresponding to the 3' terminus of the PB2 coding region, is important. These results show that sequences important for vRNA segment incorporation are located in the coding regions, and are therefore unique to each segment. Possibly, those regions interact with other viral RNAs by base pairing, leading to recruitment of a set of 8 vRNA segments into a virion. Since the interaction between vRNA and viral components is virus-specific, that interaction can be a target for the development of antiviral compounds.

EXAMPLE 3

Figure 11A:
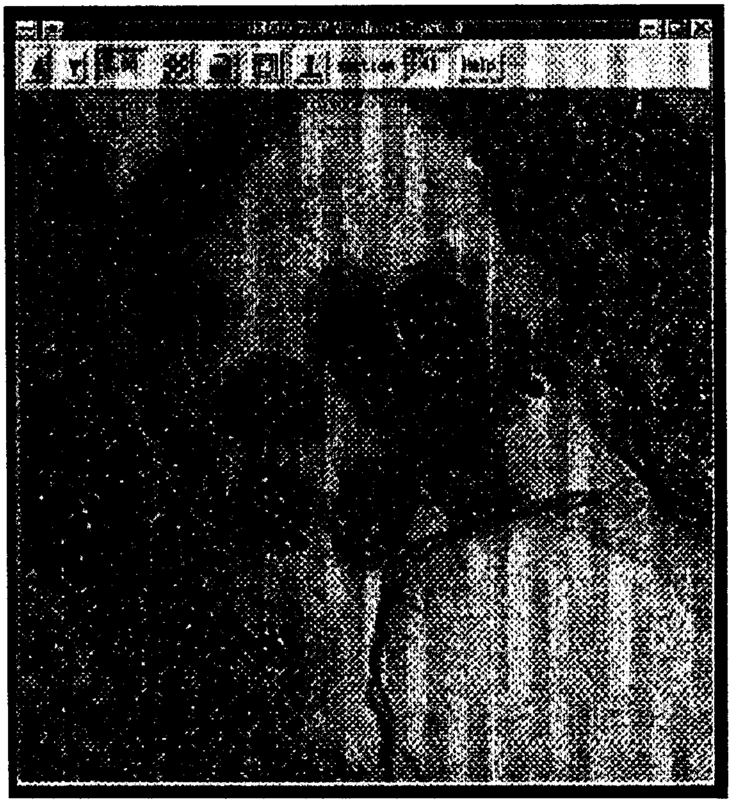
FIG. 11A. Electron microscope tomography of influenza virions.
Figure 11B:
FIGS. 11B-F. Color images of rods found by electron microscope tomography of an influenza virion.
Figure 11C:
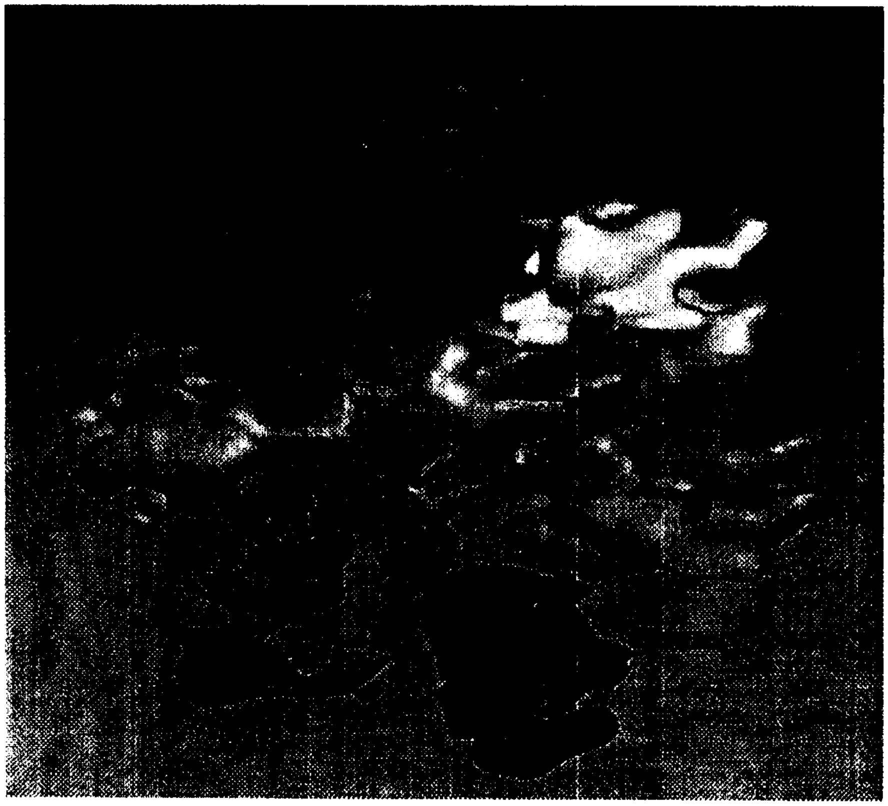
Figure 11D:
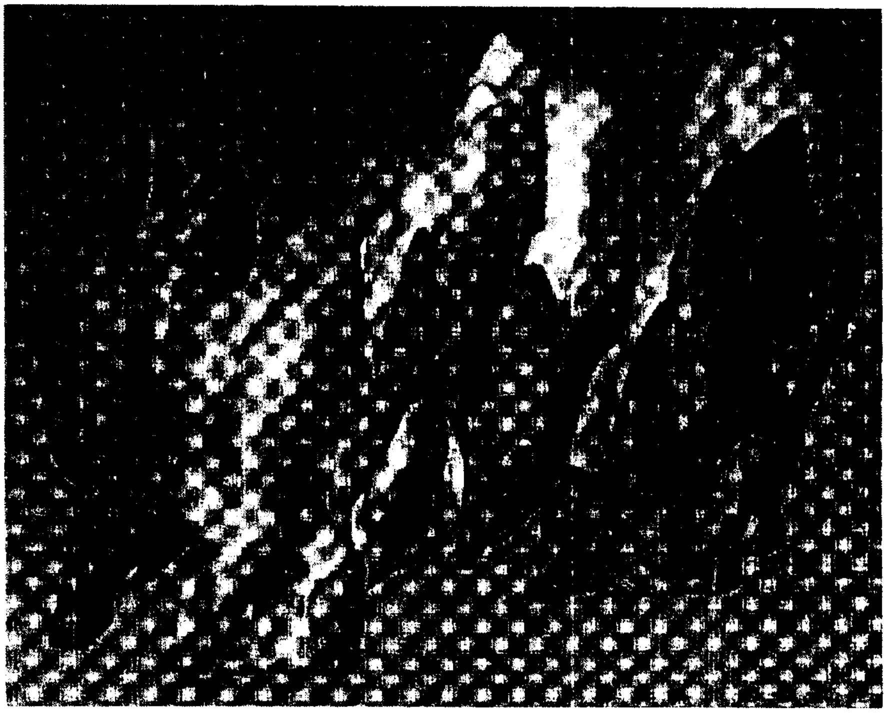
Figure 11E:
Figure 11F:
Figure 12A:
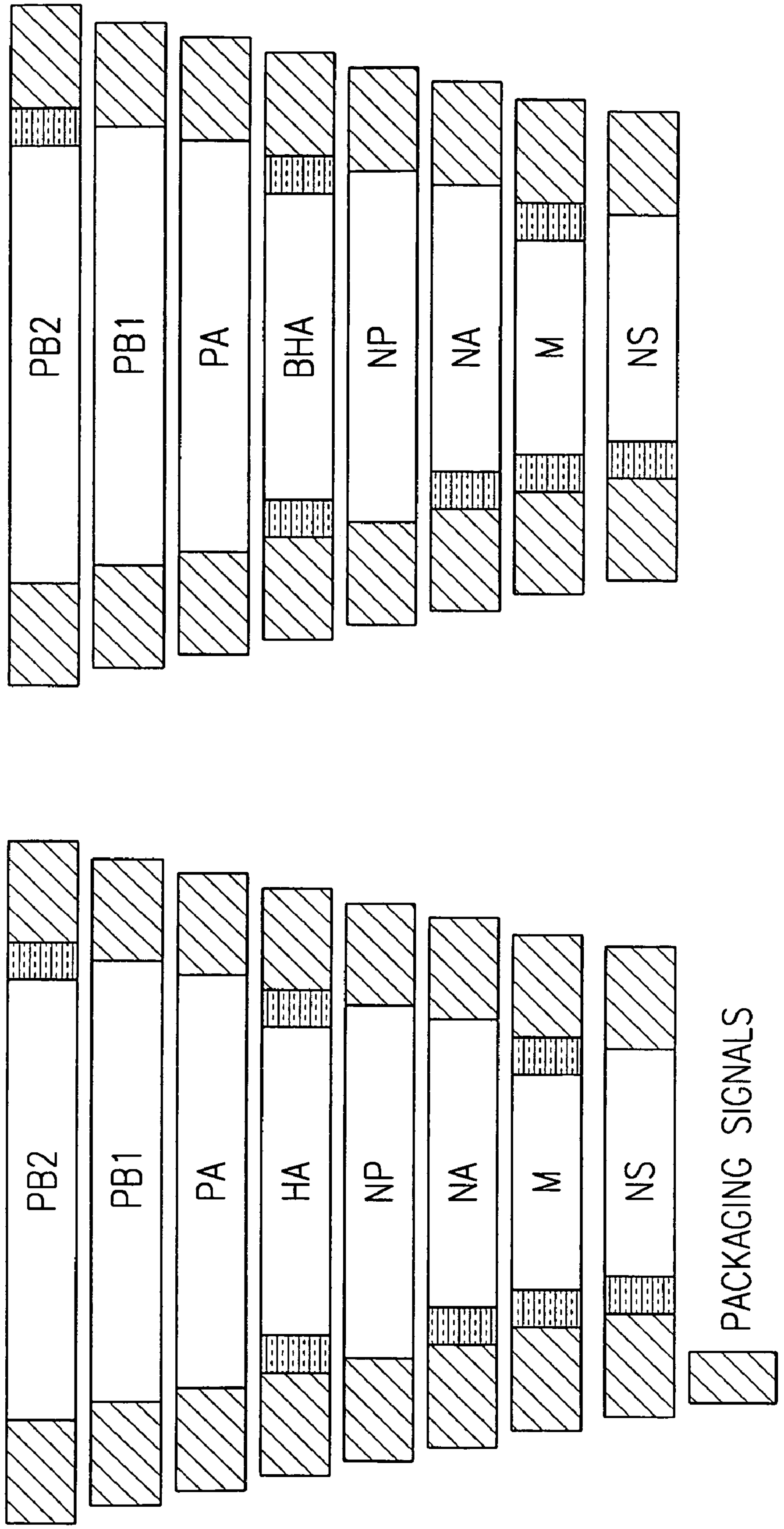
FIG. 12. A) Viral segments for a type A influenza virus and a type A virus whose HA coding sequence is replaced with type B HA. B) Virions for a type A influenza virus and a type A virus whose HA coding sequence is replaced with type B HA.
Figure 12B:
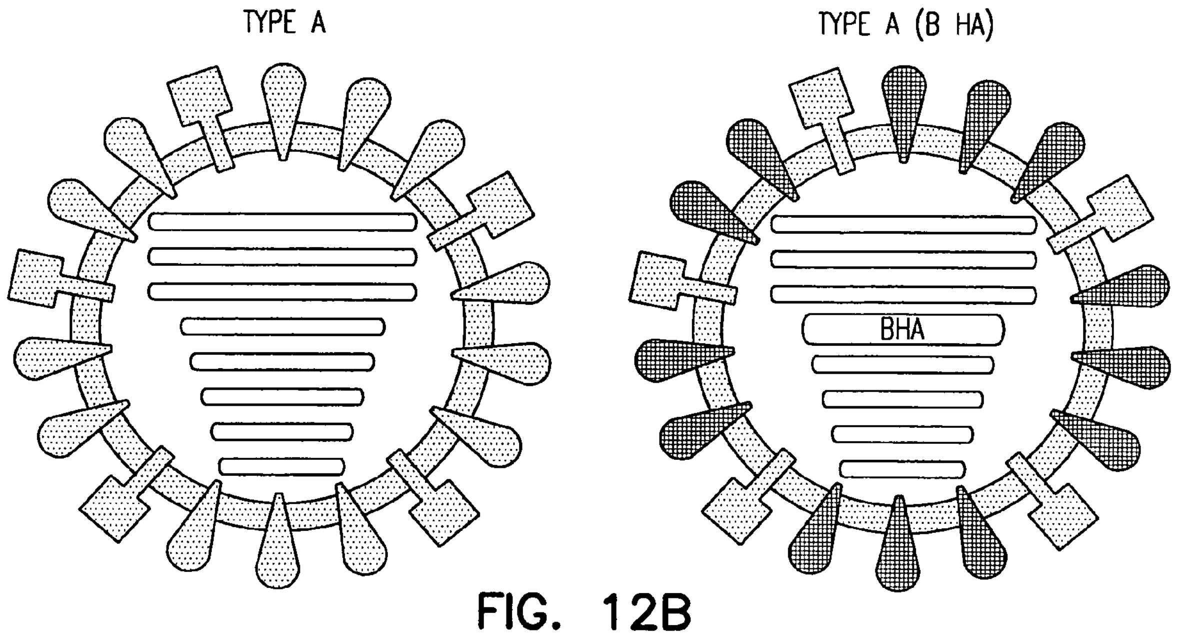

To obtain a true image of the viral contents, electron microscopy tomography was performed (FIG. 11A). An image of virions with a 50 nm thickness was collected. Then, an analysis of one of the virions was conducted and the 3D images of virion content reconstituted. The structures (rods) inside the particle are colored to distinguish each structure (FIGS. 11B-F, showing views from the top, side and bottom). Most of the views for the rods are cut, however, for one view, in which rods were cut across the middle, the entire molecule is shown. Nevertheless, all of the views show inter-rod interactions.

Based on the results summarized above, including data which support that each viral segment contains a unique sequence that is important for incorporation into virions, which likely contributes to the formation of the unique morphologic features of the viral contents, vRNA segments are likely selectively incorporated into influenza virions. This information is useful not only to identify targets for developing antiviral compounds but also for the preparation of attenuated live vaccines as disruption of virus-specific interactions can inhibit viral replication and lead to attenuation.

EXAMPLE 4

Materials and Methods

Cells. 293T human embryonic kidney cells and COS-7 cells were maintained in Dulbecco's modified Eagle's minimal essential medium (DMEM) with 10% fetal calf serum and antibiotics. Madin-Darby canine kidney (MDCK) cells were grown in MEM with 5% newborn calf serum and antibiotics. Cells were maintained at 37° C. in 5% $CO_2$.

Figure 13:
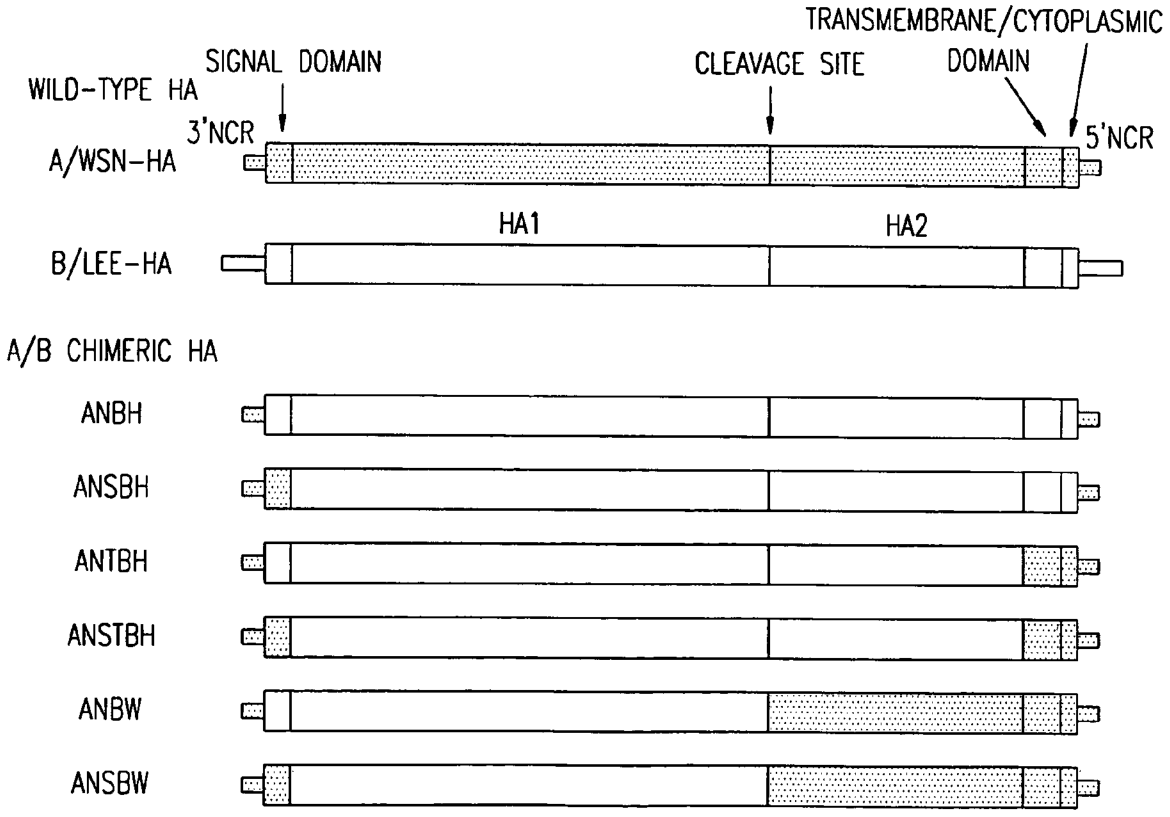
FIG. 13. Diagram of A/B chimeric HA constructs. Chimeric HA constructs were produced between wild-type A/WSN virus HA (pPolI-WSN-HA) and wild-type B/Lee virus HA (pPolI-B-HA) in a pPolI-based plasmid (pHH21) as described in Neumann et al. (1999).

Construction of plasmids. The generation of plasmid constructs for viral RNA production (referred as pPolI) containing the HA genes of wild-type A/WSN/33 (H1N1) (named as pPolI-WSN-HA) and wild-type B/Lee/40 (pPolI-B-HA) viruses flanked by human RNA polymerase I promoter and mouse RNA polymerase I terminator was described in Neumann et al. (1999). A series of A/B chimeric HA pPolI constructs were produced by PCR amplification with primers and ProofStart polymerase (QiAGEN) and subsequent ligation using wild-type HA constructs (FIG. 13). All constructs were sequenced to ensure that the unwanted mutations were not included.

Biologic assays of HAs expressed in cell culture. Each A/B chimeric HA pPolI construct (1 μg) was transfected into COS-7 cells using Trans IT reagent (Mirus) together with the other four pCAGGS-based plasmids (1 μg each) expressing three polymerase subunits (PA, PB1, and PB2) and the nucleoprotein (NP) of A/WSN virus (Neumann et al., 1991). At 48 hours after transfection, cells were treated with *Vibrio cholerae* sialidase (10 U/ml) and TPCK-trypsin (2.5 μg/ml) at 37° C. for 30 minutes. Cells were then fixed with 4% paraformaldehyde and immunostained using anti-B/HA antibody and a commercial ABC detection kit (Vector laboratory). Also, hemadsorption assays were performed to assess the receptor-binding properties of each HA. Briefly, transfected cells were incubated in a 1% chicken red blood cell suspension in phosphate buffered saline (PBS) at room temperature for 30 minutes, and then washed 5 times before observation. Additionally, fusion assays were carried out. Briefly, transfected cells were incubated in HEPES buffer (pH 5.0) at 37° C. for 5 minutes followed by incubation in culture medium for 7 hours. After fixation with cold methanol, fused cells were immunostained as described above.

Reverse genetics. Virus was generated by plasmid-based A/WSN or B/Lee reverse genetics systems as described in Neumann et al. (1999). Viruses with wild-type genotypes produced from plasmids were designated as A/WSN-R or B/Lee-R, respectively, and used as controls for comparison. To produce A/B chimeric viruses, chimeric HA PolI-constructs were used instead of pPolI-WSN-HA. Viruses produced from 293T cells were biologically cloned by limiting dilution once and stock viruses were produced in MDCK cells.

Experimental infection. To test virus pathogenicity, four-week-old female BALB/c mice, anesthetized with sevoflurane, were infected intranasally with A/B chimeric or wild-type viruses ($10^5$ $TCID_{50}$/50 μl). Mortality and body weights were monitored for 14 days after infection. Three days after infection, some of the infected mice were euthanized for determination of virus titers in organs.

To evaluate the vaccine efficacy of each chimeric virus against wild-type challenge, mice were intranasally infected with chimeric or wild-type viruses ($10^3$ $TCID_{50}$/50 μl). Three weeks later, a group of mice was euthanized to obtain sera and tracheal-nasal washes for detecting virus-specific IgA or IgG antibodies. Four weeks after infection, the remaining mice were intranasally challenged under anesthesia with 50 $LD_{50}$ of the wild-type virus (B/Lee-R) and monitored for mortality and body weight for 14 days.

Detection of virus-specific antibody. Serum and tracheal-nasal wash samples were examined for IgA or IgG antibody by an enzyme-linked immunosorbent assay (ELISA) as described in Kida et al. (1982). HI antibodies were also examined using serum samples following treatment with receptor-destroying enzyme (RDEII: Denka Seiken).

Results

Figure 14:
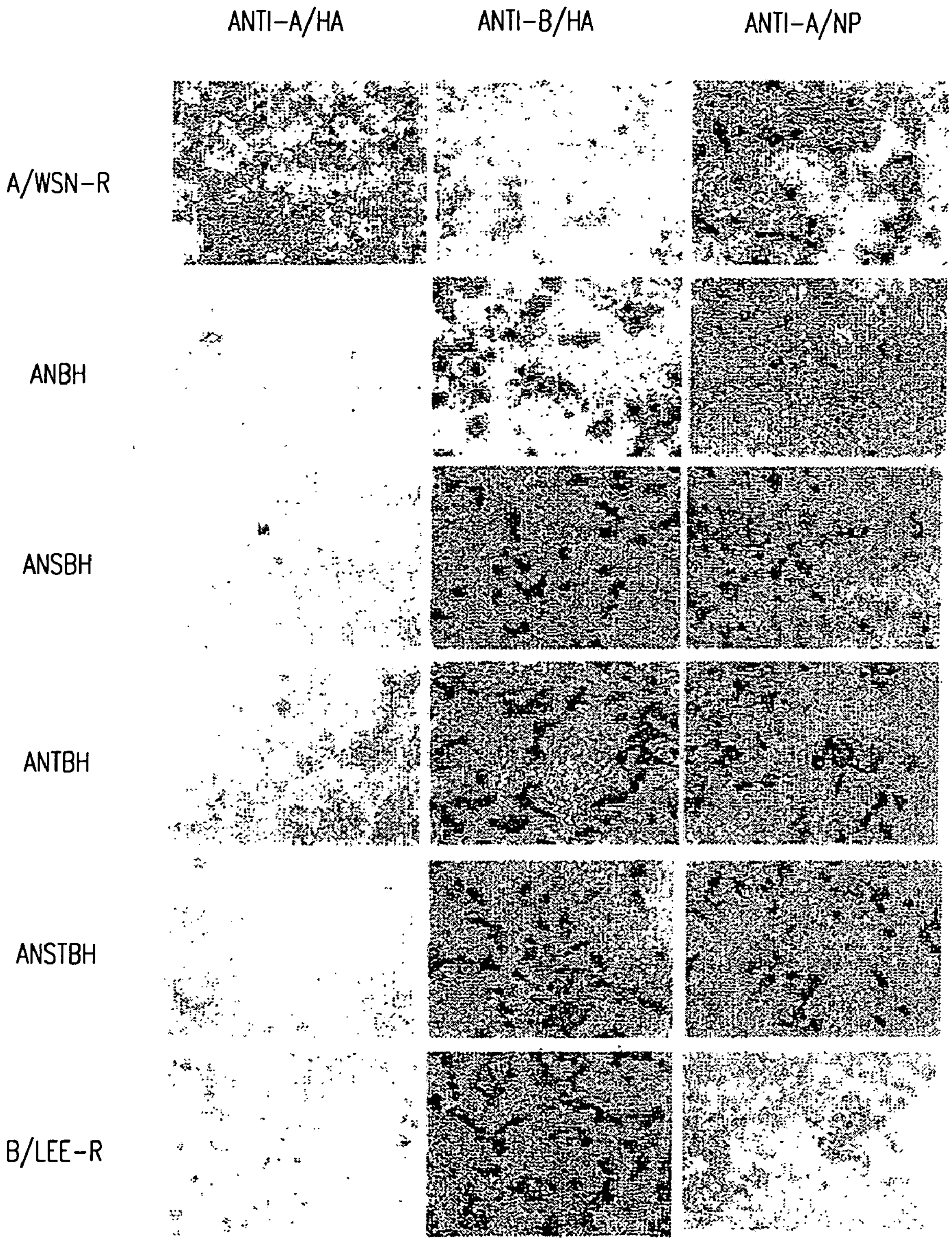
FIG. 14. Expression of type B HA by A/B HA chimeric viruses. MDCK cells infected with each virus were fixed 24 hours post-infection and immunostained with anti-A/HA, anti-B/HA, or anti-A/NP antibodies.

Construction of A/B chimeric HA genes. To determine the compatibility of type B HA with type A viral components, a series of chimeric genes was constructed between A/WSN and B/Lee HA genes (FIG. 14). Since the noncoding sequences in both termini of the RNA segments are likely interchangeable between type A and B viruses for RNA transcription and replication (Crescenzo-Chaigne et al., 1999; Desselberger et al., 1980; Muster et al., 1981), a chimeric HA gene was prepared that contains the noncoding sequences of type A virus and the entire coding sequence from type B virus (FIG. 14A, ANBH). This construct would produce intact type B HA protein. Next, a chimeric gene was prepared in which the signal sequence region of the type B HA coding sequence and the noncoding sequence were changed to that of type A virus (ANSBH). This construct would also produce intact type B HA after removal of the type A signal peptide by the cellular signal peptidase. Similarly, a chimeric gene was prepared in which the sequence encoding transmembrane and cytoplasmic regions of the HA was changed from type B to type A (ANTBH), thus encoding an A/B chimeric HA protein. Another chimeric gene was prepared in which sequences encoding both the signal and transmembrane/cytoplasmic regions were changed from type B to type A (ANSTBH). This construct would produce the same chimeric HA protein as ANTBH after removal of the signal peptide. In addition, a chimera was prepared that contains all the sequences upstream of the region corresponding to the cleavage site from type B and the downstream region from type A virus in the HA coding sequence (ANBW). This construct would produce a chimeric HA protein comprising the HA1 region of type B virus and the HA2 region of type A virus. Finally, a chimeric gene was prepared in which the signal sequence was changed from type B to type A within the ANBW construct, which would result in the same chimeric HA protein as does ANBW.

Biologic properties of A/B chimeric HAs expressed in cell culture. To evaluate the functionality of the chimeric HAs, each pPolI HA construct was transfected into COS-7 cells together with type A virus PA-, PB1-, PB2-, and NP-expressing plasmids. All of the chimeric HA constructs were expressed on the cell surface. To test the receptor-binding activities of these HAs, hemadsorption assays were performed. Prior to the assay, transfected cells were treated with bacterial sialidase to remove terminal sialic acid in HA oligosaccharide side chains, which would interfere with its receptor-binding activity (Luo et al., 1999). ANBH-, ANSBH-, ANTBH-, and ANSTBH-expressing cells hemadsorbed, while those expressing the other two (ANBW and ANSBW) did not (Table 3). Similarly, the former HAs induced cell fusion, while the latter did not. These results indicated that the former HA chimeras were biologically functional, whereas the latter two were not, presumably due to structural alterations. As anticipated from previous reports, functional type B HA was produced from intact wild-type B HA segment by type A polymerase complex and NP (Table 3), confirming the compatibility between type B promoter structures and the type A polymerase complex.

TABLE 3

Properties of A/B chimeric HAs expressed in cells and viruses possessing them.

| HA construct | Property in cell culture[a)]: Cell surface expression | Hemadsorption | Fusion | Generation of virus possessing this gene[b)] | Virus titer in supernatant of transfected cell[b)] ($TCID_{50}$/ml) | Virus titer of the stock[c)] ($TCID_{50}$/ml) |
|---|---|---|---|---|---|---|
| Wild-type HA | | | | | | |
| WSN-HA | + | + | + | + | 3.2 × $10^7$ | 6.3 × $10^7$ |
| B-HA | + | + | + | − | NA[d)] | |
| A/B chimeric HA | | | | | | |
| ANBH | + | + | + | + | 2.0 × 10 | 6.3 × $10^2$ |
| ANSBH | + | + | + | + | 1.1 × $10^2$ | 2.0 × $10^6$ |
| ANTBH | + | + | + | + | 2.0 × $10^4$ | 6.3 × $10^6$ |

TABLE 3-continued

Properties of A/B chimeric HAs expressed in cells and viruses possessing them.

| HA construct | Property in cell culture[a)] Cell surface expression | Hemadsorption | Fusion | Generation of virus possessing this gene[b)] | Virus titer in supernatant of transfected cell[b)] ($TCID_{50}$/ml) | Virus titer of the stock[c)] ($TCID_{50}$/ml) |
|---|---|---|---|---|---|---|
| ANSTBH | + | + | + | + | $1.1 \times 10^6$ | $3.6 \times 10^6$ |
| ANBW | + | − | − | − | NA | |
| ANSBW | + | − | − | − | NA | |

[a)]Each HA construct was transfected in COS-7 cells together with type A polymerase- and NP-expressing plasmids. At 48 hours post-transfection, biologic properties of each HA was assayed.
[b)]Generation of virus possessing the wild-type or chimeric HA gene together with other influenza A virus genes was performed by plasmid-based reverse genetics system. At 48 hours post-transfection, the supernatant of transfected 294T cells was harvested and titrated for infectivity.
[c)]Virus stock was prepared with MDCK cells. Viruses were harvested when cytopathic effects were advanced.
[d)]NA: not available.

Production of viruses with chimeric HAs. To determine whether the chimeric HA genes function during influenza A virus infection, a mutant WSN virus was prepared in which the HA gene was replaced with an A/B HA chimeric gene. Plasmid-based reverse genetics allowed the generation of wild-type virus with a titer of approximately $10^7 TCID_{50}$/ml (Table 3). When pPolI-B-HA was employed instead of pPolI-WSN-HA, no infectious virus was generated. The four chimeric HA constructs that were biologically functional (Table 3) were successfully rescued in infectious type A virus, albeit to different efficiencies, as judged by virus titers in the supernatants of plasmid-transfected cells. The virus possessing the ANBH HA replicated only marginally, while the virus with the ANSTBH HA was produced at the highest efficiency and grew to more than $10^6$ $TCID_{50}$/ml. The other two chimeric HA genes that did not express biologically functional proteins did not support viral growth. The A/B chimeric viruses are designated as ANBH, ANSBH, ANTBH, and ANSTBH viruses.

To confirm that the viruses which were produced indeed contained the type B HA ectodomain, MDCK cells were infected with these viruses and tested for their reactivity with antibodies to the HA of type A or B virus (FIG. 14). Cells infected with viruses containing chimeric HA constructs reacted with anti-B/HA as well as anti-A/NP antibodies, but not with anti-A/HA antibody, confirming that these viruses contain type B HA ectodomains.

Figure 15:
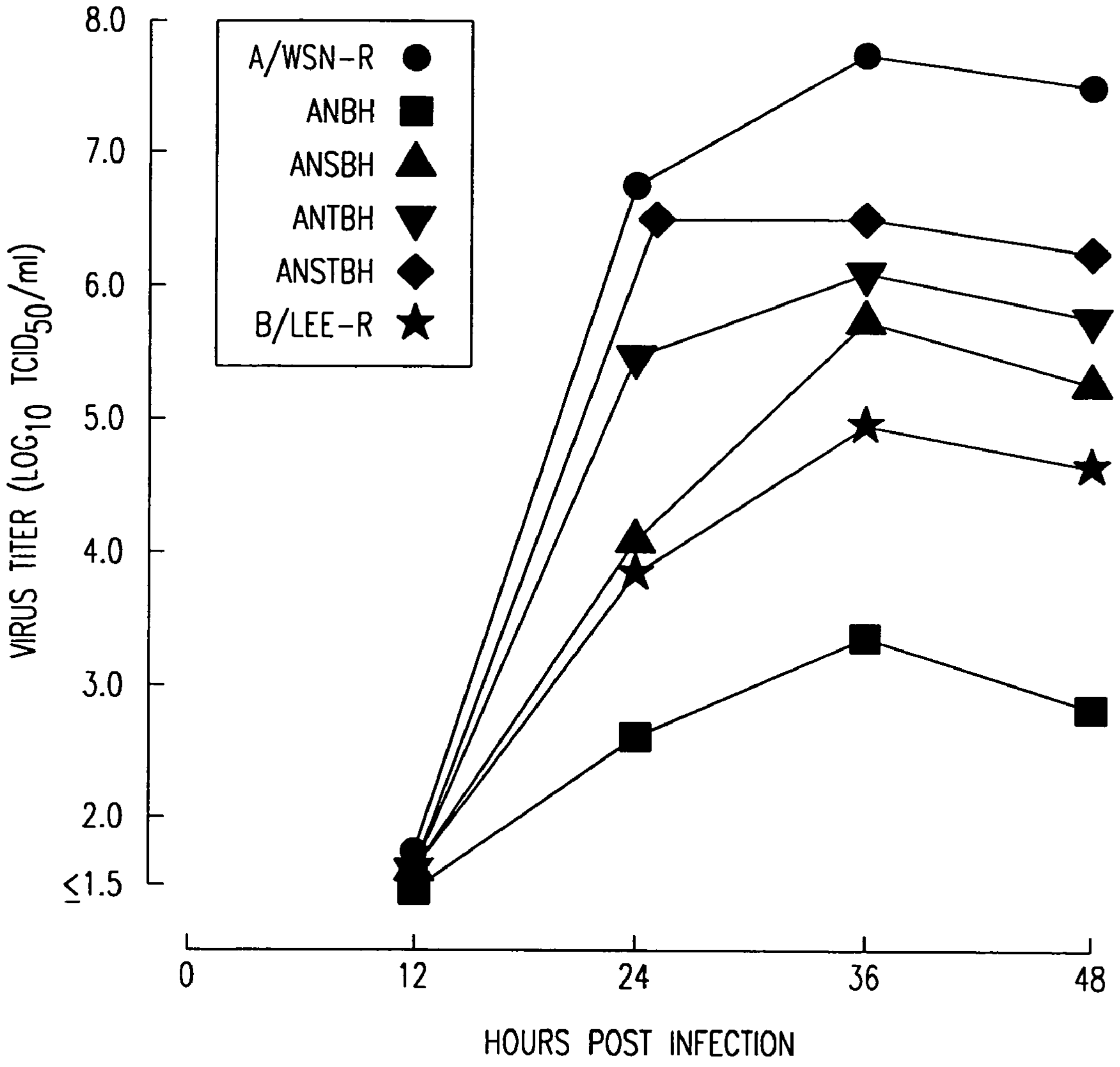
FIG. 15. Growth properties of A/B HA chimeric viruses. MDCK cells were infected with each virus at an MOI of 0.01 $TCID_{50}$ and monitored for virus growth. One of two independent experiments with similar results is shown.

Growth characteristics of A/B chimeric viruses in cell culture. To determine the replicative properties of the A/B HA chimeric viruses, cells were infected with the viruses at an MOI of 0.01 and the resulting viruses examined for their growth kinetics (FIG. 15). Although none of the viruses with the chimeric HAs grew better than wild-type A virus, ANSTBH and ANTBH chimeric viruses grew to nearly $10^6$ $TCID_{50}$/ml. Unlike both type A and B viruses, all of these chimeric viruses formed pinpoint plaques, which could be detected only with immunostaining (data not shown).

Replication of the A/B chimeric viruses in mice. The restricted replication of the A/B chimeric viruses in cell culture suggested that these viruses may be attenuated in vivo. Therefore, mice were inoculated intranasally with A/B HA chimeric viruses ($10^5$ $TCID_{50}$/50 μl). ANBH virus was not tested since the titer of the stock was too low (approximately $10^3$ $TCID_{50}$/ml). None of the other three chimeric viruses tested were lethal to mice, whereas the same dose of the wild-type A virus killed all infected mice while the same dose of the wild-type B virus killed seven of eight infected mice (Table 4). Chimeric viruses were recovered from lungs and nasal turbinates on day 3 post-inoculation, indicating that these viruses replicated in mice. Interestingly, replication of the chimeric viruses was more restricted in lungs, and less restricted in nasal turbinates, when compared with those of wild-type viruses. This suggests a possible link between virus replication level in lung and lethality. Mice infected with ANTBH and ANSTBH chimeric viruses lost weight albeit to a lesser extent as compared with those with wild-type A viruses. Together, these data indicate that A/B HA chimeric viruses are attenuated in mice.

TABLE 4

Pathogenicity of A/B chimeric viruses in mice.

| Virus[a)] | Replication in organs[b)] Nasal turbinates | Lungs | Change of body weight (%)[c)] Day 5 | Day 14 | Lethality (%) (No. of dead/no. of tested) |
|---|---|---|---|---|---|
| Wild-type virus | | | | | |
| A/WSN-R | 5.0 ± 0.3 | 8.2 ± 0.1 | −27.4 ± 1.1 | NA[c)] | 100 (8/8) |
| B/Lee-R | 4.7 ± 0.1 | 5.6 ± 0.1 | −19.3 ± 7.9 | NA | 87.5 (7/8) |
| A/B chimeric virus | | | | | |
| ANSBH | 4.0 ± 0.3 | 2.8 ± 0.3 | 2.6 ± 1.0 | 4.6 ± 1.2 | 0 (0/8) |
| ANTBH | 5.3 ± 0.3 | 4.9 ± 0.1 | −17.3 ± 0.7 | −8.3 ± 0.4 | 0 (0/8) |

TABLE 4-continued

Pathogenicity of A/B chimeric viruses in mice.

| Virus[a)] | Replication in organs[b)] Nasal turbinates | Lungs | Change of body weight (%)[c)] Day 5 | Day 14 | Lethality (%) (No. of dead/no. of tested) |
|---|---|---|---|---|---|
| ANTSTBH | 5.3 ± 0.4 | 4.6 ± 0.1 | −20.9 ± 0.3 | −6.2 ± 8.8 | 0 (0/8) |
| Control (PBS)[d)] | NA | NA | 2.9 ± 1.3 | 7.1 ± 0.2 | 0 (0/8) |

[a)]Mice were intranasally inoculated with virus ($10^6$ $TCID_{50}$) and monitored for 14 days. Change of body weight was expressed as mean value ± standard deviation (SD (n = 3).
[b)]Virus titers were determined in organs at 3 days post-inoculation and expressed as mean value ± SD (n = 3) of $\log_{10}TCID_{50}/g$.
[c)]NA: not available.
[d)]Control mice were mock-inoculated with phosphate-buffered saline (PBS).

Figure 16A:
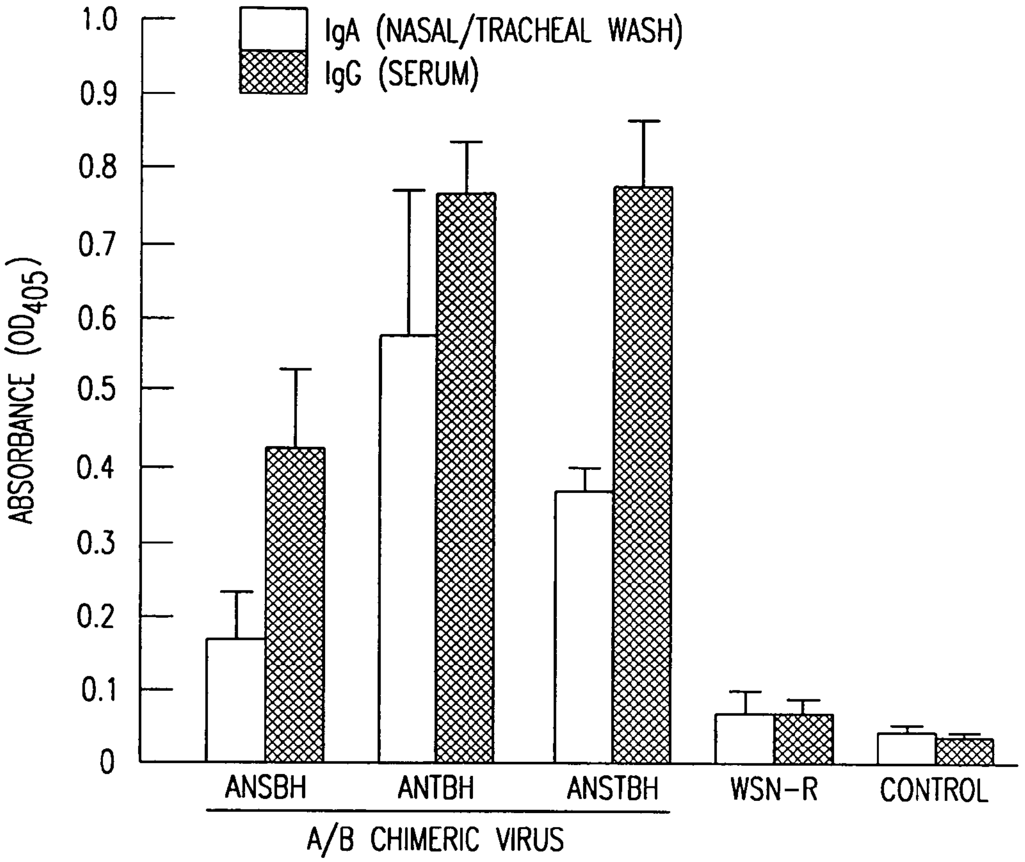
FIG. 16. Antibody response to type B virus in mice inoculated with A/B HA chimeric viruses. A) Mice (3 mice/group) were intranasally inoculated with each virus ($10^3$ $TCID_{50}$). Three weeks post-inoculation, nasal/tracheal washes and serum samples were taken from mice and tested for anti-B virus specific IgA (nasal/tracheal wash) or IgG (serum) antibodies in an ELISA assay. B) HI titers in serum samples were also tested. Each bar indicates individual mouse infected with the chimeric virus.
Figure 16B:
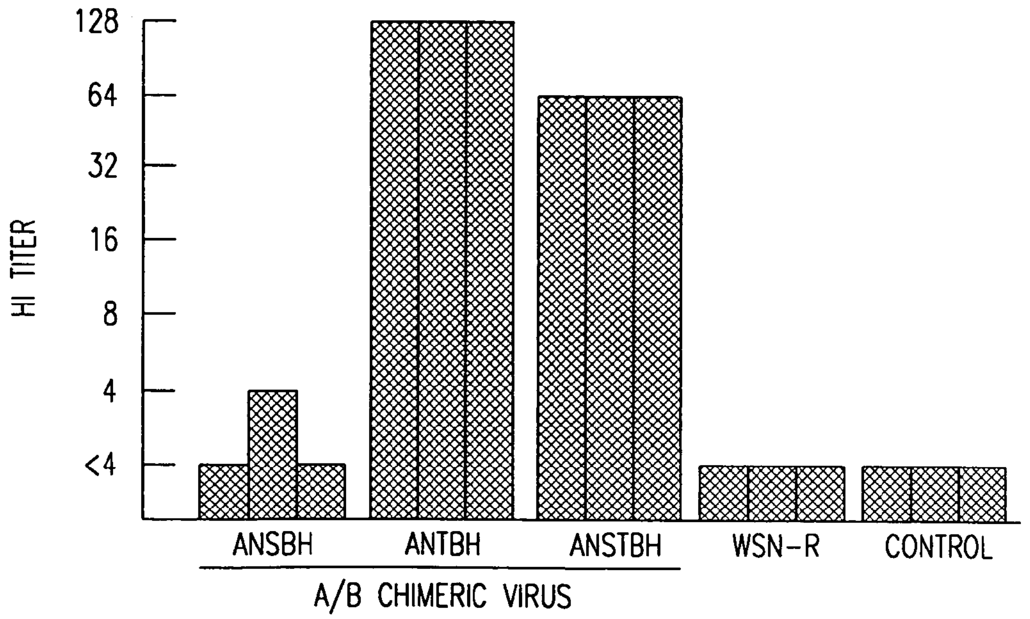

Protection of mice immunized with the A/B HA chimeric viruses upon wild-type virus infection. Since the A/BHA chimeric viruses express an HA ectodomain that is derived from type B virus, it was anticipated that these viruses would provide a protective immune response to wild-type B virus infection. Prior to challenge experiments, it was determined whether anti-B antibodies are elicited in mice following infection with the chimeric viruses. At three weeks post-inoculation, type B virus-specific IgA in nasal/tracheal wash samples and IgG antibodies in serum samples from mice infected with chimeric viruses were detected by an ELISA test (FIG. 16A). HI antibodies were also detected in serum samples from A/B HA chimeric virus-infected mice (FIG. 16B). Thus, specific antibody responses were demonstrated in all mice infected with the chimeric viruses, although ANSBH virus elicited a less efficient immune response.

The chimeric virus-immunized mice were challenged with $50LD_{50}$ of the wild-type B virus 4 weeks post-immunization (Table 5). All the mice survived after challenge, whereas all of the control mock-immunized mice died and only 2 out of 8 mice immunized with WSN virus at a sublethal dose ($10^3$ $TCID_{50}$) survived upon challenge with wild-type B virus, indicating a specific protective effect of chimeric virus immunization against wild-type B virus infection. In addition, type B virus was not recovered from nasal turbinates or lungs of mice preimmunized with chimeric viruses, with the exception of one mouse that received ANSBH virus 3 days post-challenge (data not shown).

TABLE 5

Protection of mice immunized with A/B chimeric viruses against wild-type B virus challenge

| Virus used for immunization[a)] | Post-challenge[b)] Change of body weight (%) Day 5 | Day 14 | Survival rate (%) (No. of survivors/ no. of tested) |
|---|---|---|---|
| Wild-type virus | | | |
| A/WSN-R | −17.5 ± 3.6 | NA[c)] | 25 (2/8) |
| B/Lee-R | 1.8 ± 0.9 | 1.4 ± 0.6 | 100 (8/8) |
| A/B chimeric virus | | | |
| ANSBH | −5.6 ± 0.8 | −0.7 ± 0.7 | 100 (8/8) |
| ANTBH | 0.9 ± 0.9 | 1.9 ± 0.9 | 100 (8/8) |

TABLE 5-continued

Protection of mice immunized with A/B chimeric viruses against wild-type B virus challenge

| Virus used for immunization[a)] | Post-challenge[b)] Change of body weight (%) Day 5 | Day 14 | Survival rate (%) (No. of survivors/ no. of tested) |
|---|---|---|---|
| ANSTBH | 1.5 ± 0.2 | 2.9 ± 0.7 | 100 (8/8) |
| Control (PBS)[d)] | −20.8 ± 0.5 | NA | 0 (0/8) |

[a)]Mice were intranasally infected with each virus listed
[b)]Four weeks post-immunization, mice were intranasally challenged with wild-type B/Lee-R virus ($50LD_{50}$) and monitored for 14 days after challenge. Change of body weight was expressed as mean value ± SD (n = 3).
[c)]NA: not available
[d)]Control mice were mock-immunized with PBS and challenged.

Discussion

As described herein, for the first time, an influenza virus was generated which possesses type B, instead of A, HA in the background of type A virus, thus possessing both type A and B viral proteins. What is essential for the generation of A/B HA chimeric viruses? The chimeric genes must be transcribed and replicated to be maintained in virions. Although conserved among the same virus type, terminal sequences in both ends of the noncoding regions, which contain promoter sequences needed for RNA transcription and replication (Luytjes et al., 1989), differ between type A and B RNA segments (Crescenzo-Chaigne et al., 1999; Desselberger et al., 1980). However, a previous study has shown that a reporter gene flanked by the noncoding sequence of type B virus NS segment was transcribed and replicated by a type A polymerase (Muster et al., 1991). Furthermore, a chimeric A/B influenza virus (NA/B-NS) containing a chimeric gene comprising the coding sequence of type A virus NA and the noncoding sequence of type B virus NS was produced (Muster et al., 1991). These data indicated that the type A polymerase complex recognized the promoter sequence of the type B NS gene, albeit to a lesser extent than the homologous promoter of type A virus genes.

The noncoding sequence of each RNA segment includes two structural regions: terminal sequences that are conserved among all eight RNA segments and inner segment-specific sequences. Since promoter activity is mainly determined by the former region (Portela et al., 1999), all type B gene segments are likely be transcribed and replicated by the type A polymerase complex. In fact, this concept is supported by data showing that type B HA was expressed in cells cotransfected with pPolI-B-HA containing type B noncoding regions and type A polymerase complex- and NP-expressing plasmids (Table 3). Thus, failure to generate a virus containing an intact type B HA segment, i.e., an HA intertypic reassortant, cannot be explained by the lack of RNA transcription and replication.

The restriction of the generation of the chimeric virus may originate at the level of RNA segment incorporation into virions; for virus generation, the chimeric segment must be packaged into virions. Although the noncoding region of type A NS segment was reported to contain an RNA packaging signal (Luytjes et al., 1989), the packaging mechanism of influenza virus RNA segments has not been fully elucidated. The sequences or structural features of the RNA segments required for virion incorporation were largely unknown; however, it was recently shown that type A NA RNA segment possesses its virion incorporation signals at both ends of the coding regions (Fujii et al., 2002 and Example 2). In this study, ANSBH virus replicated more efficiently than ANBH virus (FIG. 14 and Table 3). Since the HA proteins expressed in these two viruses should be identical, the difference in replication efficiency may result from RNA packaging efficiency. That is, a structural feature required for efficient RNA packaging may exist in the region encoding the signal sequence of the HA. Similarly, this may also explain the difference in replicative efficiency between ANTBH and ANSTBH viruses, which also express identical HA proteins. In fact, the packaging signals for the type A HA segment reside at both ends of the coding regions (unpublished data). Interestingly, a chimeric NA gene containing the noncoding sequences of type A virus NA and the coding sequence of type B NA was not rescued into type A virus (Ghate et al., 1999). This failure may be explained by lack of a type A NA coding region containing an RNA packaging signal, consistent with the recent finding mentioned above (Fujii et al., 2002).

There may also be critical interactions at the protein level for the generation of A/B HA chimeric viruses; chimeric proteins must be packaged into virions and must be functional for virus replication. The type B NA protein supplied in trans can replace the function of a type A NA and be incorporated into type A virions, supporting multiple cycles of replication of a NA-defective type A virus in cell culture (Ghate et al., 1999). However, as discussed above, a type A virus containing a type B NA was not generated. Although chimeric A/B HA viruses were generated, they were attenuated as compared with the wild-type virus. This attenuation may originate from a suboptimal balance between receptor-binding activity of type B HA and the sialidase activity of type A NA. In addition, replacement of the signal peptide and/or transmembrane/cytoplasmic domains in the HAs may have altered their structure. For example, the transmembrane/cytoplasmic domains in HA may interact with other viral components such as M1 leading to efficient virion assembly (Ali et al., 2000; Cenami et al., 1996; Jin et al., 1997; Zhang et al., 2000). Thus, the inability to generate type A virus possessing intact type B RNA segments or vice versa may be explained by restriction at the level of RNA segment incorporation or the level of functional interaction of proteins or both.

The A/B HA chimeric viruses were attenuated in mice with restricted replication in lung and conferred protective immunity to mice against wild-type B virus infection, suggesting a novel approach for the development of influenza vaccines. Currently, subcutaneous administration of trivalent inactivated influenza vaccines is the standard worldwide, yet their efficacies are suboptimal. This is mainly due to unsatisfactory induction of mucosal immunity in the upper respiratory tract where influenza viruses initially invade (Wavening et al., 2001). Thus, these vaccines do not prevent viral infection, although they lessen the severity of the illness. Unlike inactivated vaccines, live vaccines induce both mucosal and cytotoxic T-cell immune responses. The study described herein suggests that chimeric manipulation of the HA gene could control virus attenuation to various degrees. Thus, this approach would permit the production of live vaccine strains with an appropriate balance between attenuation and immunogenicity. Alternatively, the A/B chimeric HAs can be incorporated into cold-adapted influenza A virus whose attenuating mutations are well-characterized (Maassab et al., 1999). Current cold-adapted vaccines are mixtures of type A and type B viruses. Potentially, interference between the two viruses affects vaccine efficacy, although this problem has been addressed by adjustment of the ratio of viral doses. A type A virus with the A/B chimeric HA would allow the production of live influenza vaccines based on a single attenuated virus rather than two attenuated viruses, eliminating potential interference between type A and B viruses.

Thus, in contrast to a live attenuated vaccine having a mixture of type A and B viruses, with limited information on the attenuating mutations for the type B vaccine strain, a virus that contains type B HA and NA in the background of type A virus can be produced. This approach allows the production of vaccines based on a master vaccine strain with well-defined attenuating mutations for the expression of type A as well as type B HA and NA. Moreover, knowledge of the packaging signals for viral segments also promotes development of improved live attenuated influenza vaccines.

EXAMPLE 5

Materials and Methods

Cells and virus. 293T human embryonic kidney cells (a derivative of the 293 line into which the gene for simian virus 40 T antigen was inserted) were maintained in Dulbecco's modified Eagle medium supplemented with 10% fetal calf serum (FCS). For baby hamster kidney (BHK), Chinese hamster ovary (CHO), and Madin-Darby canine kidney (MDCK) cells, DMEM containing 5% FCS and MEM containing 10% and 5% newborn calf serum were used, respectively. All cells were maintained at 37° C. in 5% $CO_2$. A/WSN/33 (H1N1) (WSN) virus was generated by reverse genetics as described in Neumann et al. (1999) and propagated in MDCK cells. VSV Indiana strain generated by reverse genetics was propagated in BHK cells.

Reverse genetics. For generation of influenza virus-like particles (VLPs) and mutant influenza A viruses, plasmids possessing the cDNA of WSN viral genes under the control of the human RNA polymerase I promoter and the mouse RNA polymerase I terminator (referred to as PolI plasmids) and the eukaryotic protein expression vector pCAGGS/MCS (controlled by the chicken P-actin promoter) were used. Briefly, PolI plasmids and protein expression plasmids were mixed with a transfection reagent, Trans IT LT-1 (Panvera, Madison, Wis.), incubated at room temperature for 15 minutes, and added to $1\times10^6$ 293T cells cultured in Opti-MEM I (GIBCO/BRL). Six hours later, the DNA-transfection reagent mixture was replaced with Opti-MEM I containing 0.3% BSA and 0.01% FCS. Forty-eight hours later, VLPs or mutant influenza A viruses in the supernatant were harvested. Transfectants generated in this study all contain a mutant HA vRNA segment together with other vRNA segments of WSN virus and are designated by the name of the mutant HA vRNA segment (e.g., a VLP containing the HA(0)GFP(0)RNA segment is designated the HA(0)GFP(0) VLP).

Construction of plasmids. pPolIHA(0)GFP(0) was used to produce negative-sense RNA containing the 3' noncoding region of HA vRNA, the complementary coding sequence of enhanced green fluorescent protein (GFP, Clontech), and the 5' noncoding region of HA vRNA. Briefly, the GFP gene was amplified by PCR with primers containing the BsmBI sites and the 3' or 5' noncoding sequence of HA, digested with BsmBI, and cloned into the BsmBI site of the PolI plasmid. Introduction of this plasmid into cells results in an RNA containing the GFP-coding sequence in negative-sense orientation flanked by 5' and 3' noncoding regions HA vRNA.

pPolIHA(468)GFP(513) was made as follows: pPolIHA for the production of WSN vRNA was first amplified by inverse PCR using back-to-back primers Bam500R (5'-GCG-GATCCTCCCCTATGGGAGCATGATAC-3'; SEQ ID NO:6) and XbaI218F (5'-GCTCTAGAAACTCTGTTATC-GAGAAAATG-3'; SEQ ID NO:7). The PCR product was digested with BamHI and XbaI, and then the GFP gene was cloned into the BamHI site and XbaI site. The resultant plasmid, pPolIHA(468)GFP(513), was used for the production of negative-sense RNA, containing the 3' noncoding region and 468 bases of the 3' coding region of HA vRNA, the GFP coding sequence, 513 bases of the 5' coding region and the 5' noncoding region of HA vRNA. A series of HA deletion mutants was also produced by inverse PCR in the same manner. The mutants were designated according to the number of nucleotides derived from the HA coding region, e.g., the HA(9)GFP(80) RNA segment contains the 3' HA noncoding region, 9 nucleotides from the HA coding sequence corresponding to the N-terminal region, GFP open reading frame, 80 nucleotides from the HA coding sequence corresponding to the C-terminal region, and the 5' HA noncoding sequence. All plasmid constructs were sequenced to ensure that unwanted mutations were not introduced by PCR.

pPolIHA(0)VSVG(0), which was used to produce negative-sense RNA containing the 3' noncoding region of HA vRNA, the complementary coding sequence of V SVG, and the 5' noncoding region of HA vRNA, was produced by PCR. Briefly, the VSV G gene was amplified by PCR using pCAGGS-VSVG as a template and primers containing the BsmBI sites and the 3' or 5' noncoding sequence of HA. The PCR product was then digested with BsmBI, and cloned into the BsmBI site of the pHH21 vector. pPolIHA(9)VSVG(80) was made by cloning the coding sequences of VSV G into the BamHI site and the XbaI site of pPolIHA(9)GFP(80). pPolINA(183)GFP(157), which contains the 3' noncoding ends of NA vRNA and a complementary sequence encoding a fusion protein possessing 61 N-terminal NA codons and GFP, two consecutive stop codons (TAA-TAG), and 185 bases of the 5' end of NA vRNA, was produced as follows. The region corresponding to nucleotides 203 to 1109 (positive sense) of WSN NA gene in pT7Blue-NA was first replaced with a BglII site by inverse PCR. The GFP gene was then cloned into this BglII site and StuI site at position 1226 (in the wild-type NA gene) in frame with the NA protein. The NA(183)GFP(157) gene was then inserted into the BsmBI site of a PolI plasmid, pHH21.

pPolINA(183)GFP(157)Met(−), used for the production of negative-sense NA(183)GFP(157)Met(−) RNA, which lacks the start codon for the NA protein, was generated as follows. The ATG initiation codon and another ATG at the fifteenth codon of the NA(183)GFP(157) gene in pPolINA(183)GFP (157) was change to GCG by in vitro site directed mutagenesis (GeneEditor, Promega). The resultant construct, pPolINA(183)GFP(157)Met(−), contains the 3' NA noncoding region (19 nucleotides), 183 nucleotides corresponding to the N-terminal NA coding region, the GFP open reading frame, two consecutive stop codons (TAA-TAG), 157 nucleotides corresponding to the C-terminal NA coding region, and the 5' NA noncoding region (28 nucleotides), under the control of the human RNA polymerase I promoter and the mouse RNA polymerase I terminator.

Immunostaining assay. Sixteen hours after infection with influenza VLPs, cells were washed twice with phosphate-buffered saline (PBS) and fixed with 3.7% formaldehyde (in PBS) for 20 minutes at room temperature, followed by treatment with 0.1% TritonX-100 and processed. To examine the efficiency of VLP generation, $10^6$ cells were incubated with 0.1 ml of the culture supernatant of plasmid-transfected 293T cells and the number of NP-positive cells, as detected by the immunostaining assay, was recorded at 16 hours post-infection.

Western blotting. The VLPs or mutant viruses were spun down for 1.5 hours at 50,000×g at 4° C. Concentrated VLPs or viruses were resuspended in lysis buffer (0.6 M KCl, 50 mM Tris-HCl, pH 7.5, 0.5% Triton X-100). The lysates were placed on 15% SDS-polyacrylamide gels, electrotransferred to a polyvinylidene difluoride (PVDF) membrane, blocked overnight at 4° C. with 5% skim milk in PBS, and incubated with anti-WSN virus polyclonal antibody, anti-HA monoclonal antibody, or anti-VSVG monoclonal antibody for 1 hour at room temperature. The membrane was washed three times with PBS containing 0.05% Tween-20. Bound antibodies were detected with a VECTASTAIN ABC kit (Vector) and Konica immunostaining kit (Konica).

Northern hybridization. vRNA present in 293T cells transfected with PolI plasmids was extracted with the Isogen RNA extraction kit (Nippon Gene, Tokyo, Japan) at 24 hour post-transfection. RNAs were glyoxalated in glyoxal/DMSO/phosphate buffer at 50° C. for 1 hour and separated by electrophoresis on 1.0% agarose gel in 10 mM phosphate buffer (pH 7.0). RNAs were blotted onto nylon membrane and hybridized with an oligonucleotide probe complementary to the GFP sequence (ATGGCCGACAAGCAGAAGAACG-GCATCAAGG; SEQ ID NO:8) (10 pmol), which was labeled using a DIG Oligonucleotide Tailing Kit (Roche) at 37° C. for 30 minutes. Hybridization was done using the GFP probe in Easy Hyb (Roche) overnight at 42° C. The RNA bands were detected by using DIG Nucleic Acid Detection Kit (Roche). Briefly, the hybridized membrane was washed with a wash buffer (0.1 M maleic acid, 0.15 M NaCl, 0.3% Tween20, pH 7.5), blocked with 1% Blocking Reagent for 30 minutes at room temperature, and incubated with anti-DIG antibody (1:5000) conjugated with alkaline phosphatase for 30 minutes at room temperature. The membrane was then washed with the wash buffer and incubated with nitroblue tetrazolium chloride/5-bromo-4-chloro-3-indolyl-phosphate (NBT/BCIP) in the detection buffer (0.1 M Tris-HCl, 0.1 M NaCl, pH 9.5) at room temperature in the dark. The RNA bands were detected by using DIG Nucleic Acid Detection Kit (Roche). Control RNA was extracted from mock-transfected 293T cells.

Replicative properties of transfectant viruses. BHK, CHO, or MDCK cells in duplicate wells of 24-well plates were infected with a virus, overlaid with MEM medium containing 0.01% FCS, and incubated at 37° C. At different times, supernatants were assayed for infectious virus in plaque assays on MDCK cells.

Results

Figure 17:
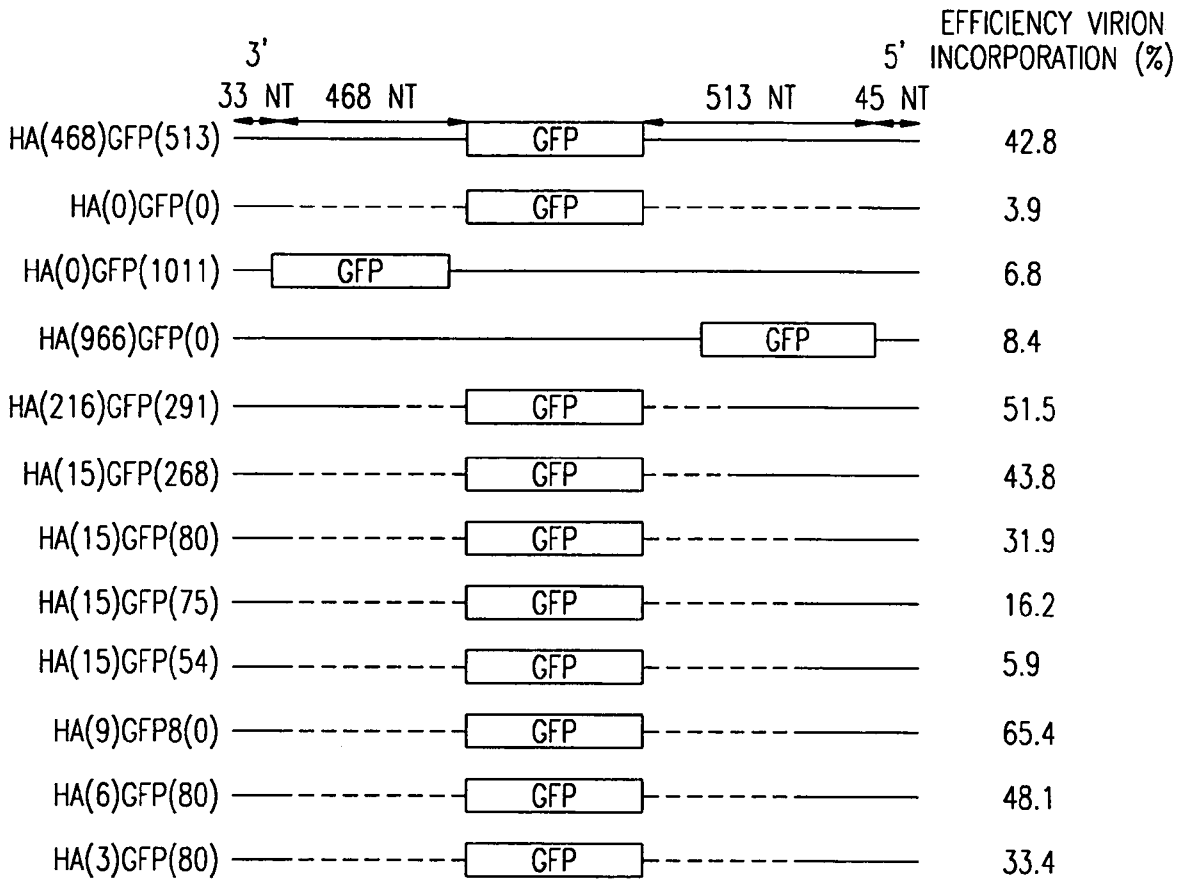
FIG. 17. Schematic diagram of mutant HA vRNAs and their efficiency of virion incorporation. All mutant HA RNAs are shown in negative-sense orientation. Each mutant contains the GFP open reading frame (inserted in-frame with the HA open reading frame) flanked by a stop codon, 33 nucleotides of the 3' noncoding region and 45 nucleotides of the 5' noncoding region of HA vRNA (black bars). The mutants were designated according to the number of nucleotides derived from the HA coding regions. The HA coding regions are shown as grey bars. The horizontal broken line indicates a deletion. The lengths of the regions are not to scale. The efficiency of incorporation of mutant HA vRNA into VLPs was determined by dividing the number of cells expressing GFP with that of cells expressing NP in the VLP-infected cells after fixing cells 16 hours postinfection.

The coding region of HA vRNA was required for the incorporation of the HA segment into virions. To determine whether the coding regions of HA vRNA are needed for its virion incorporation as for NA vRNA, two plasmids were constructed: pPolIHA(0)GFP(0) containing only the 3' and 5' noncoding regions of HA vRNA and the GFP coding sequence, and pPolIHA(468)GFP(513) in which the GFP coding sequence was inserted into the HA gene in-frame after deleting the HA sequence at nucleotide positions 500-1218 (in positive sense orientation) (FIG. 17). The latter construct possesses the 3' HA noncoding region (33 nucleotides), 468 nucleotides corresponding to the N-terminal coding region, the GFP open reading frame with a stop codon, 513 nucleotides corresponding to the C-terminal HA coding region, and the 5' HA noncoding region (45 nucleotides). The resultant fusion protein contains the N-terminal 156 amino acids of the HA and the entire GFP sequence.

Figure 18:
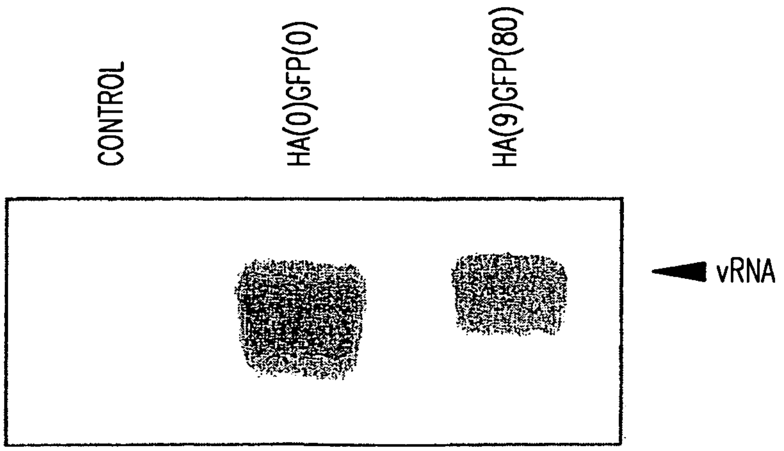
FIG. 18. vRNA levels in 293T cells transfected with plasmids expressing mutant HA vRNAs. 293T cells were transfected with pPolIHA(0)GFP(0) or pPolIHA(9)GFP(80) and plasmids expressing PA, PB1, PB2, and NP.

To generate VLPs possessing these mutant HA vRNAs, 293T cells were transfected with pPolIHA(0)GFP(0) or pPolIHA(468)GFP(513), and 7 RNA PolI plasmids for the production of the remaining influenza viral RNA segments and protein expression plasmids for nine viral proteins (i.e., PA, PB1, PB2, NP, HA, NA, M1, M2, and NS2). Forty-eight hours post-transfection, VLPs in the supernatants of 293T cell cultures were harvested and used to infect MDCK cells. Since the resultant VLPs possessed mutant HA, they expressed GFP and all viral proteins except HA. Consequently, no infectious progeny virus was generated (data not shown). The efficiency of virion incorporation of mutant HA vRNA was determined by dividing the number of cells expressing GFP (i.e., the number of VLPs that possessed the segment encoding GFP gene) with that of cells expressing NP (i.e., the number of all infectious VLPs) at 16 hours post-infection. The titer of all infectious VLPs in the culture supernatant of 293T cells transfected with pPolIHA(468)GFP (513) (i.e., the number of NP-positive cells) was $7.4\times10^5$ infectious VLPs/ml and the titer of VLPs containing HA(468) GFP(513) RNA (i.e., the number of GFP-positive cells) was $3.2\times10^5$ VLPs/ml. These results indicated that 42.8% of all infectious VLPs generated harbored mutant HA vRNA (FIG. 18). By contrast, only 3.9% of VLPs possessed the HA(0) GFP(0)RNA segment (FIG. 18). These results suggested that the coding regions of HA vRNA are required for the incorporation of HA segment into influenza virions.

Both the 3' and 5' ends of the coding region of HA vRNA are important for the incorporation of HA segment into virions. Previously, it was shown that the 3' end of the NA vRNA coding region plays a more crucial role in virion incorporation than does the 5' end. Thus, it was determined whether the 3', 5', or both ends were important for virion incorporation of the HA vRNA segment. To address this issue, the HA(0)GFP (1011) gene was prepared, which lacked the 3' terminus of the HA vRNA coding region, and the HA(966)GFP(0) gene, which lacked the 5' terminus of the HA vRNA coding region (FIG. 17), and virion incorporation of these HA vRNAs examined as described above. Although the amounts of both vRNAs in plasmid-transfected cells were comparable to that of HA(468)GFP(513) vRNA (data not shown), the efficiency of segment incorporation of both HA(0)GFP(1011) and HA(966)GFP(0) was only 6.8% and 8.4%, respectively (FIG. 17), indicating that both the 3' and 5' termini of the HA vRNA coding region played an important role in virion incorporation of HA segment.

To further define the critical region in HA vRNA for its incorporation into virions, a series of VLPs were generated, which possess truncated HA vRNAs with further deletion in the 3' and/or 5' coding region (FIG. 17). The incorporation efficiency of mutant HA vRNA into VLPs was then determined. Since further deletion in the 3' end leaving only 15 nucleotides and the 5' end leaving 268 nucleotides did not affect the efficiency of HA vRNA incorporation (compare HA(468)GFP(513) with HA(15)GFP(268)), additional deletion constructs were prepared using pPolIHA(15)GFP(268), which possesses 15 nucleotides of the 3' end and 268 nucleotides of the 5' end of the HA coding region. Although the extent of vRNA incorporation was reduced gradually as the extent of deletions increased, 80 nucleotides in the 5' HA coding region seemed minimally required for efficient virion incorporation of HA vRNA (compare HA(15)GFP(80) with HA(15)GFP(75)). Further deletion analysis demonstrated that HA(9)GFP(80) leaving 9 nucleotide residues of the HA coding region at the 3' end resulted in efficient virion incorporation of HA vRNA (more than 65%), although the level of HA(9)GFP(80) vRNA present in transfected cells did not appreciably differ from that of HA(0)GFP(0) vRNA (FIGS. 17 and 18). These results indicate that 9 nucleotides in the 3' end and 80 nucleotides in the 5' end of the HA coding region are required for efficient HA vRNA incorporation into virions.

Generation of a novel influenza A virus whose HA and NA genes contain the coding sequences of foreign genes. Since the sequences required for HA segment incorporation into virions had been determined, it was examined whether a foreign gene flanked by those sequences could be incorporated into influenza A viruses and maintained during repeated passage. As a model foreign gene, the VSV G coding sequence was inserted into the BamHI and XbaI sites of pPolIHA(9)GFP(80) instead of GFP sequence. The resultant construct was designated pPolIHA(9)VSVG(80), possessing the 3' HA noncoding region (33 nucleotides), 9 nucleotides corresponding to the N-terminal HA coding region, the VSV G open reading frame with a stop codon (1552 nucleotides), 80 nucleotides corresponding to the C-terminal HA coding region, and the 5' HA noncoding region (45 nucleotides). As a control, a vector was constructed, pPolIHA(0)VSVG(0), which possesses only the 3' and 5' noncoding regions, but not the coding region of HA vRNA. Since VSV G protein should substitute for both HA and NA proteins, the NA coding region can be substituted with a foreign gene. Therefore, pPolINA (183)GFP(157)Met(−) was constructed for production of a recombinant NA RNA segment containing the GFP coding sequence and the NA coding sequences required for the efficient virion incorporation of NA segment. In this construct, the initiation codon for the NA open reading frame was destroyed by substituting ATG to GCG Thus, the GFP open reading would be translated from its own initiation codon.

Figure 19:
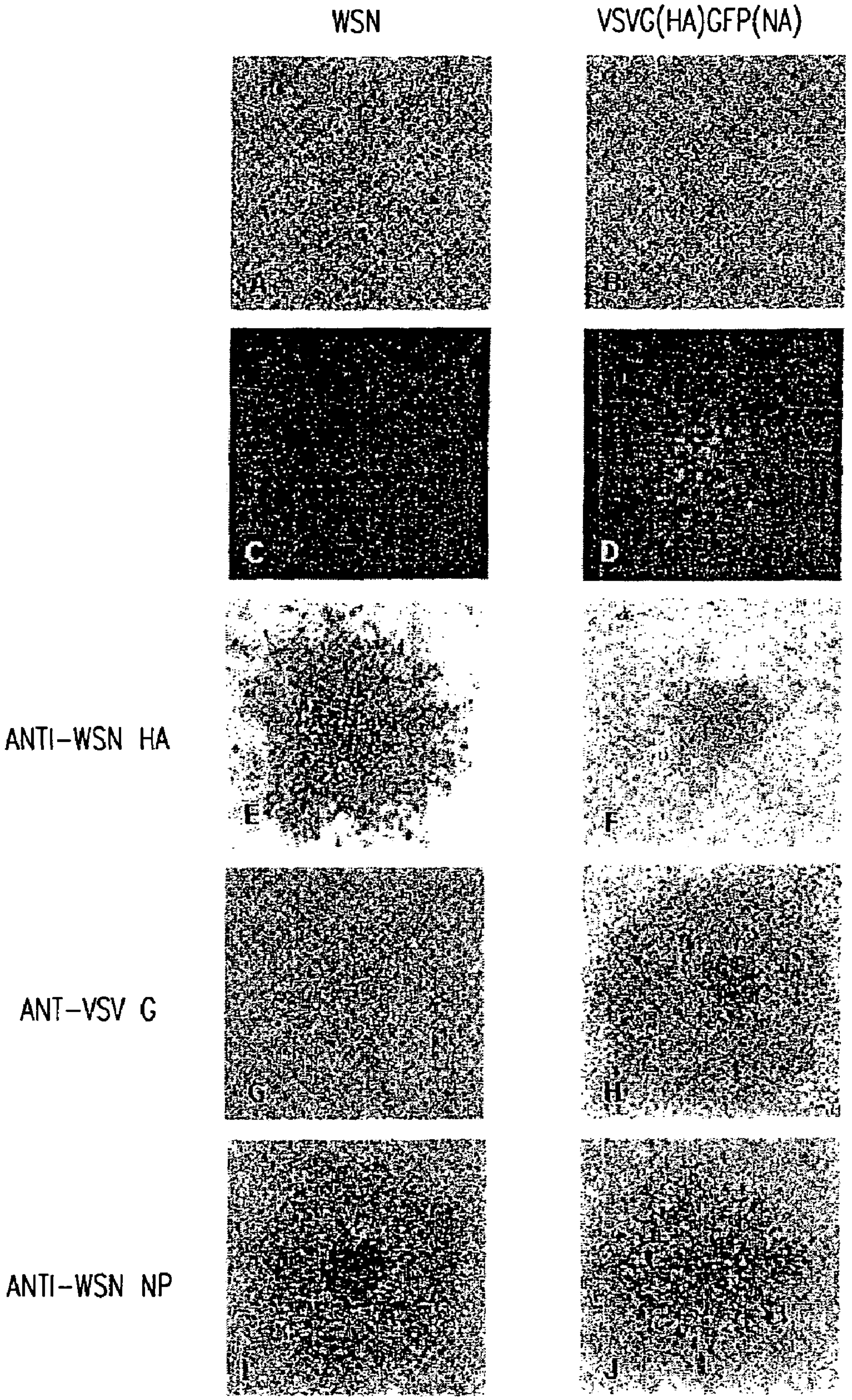
FIG. 19. VSVG(HA)GFP(NA) virus-infected cells express VSV G and GFP. MDCK cells were infected with VSVG (HA)GFP(NA) virus or WSN virus and overlaid with 1.0% agarose. The infected cells were incubated for 48 hours at 37° C., and the plaques were photographed (A, B) under normal light and (C, D) under fluorescent light together with limited normal light to identify plaques. The cells were fixed and permeated with 0.1% Triton-X100 in 3% formaldehyde solution. Viral proteins were detected by immunostaining with anti-VSV G monoclonal antibody (E, F), anti-HA monoclonal antibody (Q H), or anti-NP monoclonal antibody (I, J) as the primary antibody and biotinylated secondary antibody, using the Vectastain ABC kit (Vector, Burlingame, Calif.).

293T cells were transfected with plasmids for the production of both recombinant HA(9)VSVG(80) and NA(183)GFP (157)Met(−) segments and the remaining 6 viral RNA segments, as well as plasmids for the expression of influenza virus polymerase proteins, NP, M1, M2, NS2, and VSV G. At 72 hours after transfection, the supernatants of 293T cells were harvested and plaque assays performed using MDCK cells. A transfectant virus harboring HA(9)VSVG(80) RNA segment and NA(183)GFP(157)Met(−) RNA segment (designated VSVG(HA)GFP(NA) virus) was viable and produced plaques expressing GFP in the absence of trypsin (FIG. 19). Immunostaining confirmed the expression of VSV G, but not HA, containing plaques (FIG. 19). Cells infected with VSVG(HA)GFP(NA) virus, but not control WSN virus, also expressed GFP. By contrast, no plaques were observed when pPolIHA(0)VSVG(0) plasmid was used instead of pPolIHA (9)VSVG(80), although single cells expressing GFP and/or NP protein were detected in MDCK cells (data not shown). Moreover, it was observed that both VSVG and GFP continued to be expressed in MDCK cells infected with the VSVG (HA)GFP(NA) virus after five consecutive passages (data not shown). No mutation was detected in the remaining HA region of the HA(9)VSVG(80) RNA segment of VSVG(HA) GFP(NA) virus after five passages. However, three mutations were found, Ile to Leu at position 57, Gln to His at position 95, and Gln to stop at position 499 in the amino acid sequences of VSVG Although wild-type VSV G protein has 29 residues of cytoplasmic domain, the last 13 residues of this domain were deleted due to the Gln-to-stop mutation at position 499.

Figure 20:
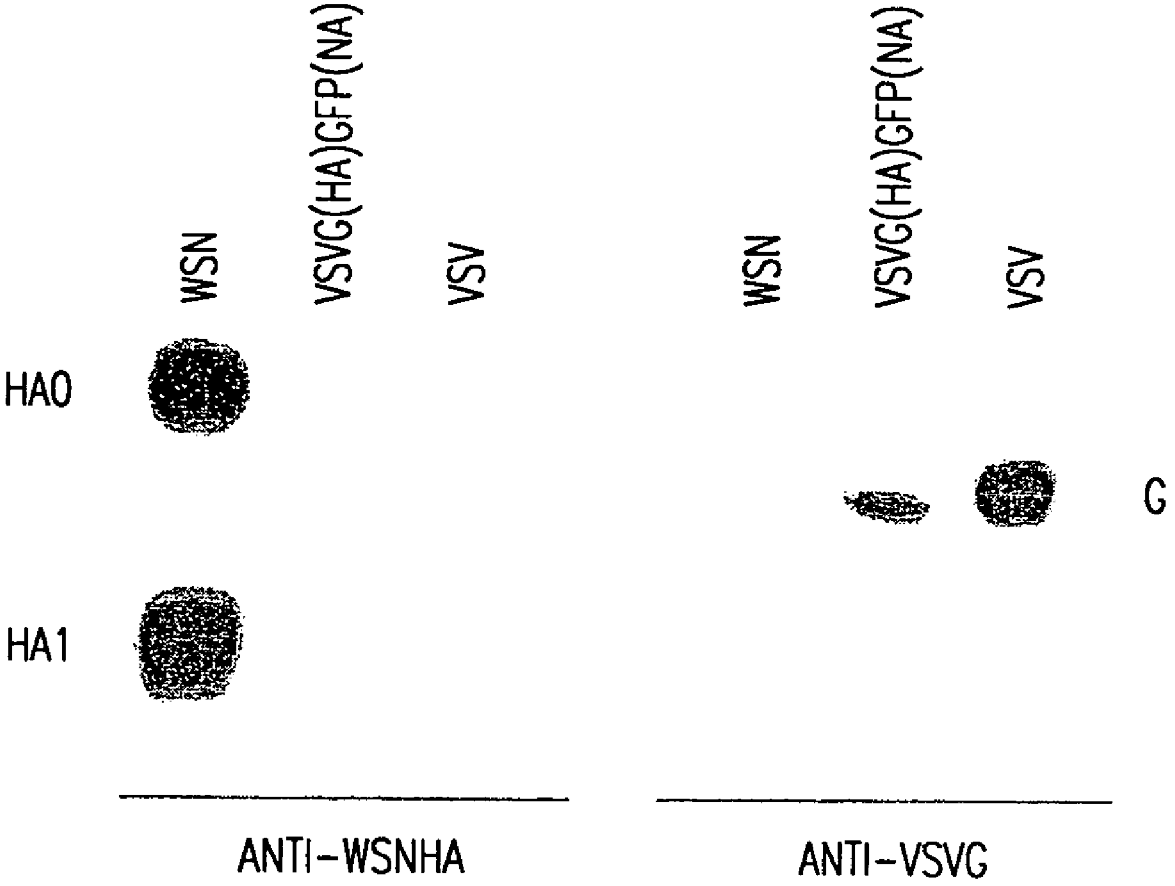
FIG. 20. Incorporation of the VSV G protein into VSVG (HA)GFP(NA) virus. Concentrated WNS, VSVG(HA)GFP (NA), and VSV viruses were lysed in a sample buffer. Viral proteins were treated with 2-mercaptoethanol, separated by 10% SDS-PAGE, transferred to a PVDF membrane, and incubated with anti-VSV G monoclonal antibody or anti-WSN-HA monoclonal antibody. Molecular masses of the marker proteins are shown on the left.

Biological properties of VSVG(HA)GFP(NA) virus. To determine whether VSV G protein is indeed incorporated into virions composed of other influenza viral proteins, Western blot analysis was conducted on concentrated VSVG(HA) GFP(NA) and WSN (control) viruses. As shown in FIG. 20, VSV G protein, but not HA, was detected in VSVG(HA)GFP (NA) virions, confirming virion incorporation of VSV G protein.

Figure 21A:
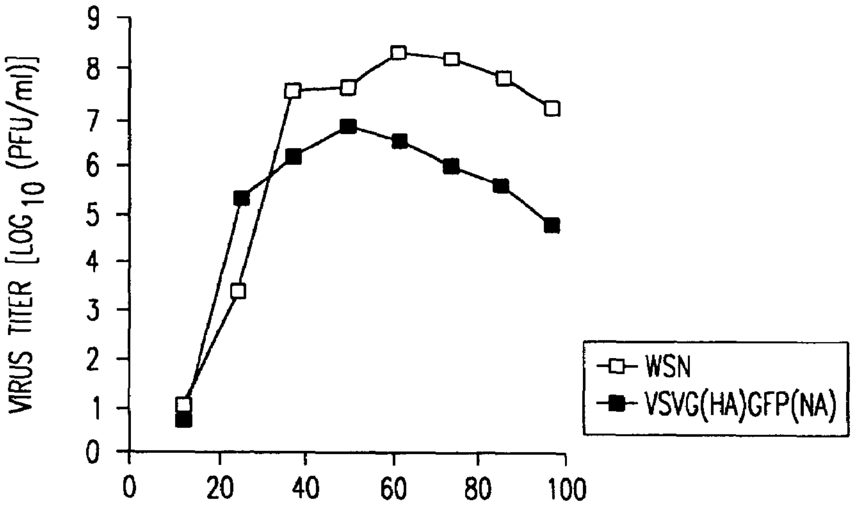
FIG. 21. Growth curves of VSVG(HA)GFP(NA) virus in BHK, CHO, and MDCK cells. BHK (A), CHO (B), and MDCK (C) cells were infected with virus at an MOI of 0.001. At the indicated times after infection, the virus titer in the supernatant was determined using MDCK cells. The values are means of duplicate experiments.
Figure 21B:
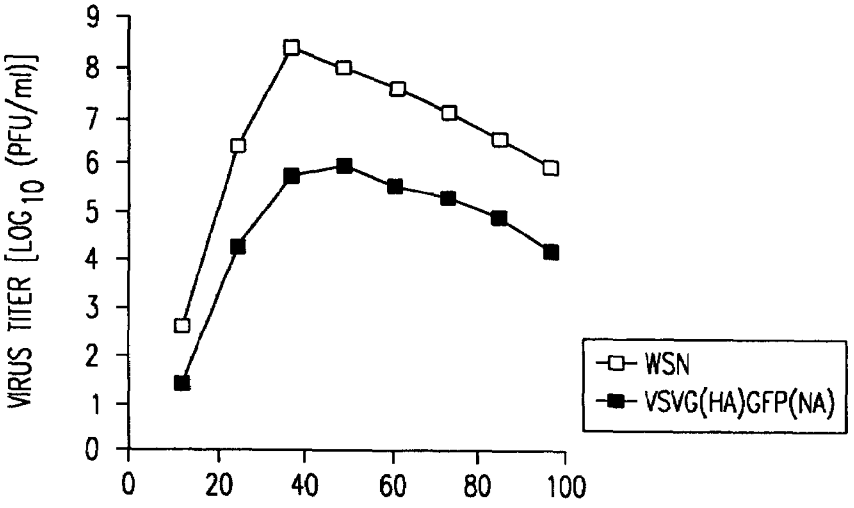
Figure 21C:
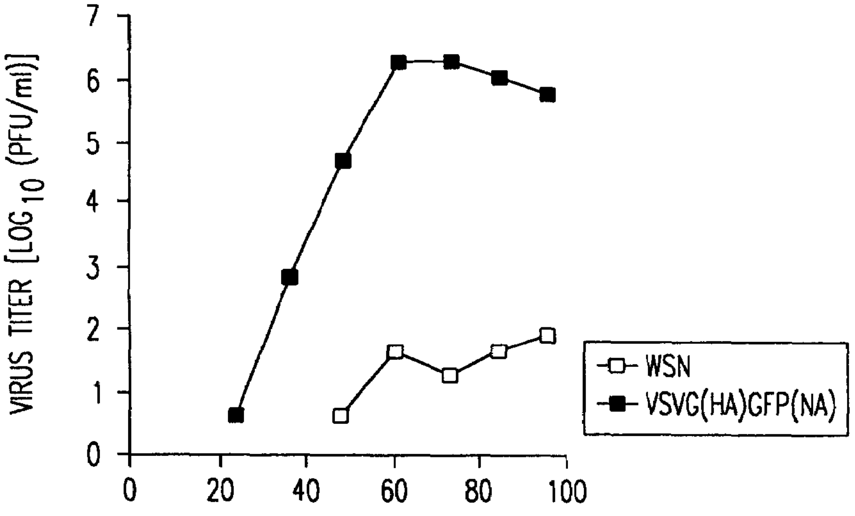

Next, the growth properties of VSVG(HA)GFP(NA) virus were examined in BHK, CHO, or MDCK cells. Cells were infected at an MOI of 0.001, and yields of virus in the culture supernatant were determined at different times post-infection at 37° C. by plaque assay on MDCK cells. Although lower than that of WSN virus, the maximum titer of VSVG(HA) GFP(NA) virus in both BHK and MDCK cells reached at least $10^6$ PFU per ml (FIG. 21). In contrast to the poor growth of WSN virus in CHO cells, VSVG(HA)GFP(NA) virus grew as well in these cells as in the other two cell lines tested (FIG. 21). Moreover, during replication in each of the cell lines, cells infected with VSVG(HA)GFP(NA) virus expressed GFP.

These results indicated that both the HA(9)VSVG(80) and NA(183)GFP(157)Met(−) segments were efficiently incorporated into influenza virions and that two foreign genes could be stably maintained in influenza A virus during repeated passage.

Discussion

Determination of the genome packaging mechanisms is critical for understanding the life cycle of influenza virus as well as for development of influenza virus-based vectors for the expression of foreign proteins. In this study, it was demonstrated that sequences in both the 3' and 5' ends of the coding regions in the HA vRNA were required for efficient incorporation of this segment into virions. Moreover, using this knowledge, a novel influenza-based virus was generated that possesses two recombinant RNA segments containing the coding sequences of VSV G and GFP flanked by sequences necessary for virion incorporation of HA vRNA and NA vRNA, respectively, demonstrating stable expression of two foreign genes.

Figure 24:
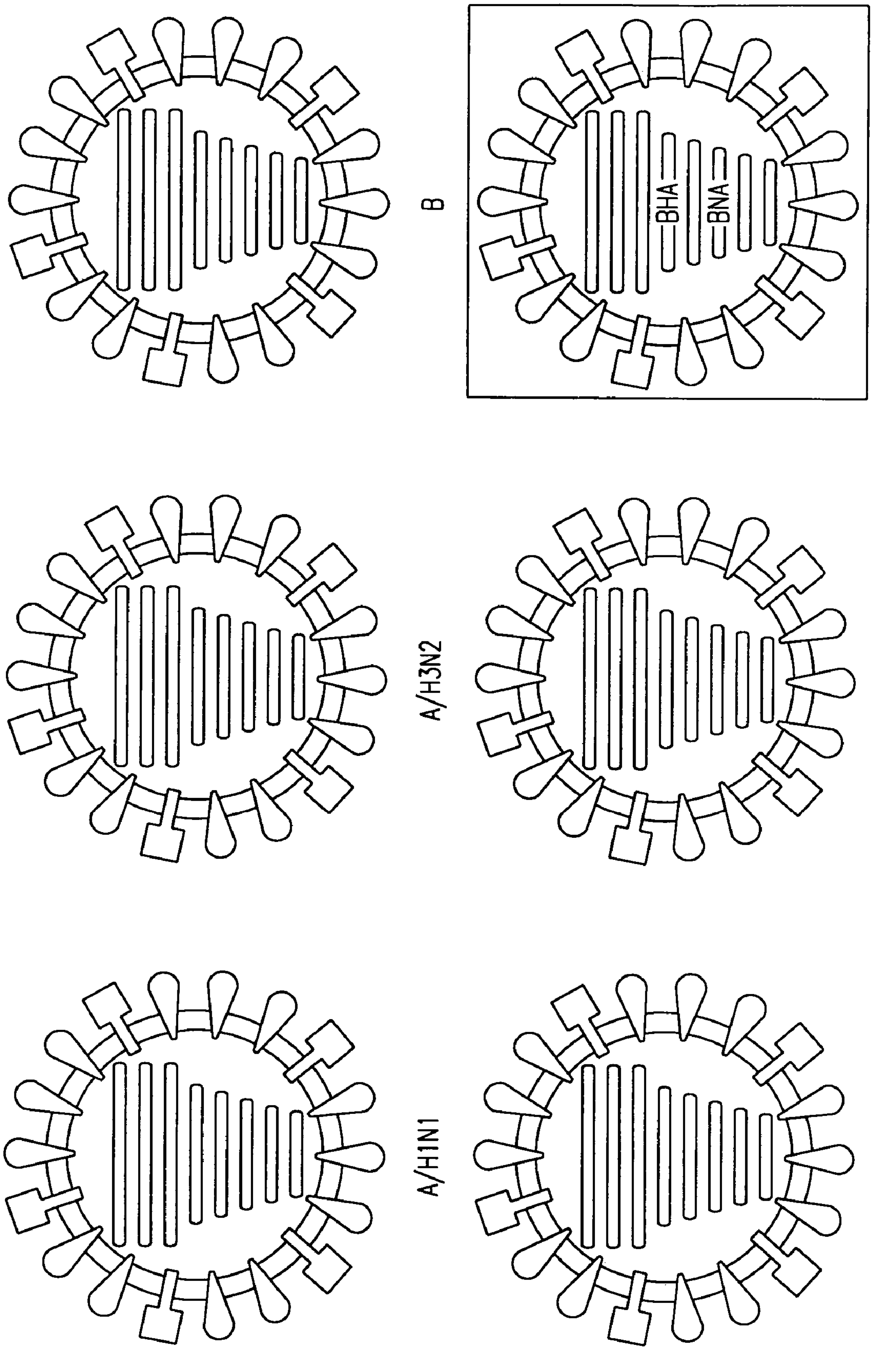
FIG. 24. Schematic of A) viral segments and B) virions expressing two heterologous proteins.
Figure 25:
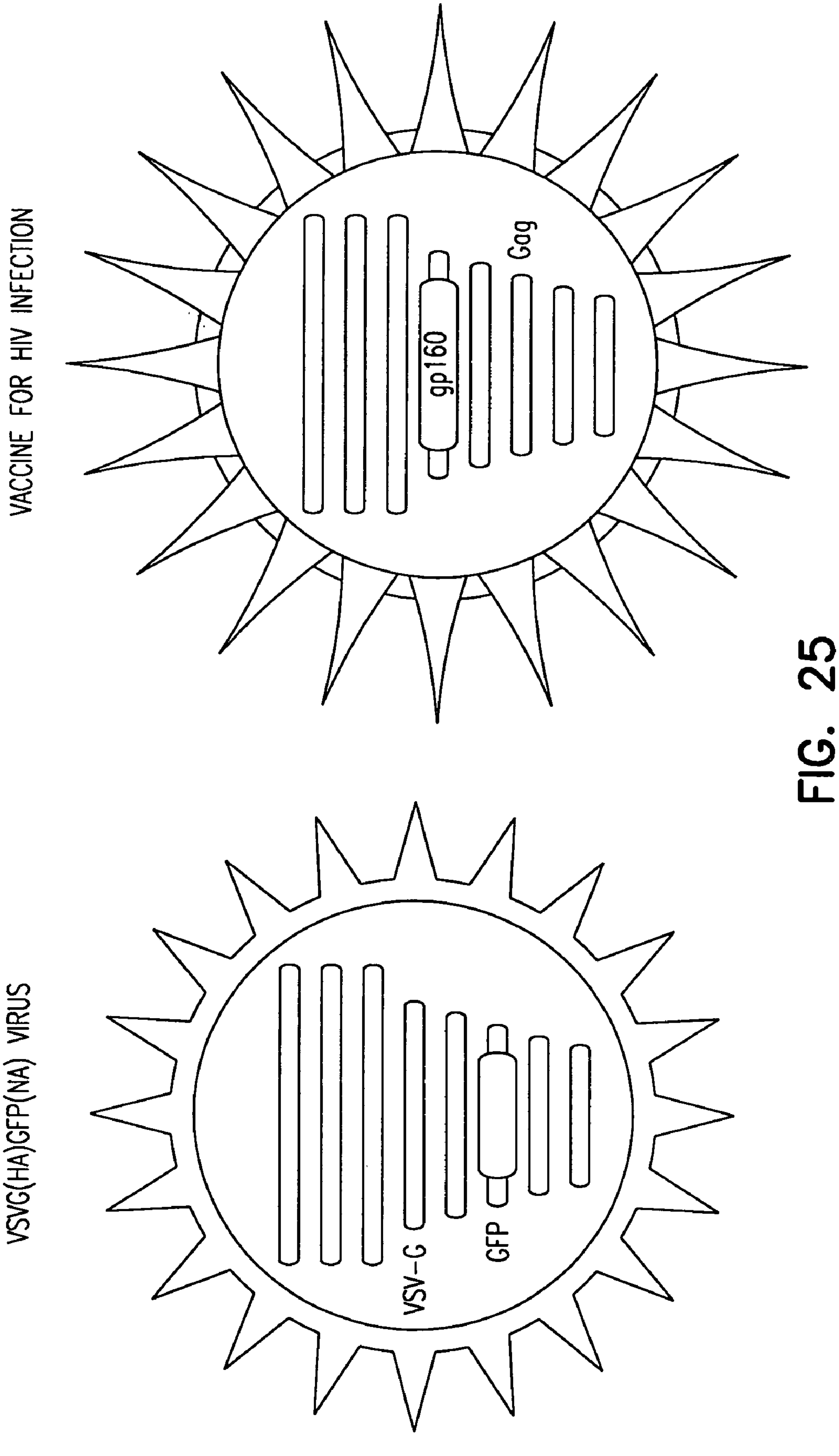
FIG. 25. Schematic of influenza virus with viral segments for two heterologous proteins, HIV gp160 and gag.

Several approaches have been reported for the development of vaccine vectors based on influenza A virus for expression of genes or portions of genes from unrelated infectious agents. Short polypeptides have been inserted into the antigenic sites of HA, resulting in positive immune responses against the inserted peptides. For the expression of longer polypeptides and proteins, the foreign genes have been inserted into one of the influenza virus genes, in which the foreign proteins were expressed by utilizing internal ribosomal entry sites (IRES) or the foot-and-mouth disease virus 2A protease. Here, a new system was established for the expression of a foreign protein, exploiting cis-acting virion incorporation signals in the NA and HA vRNAs. This system enabled influenza-based virus to incorporate more than 1.5 kb of a foreign gene (e.g., VSV G), demonstrating the potential of this vector system. As the vaccine efficacy of replication-incompetent influenza VLPs in mice has been shown, replication-incompetent influenza-based VLPs with a recombinant RNA segment containing a gene from an unrelated pathogen may serve as a promising vaccine. This potential is especially appealing for vaccination against HIV, foot-and-mouth disease and other infections, where any reversion of live vaccine viruses to wild-type is absolutely unacceptable or where the efficacy of inactivated vaccines may be limited due to limited induction of mucosal immunity and cytotoxic T-lymphocyte responses. Thus, using this approach, an influenza virus can be employed as a vaccine vector. For example, one can make a virus that contains a HIV gp160 coding region instead of HA and a gag coding region instead of NA (FIGS. 24 and 25). Moreover, if VSV G replaces HA, M2 is no longer required and so three viral genes may be replaced with heterologous genes. For instance, HA may be replaced with HIV gp160, NA with gag and M2 with nef. The resulting recombinant influenza virus may be employed as a vaccine or as a booster for another HIV vaccine, e.g., a HIV DNA vaccine, to enhance or induce immunity including mucosal immunity. Alternatively, a vaccine may be a multivalent vaccine based on a recombinant influenza virus in which the NA coding segment is replaced with that of another pathogen, e.g., glycoprotein D of herpes virus, which vaccine may result in a protective immune response to influenza virus and herpes virus infections.

Viral vectors derived from adenoviruses, retroviruses, and poxviruses efficiently introduce foreign genes into target cells. Since these viruses contain DNA, or have DNA replication intermediates that could be integrated into the host chromosome, the risk of adverse outcomes cannot be eliminated. By contrast, such integration is improbable in influenza viruses due to the lack of a DNA phase in infected cells. Moreover, since VSVG(HA)GFP(NA) virus does not require trypsin for HA cleavage, unlike typical influenza viruses, it may present a wider use. In addition, recombinant virus with desired cell tropism can be generated by altering a glycoprotein on the virion surface. Thus, the system utilizing cis-acting signals in vRNA segments for virion incorporation allows the design of recombinant influenza-based virus vectors that can deliver multiple foreign genes into target cells.

The assembly and release of viruses from epithelial cells is polarized in some viruses, occurring selectively at either the apical or basolateral surface. Polarized virus budding is thought to play a role in determining the pathogenesis of viral infections. Influenza A virus buds apically from infected epithelial cells and individually expressed HA, NA, and M2 proteins are also targeted to the apical surface of the cells. On the other hand, VSV is released from the basolateral surface of infected cells and VSV G protein is transported to the basolateral surface. In the present study, a recombinant VSVG(HA)GFP(NA) virus, possessing VSV G, instead of the HA and NA proteins, was successfully generated. However, the VSV G protein of this recombinant virus lacked the last 13 residues of the cytoplasmic domain due to a point mutation. Deletion of these 13 residues in the cytoplasmic domain is known to yield a protein that is more efficiently transported to the apical surface than the basolateral surface. Therefore, the mutation introduced into the VSV G protein in VSVG(HA)GFP(NA) virus likely promoted its efficient transport to the apical surface, leading to efficient budding of VSVG(HA)GFP(NA) virus.

Influenza pandemics usually occur when a virus whose HA and/or NA are immunologically distinct from those of the previous circulating strain appears upon reassortment of influenza viral RNA segments. Sequences in the 3' and 5' ends of the coding regions within HA, NA, M, and NS vRNAs are required for their efficient incorporation into virions. The packaging of vRNA segments (most likely as a viral ribonucleoprotein complex) is mediated by RNA-RNA interactions occurring in trans between the viral RNA segments. If so, specific incorporation signals within each segment may restrict reassortment of RNA segments. Empirically, it is known that influenza viral RNA segments do not reassort randomly. Functional interactions among proteins (e.g., formation of the polymerase complex, HA-NA and cleavable HA-M2 functional associations) are thought to restrict random reassortment. In addition to these restrictions on reassortment at the protein level, a similar restriction may exist at the RNA level. In this context, it is interesting that in both the 1957 and 1968 pandemics, PB1 gene in addition to HA and/or NA genes were introduced into human viruses from avian viruses, suggesting a possible link between the HA and PB1 RNA segments. Further characterization of critical regions for virion incorporation of other RNA segments may provide a clue to understanding reassortment of RNA segments, leading to the prediction of the emergence of new pandemic strains of influenza A virus.

In summary, with the information on the vRNA packaging signals, novel influenza vaccines and influenza-based vaccine vectors can be developed.

EXAMPLE 6

Figure 26A:
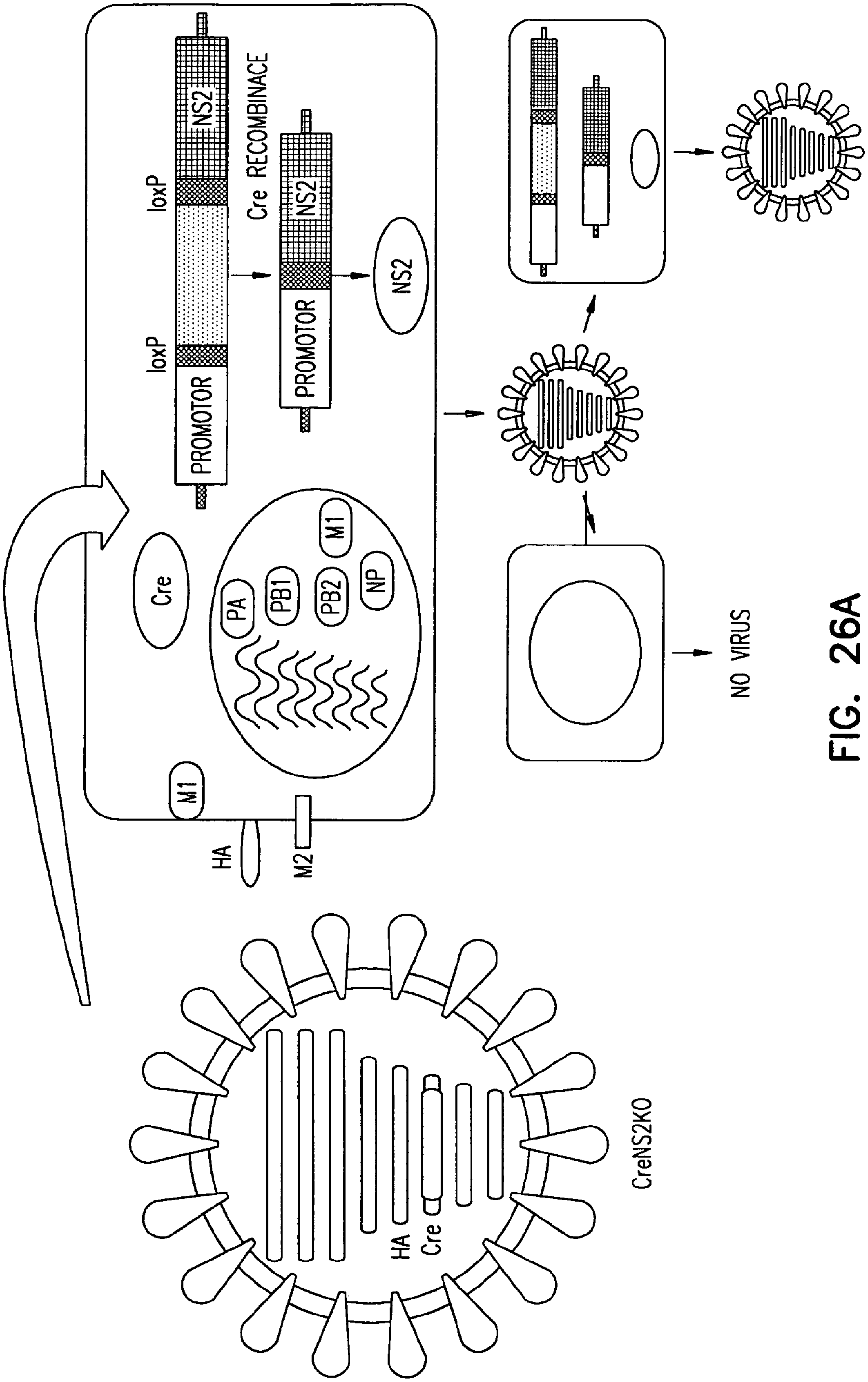
FIG. 26. Schematic of production of replication incompetent virus using Cre/lox.
Figure 26B:
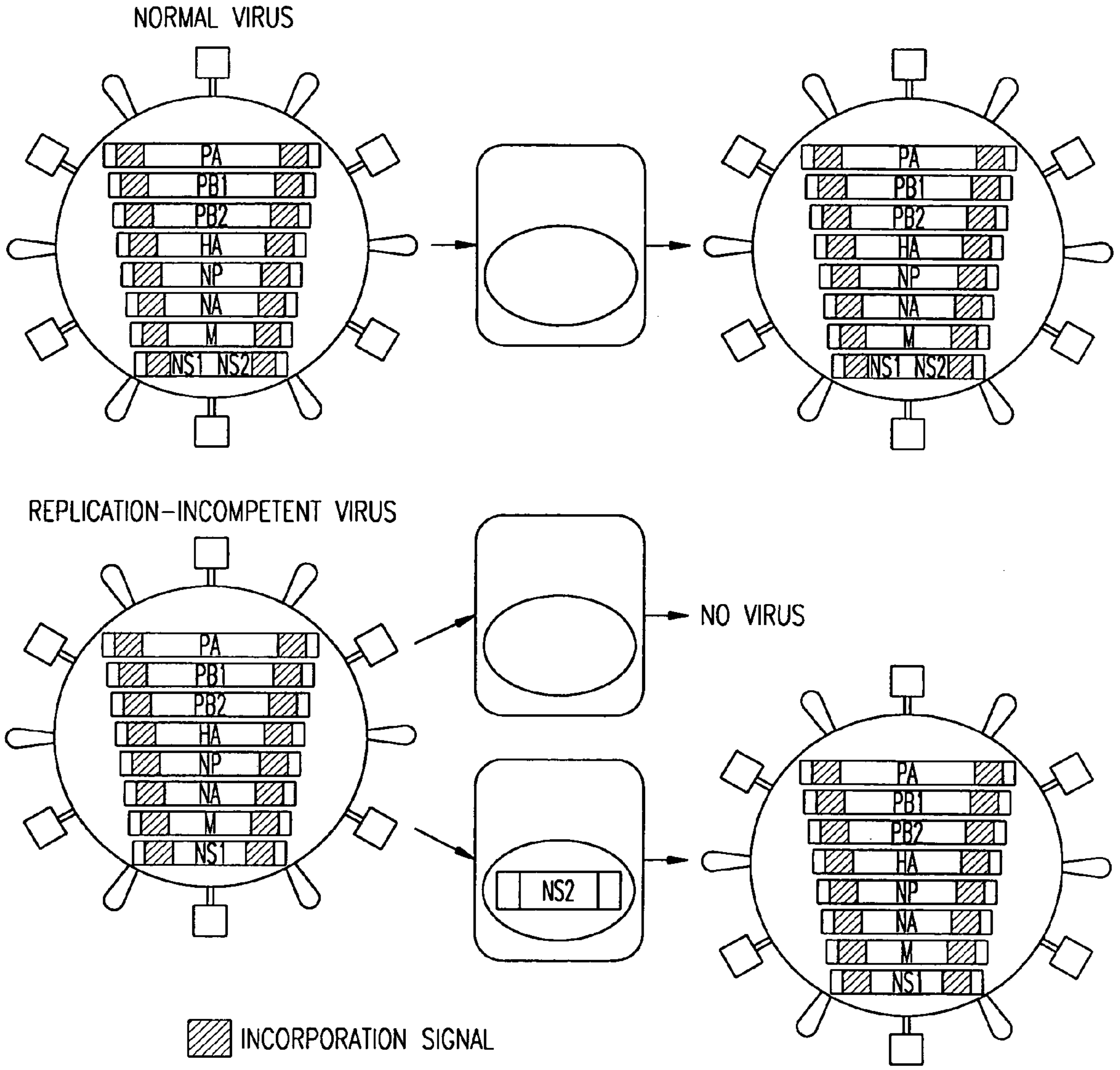

As illustrated in FIG. 26, a cell line that constitutively expresses an influenza virus-like RNA encoding a protein, e.g., NS2, can be made, although this RNA lacks an incorporation signal. A virus which lacks the NS2 coding sequence (NS2 KO) may also be prepared (Neumann et al., 2000; Watanabe et al., 2002). When NS2 KO virus infects normal cells, progeny virus will not be produced, since the virus lacks NS2. In contrast, when NS2 KO virus infects cells expressing an influenza virus-like RNA encoding NS2 but lacking an incorporation signal, NS2 is expressed upon viral infection and progeny NS2 KO virus is produced. However, the influenza virus-like RNA encoding NS2 will not be incorporated into NS2 KO virus because it lacks a virion incorporation signal. Thus, NS2 KO remains replication-incompetent in normal cells. This system can be used for production of producer cells for replication-incompetent viruses. Using this system, producer cells expressing viral proteins, whose toxicity to cells would typically prohibit generation of cell lines constitutively expressing them, can be made. Thus, in this application, the knowledge of virion incorporation signals can be employed to design a system that does not allow a specific segment to be incorporated into virions.

REFERENCES

Air et al., *Struct. Func. Genet.,* 6:341 (1989).

Ali et al., *J. Virol.,* 74:8709 (2000).

Avery's Drug Treatment: Principles and Practice of Clinical Pharmacology and Therapeutics, 3rd edition, ADIS Press, LTD., Williams and Wilkins, Baltimore, Md. (1987).

Baum et al., *Virology,* 180:10 (1991).

Bean et al., *J. Virol.,* 66:1129 (1992).

Berkow et al., The Merck Manual, 15th edition, Merck and Co., Rahway, N.J. (1987).

Carroll et al., *Virus Res.,* 3:165 (1985).

Crescenzo-Chaigne et al., *Virology:* 265:342 (1999).

Desselberger et al., *Gene,* 8:315 (1980).

Ebadi, *Pharmacology*, Little, Brown and Co., Boston, Mass. (1985).

Edwards, *J. Infect. Dis.,* 169:68 (1994).

Enami et al., *J. Virol.,* 70:6653 (1996).

Ewami et al., *Proc. Natl. Acad. Sci. USA,* 87:3802 (1990).

Fodor et al., *J. Virol.,* 23:9679 (1999).

Fujii et al., *Virus,* 52:203 (2002).

Ghate et al., *Virology,* 264:265 (1999).

Goodman et al., eds., Goodman and Gilman's The Pharmacological Basis of Therapeutics, 8th edition, Pergamon Press, Inc., Elmsford, N.Y. (1990).

Hara et al., *Anal. Biochem.,* 164:138 (1987).

Hinshaw et al., *Virology,* 128:260 (1983).

Hughes et al., *J. Virol.,* 74:5206 (2000).

Ito et al., *J. Virol.,* 71:3357 (1997).

Jambrina et al., *Virology,* 235:209 (1997).

Jin et al., *EMBO J.,* 16:1236 (1997).

Katzung, ed., Basic and Clinical Pharmacology, Fifth Edition, Appleton and Lange, Norwalk, Conn. (1992).

Kaverin et al., *J. Gen. Virol.,* 64:2139 (1983).

Kawaoka et al., *J. Virol.,* 63:4603 (1989).

Kendal et al., *Infect. Immun.,* 29:966 (1980).

Kerr et al., *Lancet,* 1:291 (1975).

Kida et al., *Virology,* 122:38 (1982).

Kilbourne, *Bull. M2 World Health Org.,* 41:643 (1969).

Kobasa et al., *J. Virol.,* 71:6706 (1997).

Krug, R. M., ed., The Influenza Viruses, Plenum Press, New York (1989).

Lamb et al., In B. N. Fields, D. M. Knipe, and P. M. Howley (ed.), Fields Virology, 3rd ed. Lippincott-Raven Publishers, Philadelphia, Pa., p. 1353-1395, (1996).

Lamb et al., Orthomyxoviridae: The viruses and their replication. In Fields Virology (4th edn) (Knipe, D. M., et al. eds) pp. 1487-1531 (2000).

Layer et al., *Virology,* 51:383 (1973).

Liu et al., *J. Virol.,* 69:1099 (1995).

Liu et al., *Virology,* 194:403 (1993).

Luo et al., *J. Gen. Virol.,* 80:2969 (1999).

Luytjes et al., *Cell,* 59:1107 (1989).

Maassab et al., *Rev. Med. Virol.,* 9:237 (1999).

Mikheeva et al., *Arch. Virol.,* 73:287 (1982).

Mitnaul et al., *J. Virol.,* 74:6015 (2000).

Mizrahi, ed, Viral Vaccines, Wiley-Liss, New York (1990).

Murphy, *Infect. Dis. Clin. Pract.,* 2:174 (1993).

Muster et al., *Proc. Natl. Acad. Sci. USA,* 88:5177 (1991).

Neumann et al., *Proc. Natl. Acad. Sci. USA,* 96:9345 (1999).

Neumann et al., *EMBO J.,* 19:6751 (2000).

Ogra et al., *J. Infect. Dis.,* 135:499 (1977).

Palese et al., *Virology,* 61:397 (1974).

Portela et al., *Adv. Virus Res.,* 54:319 (1999).

Ray et al., *J. Biol. Chem.,* 268:18 (1991).

Robertson et al., *Biologicals,* 20:213 (1992).

Robertson et al., *Giornale di Igiene e Medicina Preventiva,* 29:4 (1988).

Rogers et al., *Virology,* 127:361 (1983a).

Rogers et al., *Virology,* 131:394 (1983b).

Scholtissek et al., *Virology,* 87:13 (1978).

Shibata et al., *J. Virol.,* 67:3264 (1993).

Shibuya et al., *J. Biol. Chem.,* 262:1596 (1987).

Subbarao et al., *J. Virol.,* 67:7223 (1993).

Suzuki et al., *FEBS Lett.,* 404:192 (1997).

Tobita et al., *Arch. Virol.,* 75:17 (1983).

Wagner et al., *Rev. Med. Virol.,* 12:159 (2002).

Wang et al., *J. Biol. Chem.,* 263:4576 (1988).

Warening et al., *Vaccine,* 19:3320 (2001).

Watanabe et al., *J. Virol.,* 76:767 (2002).

Webster et al., *Microbiol. Rev.,* 56:152 (1992).

Wiley et al., *Annu. Ref. Biochem.,* 56:3665 (1987).

Wright et al., Orthomyxovirses, In: *Fields Virology*, Knipe et al. (eds), Lippincott-Raven Publishers, Philadelphia, Pa. (2000).

Wright et al., Orthomyxoviruses. In Fields Virology (4th edn) (Knipe, D. M., et al. eds) pp. 1533-1579 (2000).
Yang et al., *Virology,* 229:155 (1997).
Zhang et al., *J. Virol.,* 74:4634 (2000).

All publications, patents and patent applications are incorporated herein by reference. While in the foregoing specification this invention has been described in relation to certain preferred embodiments thereof, and many details have been set forth for purposes of illustration, it will be apparent to those skilled in the art that the invention is susceptible to additional embodiments and that certain of the details described herein may be varied considerably without departing from the basic principles of the invention.

What is claimed is:

1. An influenza viral vector, comprising influenza virus incorporation sequences, which vector comprises:

sequences corresponding to the 3' noncoding region of influenza virus HA vRNA and HA coding sequences which include 3' HA incorporation sequences, a nucleic acid segment for a heterologous open reading frame which encodes a gene product, and HA coding sequences which include 5' HA incorporation sequences and the 5' noncoding region of HA vRNA, wherein the HA coding sequences which include 3' HA incorporation sequences include at least 3 nucleotides of 5' HA coding sequence and the HA coding sequences which include the 5' HA incorporation sequences have no more than 1011 nucleotides of 3' HA coding sequences.

2. The vector of claim 1 wherein the 5' HA incorporation sequences include at least 80 nucleotides corresponding to the 80 3N coding nucleotides of HA.

3. The vector of claim 1 wherein the 5' HA incorporation sequences include at least 291 nucleotides corresponding to the 291 3N coding nucleotides of HA.

4. The vector of claim 1 wherein the 3' HA incorporation sequences include at least 9 nucleotides corresponding to the first 9 coding nucleotides for HA.

5. The vector of claim 1 wherein the heterologous nucleic acid segment comprises sequences corresponding to an internal ribosome entry sequence.

6. The vector of claim 1 wherein the heterologous nucleic acid segment comprises sequences corresponding to an open reading frame for a marker gene.

7. The vector of claim 1 wherein the heterologous nucleic acid segment comprises sequences corresponding to an open reading frame for an immunogenic protein or a peptide of a pathogen, or a therapeutic protein.

8. The vector of claim 1 wherein incorporation sequences are from a type A influenza virus.

9. The vector of claim 1 wherein the incorporation sequences are from a type B influenza virus.

10. The vector of claim 1 wherein the heterologous nucleic acid segment is fused to another nucleic acid segment so as to encode a fusion protein.

11. A recombinant influenza virus comprising a vRNA corresponding to the vector of claim 1.

12. The recombinant virus of claim 11 wherein the heterologous nucleic acid segment comprises sequences corresponding to an open reading frame for a marker gene.

13. The recombinant virus of claim 11 wherein the heterologous nucleic acid segment comprises sequences corresponding to an open reading frame for an immunogenic protein or peptide of a pathogen.

14. The recombinant virus of claim 13 wherein the open reading frame encodes an influenza virus HA protein.

15. The recombinant virus of claim 13 wherein the open reading frame encodes an influenza virus NA protein.

16. The recombinant virus of claim 11 wherein the heterologous nucleic acid segment comprises sequences corresponding to an open reading frame for a transmembrane protein.

17. The recombinant virus of claim 11 wherein the heterologous nucleic acid segment comprises sequences corresponding to an open reading frame for a protein with membrane fusing activity.

18. The recombinant virus of claim 11 wherein the heterologous nucleic acid segment comprises sequences corresponding to an open reading frame for a viral capsid protein.

19. The recombinant virus of claim 11 wherein the heterologous nucleic acid segment comprises sequences corresponding to an open reading frame for vesicular stomatitis virus G protein.

20. The recombinant virus of claim 11 wherein the heterologous nucleic acid segment comprises sequences corresponding to an open reading frame for a therapeutic protein.

21. The recombinant virus of claim 14 wherein the influenza virus HA protein is a type B HA protein.

22. A method to express a heterologous nucleic acid segment in a cell, comprising: contacting a cell with the recombinant virus of claim 11 and detecting or determining whether a product encoded by the heterologous nucleic acid segment is expressed in the cell.

23. An isolated nucleic acid molecule comprising sequences corresponding to the 3' noncoding region of influenza virus HA vRNA which include 3' HA incorporation sequences, a nucleic acid segment for a heterologous open reading frame which encodes a gene product, and influenza virus 5' HA incorporation sequences that include sequences corresponding to the 3' coding region of HA, wherein the 3' HA coding region is no more than 1011 nucleotides, and wherein the nucleic acid molecule does not include incorporation sequences corresponding to the 5' HA coding region.

24. The vector of claim 1 wherein vRNA corresponding to the vector, when present in the cell, is packaged into virions at an efficiency at least 10% that of a corresponding wild-type vRNA.

25. The vector of claim 1 wherein vRNA corresponding to the vector, when present in the cell, is packaged into virions at an efficiency at least 30% that of a corresponding wild-type vRNA.

26. The vector of claim 1 wherein vRNA corresponding to the vector, when present in the cell, is packaged into virions at an efficiency at least 60% that of a corresponding wild-type vRNA.

27. A vector comprising sequences corresponding to the 3' noncoding region of influenza virus HA vRNA and HA coding sequences which include 3' HA incorporation sequences, a nucleic acid segment for a heterologous open reading frame which encodes a gene product, and HA coding sequences which include 5' HA incorporation sequences and the 5' noncoding region of HA vRNA, wherein the HA coding sequences which include 3' HA incorporation sequences include at least 3 nucleotides of 5' HA coding sequence and the HA coding sequences which include the 5' HA incorporation sequences have no more than 1011 nucleotides of 3' HA coding sequences.

28. An influenza viral vector, comprising influenza virus incorporation sequences, which vector comprises:

sequences corresponding to the 3' noncoding region of influenza virus HA vRNA and HA coding sequences which include 3' HA incorporation sequences, a nucleic acid segment for a heterologous open reading frame which encodes a gene product, and HA coding sequences which include 5' HA incorporation sequences and the 5' noncoding region of HA vRNA, wherein the HA coding sequences which include 3' HA incorporation sequences include no more than 966 nucleotides of 5' HA coding sequence and the HA coding sequences which include the 5' HA incorporation sequences have at least 54 nucleotides of 3' HA coding sequences.

29. A vector comprising sequences corresponding to the 3' noncoding region of influenza virus HA vRNA and HA coding sequences which include 3' HA incorporation sequences, a nucleic acid segment for a heterologous open reading frame which encodes a gene product, and HA coding sequences which include 5' HA incorporation sequences and the 5' noncoding region of HA vRNA, wherein the HA coding sequences which include 3' HA incorporation sequences include no more than 966 nucleotides of 5' HA coding sequence and the HA coding sequences which include the 5' HA incorporation sequences have at least 54 nucleotides of 3' HA coding sequences.

30. The vector of claim 1 or 27 wherein the 5' HA incorporation sequences have no more than 513 nucleotides of 3N HA coding sequences.

31. The vector of claim 28 or 29 wherein the 3' HA incorporation sequences have no more than 468 nucleotides of 5' HA coding sequences.

* * * * *

UNITED STATES PATENT AND TRADEMARK OFFICE

CERTIFICATE OF CORRECTION

PATENT NO. : 7,585,657 B2
APPLICATION NO. : 11/509249
DATED : September 8, 2009
INVENTOR(S) : Kawaoka It is certified that error appears in the above-identified patent and that said Letters Patent is hereby corrected as shown below:

On the Title Pg Item (54), line 2, delete "VECTOR" and insert -- VECTORS --, therefor.

On the Title Pg Item (75), in "Inventor", line 1, delete "Middletown," and insert -- Middleton, --, therefor.

On the Title Pg Item (56), under "Other Publications", line 3, delete "retreived" and insert -- retrieved --, therefor.

On the Title Pg Item (56), under "Other Publications", line 3, delete "Retreived" and insert -- retrieved --, therefor.

On the Title Pg Item (56), under "Other Publications", line 6, delete "Trail of Influeza" and insert -- Tail of Influenza --, therefor.

On the Title Pg Item (56), under "Other Publications", line 6, delete "Epitiope" and insert -- Epitope --, therefor.

On the Title Pg Item (56), under "Other Publications", line 31, delete ""Intoduction" and insert -- "Introduction --, therefor.

On the Title Pg Item (56), under "Other Publications", line 37, delete "Gillenland," and insert -- Gilleland, --, therefor.

In column 1, line 2, delete "VECTOR" and insert -- VECTORS --, therefor.

In column 46, line 54, in Claim 2, delete "3N" and insert -- 3' --, therefor.

In column 46, line 57, in Claim 3, delete "3N" and insert -- 3' --, therefor.

UNITED STATES PATENT AND TRADEMARK OFFICE

CERTIFICATE OF CORRECTION

PATENT NO. : 7,585,657 B2
APPLICATION NO. : 11/509249
DATED : September 8, 2009
INVENTOR(S) : Kawaoka It is certified that error appears in the above-identified patent and that said Letters Patent is hereby corrected as shown below:

In column 48, line 53, in Claim 30, delete “3N” and insert -- 3' --, therefor.

Signed and Sealed this

Twenty-ninth Day of December, 2009

David J. Kappos

*Director of the United States Patent and Trademark Office*

UNITED STATES PATENT AND TRADEMARK OFFICE

CERTIFICATE OF CORRECTION

PATENT NO. : 7,585,657 B2
APPLICATION NO. : 11/509249
DATED : September 8, 2009
INVENTOR(S) : Yoshihiro Kawaoka It is certified that error appears in the above-identified patent and that said Letters Patent is hereby corrected as shown below:

In column 1, line 17-20, delete "The invention was made, at least in part, with a grant from the Government of the United States of America (grant A147446 from the National Institutes of Health). The government has certain rights in the invention." and insert -- This invention was made with United States government support awarded by the following agencies: NIH AI047446 from the National Institutes of Health. The United States government has certain rights in this invention. --, therefor.

Signed and Sealed this

Eighth Day of June, 2010

David J. Kappos

David J. Kappos
*Director of the United States Patent and Trademark Office*

SEQUENCE LISTING

<160> NUMBER OF SEQ ID NOS: 10

<210> SEQ ID NO 1
<211> LENGTH: 24
<212> TYPE: DNA
<213> ORGANISM: Artificial Sequence
<220> FEATURE:
<223> OTHER INFORMATION: Synthesized NA gene-specific primer

<400> SEQUENCE: 1
tggctcgttt ctctcactat tgcc 24

<210> SEQ ID NO 2
<211> LENGTH: 26
<212> TYPE: DNA
<213> ORGANISM: Artificial Sequence
<220> FEATURE:
<223> OTHER INFORMATION: Synthesized NA gene-specific primer

<400> SEQUENCE: 2
ttatataggc atgagattga tgtccg 26

<210> SEQ ID NO 3
<211> LENGTH: 37
<212> TYPE: DNA
<213> ORGANISM: Artificial Sequence
<220> FEATURE:
<223> OTHER INFORMATION: Synthesized HA gene-specific primer

<400> SEQUENCE: 3
agcaaaagca ggggataatt ctattaacca tgaagac 37

<210> SEQ ID NO 4
<211> LENGTH: 34
<212> TYPE: DNA
<213> ORGANISM: Artificial Sequence
<220> FEATURE:
<223> OTHER INFORMATION: Synthesized HA gene-specific primer

<400> SEQUENCE: 4
agtagaaaca agggtgtttt taattaatgc actc 34

<210> SEQ ID NO 5
<211> LENGTH: 8
<212> TYPE: PRT
<213> ORGANISM: Artificial Sequence
<220> FEATURE:
<223> OTHER INFORMATION: Synthesized FLAG epitope

<400> SEQUENCE: 5

Asp Tyr Lys Asp Asp Asp Asp Lys
1 5

<210> SEQ ID NO 6
<211> LENGTH: 6
<212> TYPE: DNA

-continued

```
<213> ORGANISM: Artificial Sequence
<220> FEATURE:
<223> OTHER INFORMATION: Synthesized - two sequential stop codons

<400> SEQUENCE: 6

taatag                                                                 6


<210> SEQ ID NO 7
<211> LENGTH: 24
<212> TYPE: DNA
<213> ORGANISM: Artificial Sequence
<220> FEATURE:
<223> OTHER INFORMATION: Synthesized oligonucleotide complementary to
      the nucleotide sequence encoding the FLAG epitope

<400> SEQUENCE: 7

gactacaagg acgacgatga caag                                            24


<210> SEQ ID NO 8
<211> LENGTH: 31
<212> TYPE: DNA
<213> ORGANISM: Artificial Sequence
<220> FEATURE:
<223> OTHER INFORMATION: Synthesized oligonucleotide probe complementary
      to the GFP sequence

<400> SEQUENCE: 8

atggccgaca agcagaagaa cggcatcaag g                                    31


<210> SEQ ID NO 9
<211> LENGTH: 29
<212> TYPE: DNA
<213> ORGANISM: Artificial Sequence
<220> FEATURE:
<223> OTHER INFORMATION: Synthesized PCR primer

<400> SEQUENCE: 9

gcggatcctc ccctatggga gcatgatac                                       29


<210> SEQ ID NO 10
<211> LENGTH: 29
<212> TYPE: DNA
<213> ORGANISM: Artificial Sequence
<220> FEATURE:
<223> OTHER INFORMATION: Synthesized PCR primer

<400> SEQUENCE: 10

gctctagaaa ctctgttatc gagaaaatg                                       29
```